US009585883B2

(12) United States Patent
Oslob et al.

(10) Patent No.: US 9,585,883 B2
(45) Date of Patent: Mar. 7, 2017

(54) PYRIMIDINEDIONE COMPOUNDS

(71) Applicant: MyoKardia, Inc., South San Francisco, CA (US)

(72) Inventors: Johan Oslob, Sunnyvale, CA (US); Robert Anderson, Brisbane, CA (US); Danielle Aubele, San Mateo, CA (US); Marc Evanchik, San Jose, CA (US); Jonathan Charles Fox, San Francisco, CA (US); Brian Kane, Oakland, CA (US); Puping Lu, Foster City, CA (US); Robert McDowell, San Francisco, CA (US); Hector Rodriguez, Brisbane, CA (US); Yonghong Song, Foster City, CA (US); Arvinder Sran, Fremont, CA (US)

(73) Assignee: MYOKARDIA, INC., South San Francisco, CA (US)

( * ) Notice: Subject to any disclaimer, the term of this patent is extended or adjusted under 35 U.S.C. 154(b) by 0 days.

(21) Appl. No.: 14/883,152

(22) Filed: Oct. 14, 2015

(65) Prior Publication Data

US 2016/0030428 A1  Feb. 4, 2016

Related U.S. Application Data

(62) Division of application No. 14/309,381, filed on Jun. 19, 2014, now Pat. No. 9,181,200.

(60) Provisional application No. 61/838,088, filed on Jun. 21, 2013, provisional application No. 61/939,655, filed on Feb. 13, 2014, provisional application No. 61/981,366, filed on Apr. 18, 2014.

(51) Int. Cl.
| | |
|---|---|
| *A61K 31/513* | (2006.01) |
| *A61K 45/06* | (2006.01) |
| *C07D 239/545* | (2006.01) |
| *C07D 239/553* | (2006.01) |
| *C07D 401/04* | (2006.01) |
| *C07D 403/04* | (2006.01) |
| *C07D 403/12* | (2006.01) |
| *C07D 405/04* | (2006.01) |
| *C07D 405/12* | (2006.01) |
| *C07D 413/04* | (2006.01) |
| *C07D 401/12* | (2006.01) |
| *C07D 413/12* | (2006.01) |

(52) U.S. Cl.
CPC ............ *A61K 31/513* (2013.01); *A61K 45/06* (2013.01); *C07D 239/545* (2013.01); *C07D 239/553* (2013.01); *C07D 401/04* (2013.01); *C07D 401/12* (2013.01); *C07D 403/04* (2013.01); *C07D 403/12* (2013.01); *C07D 405/04* (2013.01); *C07D 405/12* (2013.01); *C07D 413/04* (2013.01); *C07D 413/12* (2013.01)

(58) Field of Classification Search
CPC  C07D 401/04; C07D 403/04; C07D 239/545; C07D 405/04; C07D 239/553; C07D 401/12; C07D 403/12; C07D 413/04; C07D 405/12; A61K 31/513; A61K 45/06
See application file for complete search history.

(56) References Cited

U.S. PATENT DOCUMENTS

| | | | |
|---|---|---|---|
| 5,008,267 | A | 4/1991 | Katakami et al. |
| 5,516,905 | A | 5/1996 | Brown et al. |
| 6,174,941 | B1 | 1/2001 | Wehner et al. |
| 6,495,337 | B1 | 12/2002 | Hartman et al. |
| 6,509,167 | B1 | 1/2003 | Hartman et al. |
| 6,573,061 | B1 | 6/2003 | Hartman et al. |
| 6,759,240 | B1 | 7/2004 | Hartman et al. |
| 7,160,893 | B2 | 1/2007 | Hicks et al. |
| 7,202,051 | B1 | 4/2007 | Finer et al. |
| 7,214,503 | B2 | 5/2007 | Hartman et al. |
| 7,416,856 | B2 | 8/2008 | Baliga et al. |
| 7,781,584 | B2 | 8/2010 | Feng et al. |
| 7,824,880 | B2 | 11/2010 | Baliga et al. |
| 8,642,660 | B2 | 2/2014 | Goldfarb |
| 9,181,200 | B2 * | 11/2015 | Oslob ............... A61K 31/513 |
| 9,199,945 | B2 * | 12/2015 | Oslob ............... A61K 31/513 |
| 2003/0114414 | A1 | 6/2003 | Zhi et al. |
| 2009/0163545 | A1 | 6/2009 | Goldfarb |
| 2012/0122925 | A1 | 5/2012 | Ashrafian et al. |

FOREIGN PATENT DOCUMENTS

| | | |
|---|---|---|
| DE | 1280877 B | 10/1968 |
| EP | 0447324 A1 | 9/1991 |
| JP | 61205261 A2 | 9/1986 |
| JP | H06-128238 A | 5/1994 |

(Continued)

OTHER PUBLICATIONS

H. Goldner et al., 692 Justus Liebigs Annalen der Chemie, 134-150 (1966).*

(Continued)

*Primary Examiner* — Alexander R Pagano

(74) *Attorney, Agent, or Firm* — Mintz, Levin, Cohn, Ferris, Glovsky and Popeo, P.C.

(57) ABSTRACT

Provided are novel pyrimidine dione compounds and pharmaceutically acceptable salts thereof, that are useful for the treatment of hypertrophic cardiomyopathy (HCM) and conditions associated with left ventricular hypertrophy or diastolic dysfunction. The synthesis and characterization of the compounds and pharmaceutically acceptable salts thereof, are described, as well as methods for treating HCM and other forms of heart disease.

18 Claims, 1 Drawing Sheet

(56) References Cited

FOREIGN PATENT DOCUMENTS

| WO | 96/06614 | A1 | 3/1996 |
|---|---|---|---|
| WO | 01/29010 | A1 | 4/2001 |
| WO | 02/102769 | A2 | 12/2002 |
| WO | 2004/014868 | A2 | 2/2004 |
| WO | 2005/095381 | A1 | 10/2005 |
| WO | 2006/089221 | A2 | 8/2006 |

OTHER PUBLICATIONS

International Search Report and Written Opinion dated Sep. 4, 2014, corresponding to International Application No. PCT/US2014/043192, 11 pages.

Dimoglo, A. S. et al., "Influence of Structural and Electronic Properties of Uranyl Derivatives on the Inhibition of Thymidine Phosphorylase," *Institute of Chemistry, Academy of Sciences of the Moldavian SSR, Kishinev*, pp. 628-636 © 1986 Plenum Publishing Corporation. Translated from Khimikofarmatsevticheskii Zhurnal, (Sep. 1985; Original article submitted Jul. 3, 1984) 19(9):1086-1096.

Goldner et al., "Neue Reaktionen mit Nitrosouracilderivaten,II[1)] Synthese von 8H-Xanthinen, 8H-Xanthin-7-N-oxiden und 3H-Pyrimido[5,4-c]-1.2.5-oxadiazinen," Justus Liebigs Annalen Der Chemie, (Apr. 1966) 692(1):134-150, XP055134233.

National Institute of Allergy and Infectious Diseases—Division of AIDS Anti-HIV/OI/TB Therapeutics Database—Details Page, "AIDS#: 147565," Last Updated: Apr. 2014 (2 pages).

Saeki et al., "Selective Block of Delayed Rectifying Potassium Current in the Rabbit Sinoatrial Node by a Novel Class III Antiarrhythmic Agent MS-551," *Heart Vessels* (1994; Accepted Aug. 20, 1993) 9:87-95.

International Preliminary Report on Patentability corresponding to PCT/US2014/043192 mailed Dec. 30, 2015, 8 pages.

Press Release: "MyoKardia Receives Orphan Drug Designation for MYK-461 for Treatment of Symptomatic Obstructive Hypertrophic Cardiomyopathy (oHCM)." (May 2, 2016); 3 pages.

Press Release: "MyoKardia Announces Topline Clinical Data Supporting Advancement of MYK-461 to Phase 2 PIONEER-HCM Study in Symptomatic, Obstructive Hypertrophic Cardiomyopathy Patients." (Jul. 11, 2016); 5 pages.

Press Release: "MyoKardia Outlines Path to Registration for MYK-461 in Symptomatic, Obstructive Hypertrophic Cardiomyopathy Patients and Provides Pipeline and Research Updates at Inaugural R&D Day." (Sep. 21, 2016); 5 pages.

Data Supplement to Press Release: "MyoKardia Announces Topline Clinical Data Supporting Advancement of MYK-461 to Phase 2 PIONEER-HCM Study in Symptomatic, Obstructive Hypertrophic Cardiomyopathy Patients." (Jul. 11, 2016); 10 pages.

Presentation: "Welcome to R & D Day Vision 2020," MyoKardia (Sep. 21, 2016); 104 pages.

Green, Eric M. et al., "A small-moleculate inhibitor of sarcomere contractility suppresses hypertrophic cardiomyopathy in mice," *Science* (Feb. 5, 2016); 351(6273):617-621.

Ghermazien, Haben T. et al., "Cardiac Selective Modulator of Human Myosin for the Treatment of Genetic Hypertrophic Cardiomyopathy." Scientific Poster (circa 2014); 1 page.

Rodriguez, H. M. et al., "Modulation of the cardiac sarcomere by a small molecule agent MYK0000461: A potential therapeutic for the treatment of genetic hypertrophic cardiomyopathies." Scientific Poster (circa 2014); 1 page.

Form S-1 Registration Statement for MyoKardia, Inc., Registration No. 333 as filed with the Securities and Exchange Commission on Sep. 16, 2016, 104 pages.

Amendment No. 1 to Form S-1 Registration Statement for MyoKardia, Inc., Registration No. 333-213680 as filed with the Securities and Exchange Commission on Sep. 26, 2016, 137 pages.

* cited by examiner

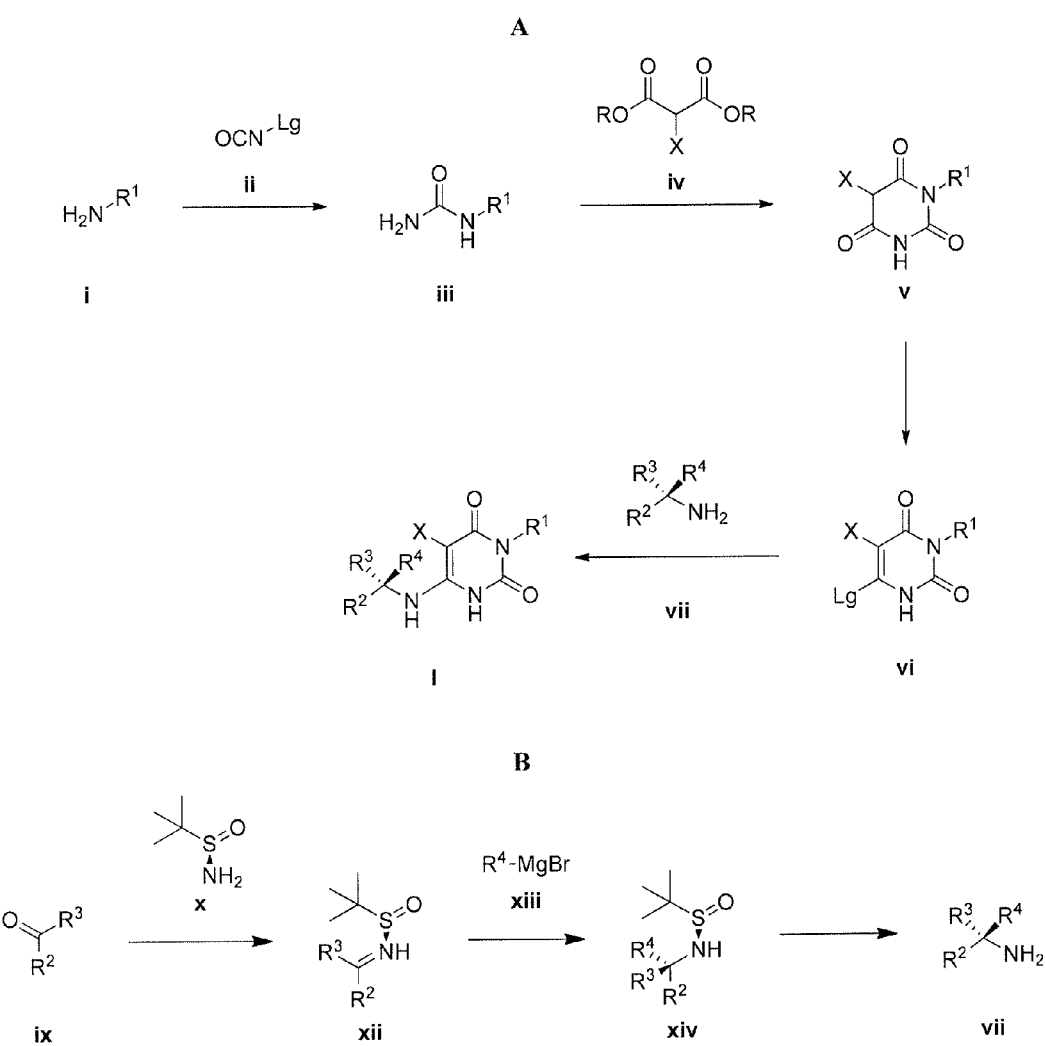

PYRIMIDINEDIONE COMPOUNDS

CROSS-REFERENCES TO RELATED APPLICATIONS

This application is a divisional of U.S. application Ser. No. 14/309,381 filed Jun. 19, 2014, which claims benefit under 35 U.S.C. §119(e) of U.S. Provisional Application No. 61/838,088 filed Jun. 21, 2013, and U.S. Provisional Application No. 61/939,655 filed Feb. 13, 2014, and U.S. Provisional Application No. 61/981,366 filed Apr. 18, 2014, each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Genetic (heritable) hypertrophic cardiomyopathy (HCM) comprises a group of highly penetrant, monogenic, autosomal dominant myocardial diseases. HCM is caused by one or more of over 1,000 known point mutations in any one of the structural protein genes contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, once other heritable (e.g., lysosomal storage diseases), metabolic, or infiltrative causes have been excluded.

Sarcomere gene mutations that cause HCM are highly penetrant, but there is wide variability in clinical severity and clinical course. Some genotypes are associated with a more malignant course, but there is considerable variability between and even within families carrying the same mutation. Sex differences have also been noted, with male patients generally more severely affected than female patients. While many patients with HCM report minimal or no symptoms for extended periods of time, HCM is a progressive disease with a significant cumulative burden of morbidity. Symptoms of effort intolerance predominate, and can be exacerbated by exercise and other maneuvers that increase heart rate and/or decrease preload. As with many other disorders, symptoms tend to worsen with age. By far the most prevalent clinical burden for patients with HCM is exertional dyspnea, which limits their activities of daily living and can be debilitating.

Patients with HCM are often symptomatic in the absence of documented hemodynamic abnormalities like left ventricular outflow tract obstruction (with or without mitral regurgitation). Patients' symptoms of exertional dyspnea can rapidly worsen with the onset of atrial fibrillation, a common complication of HCM that can precipitate acute pulmonary edema that increases the risk of systemic arterial thromboembolic disease, including stroke. Other adverse events associated with HCM include intolerance of hypovolemia or hypervolemia, and syncope. Concomitant coronary artery disease may confer a higher risk of acute coronary syndromes than in patients without HCM. Sudden cardiac death (SCD) in patients with HCM is both uncommon and difficult to predict but is a leading cause of non-traumatic death in young adults. For survivors of SCD, ICD placement is standard practice, and in other HCM patients risk profiling, while imprecise, is used to identify those for whom ICD placement for primary prevention is deemed prudent.

Medical therapy for HCM is limited to the treatment of symptoms and does not address the fundamental, underlying cause of disease—disruptions in normal sarcomere function. Currently available therapies are variably effective in alleviating symptoms but typically show decreased efficacy with increasing disease duration. Patients are thus empirically managed with beta-blockers, non-dihydropyridine calcium channel blockers, and/or disopyramide. None of these agents carry labeled indications for treating HCM, and essentially no rigorous clinical trial evidence is available to guide their use. Compounding this unfortunate situation is the fact that no new medical therapies for HCM have been identified for many years. For patients with hemodynamically significant outflow tract obstruction (resting gradient>30 mmHg), in appropriately selected patients surgical myectomy or alcohol septal ablation is usually required to alleviate the hemodynamic obstruction. Provided are new therapeutic agents and methods that remedy the long-felt need for improved treatment of HCM and related cardiac disorders.

BRIEF SUMMARY OF THE INVENTION

In one aspect, provided is a compound having the formula:

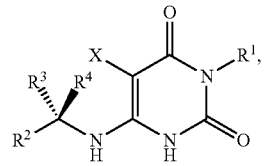

or a pharmaceutically acceptable salt thereof. In some embodiments, the above formula, $R^1$ is a member selected from $C_1$-$C_8$ alkyl, $C_3$-$C_8$ cycloalkyl, $C_3$-$C_8$ cycloalkyl-$C_1$-$C_4$ alkyl, 4- to 7-membered heterocycloalkyl, phenyl, phenyl-$C_1$-$C_4$ alkyl, 5- to 6-membered heteroaryl and 5- to 6-membered heteroaryl-$C_1$-$C_4$ alkyl, wherein each $R^1$ is optionally substituted with from 1-3 $R^a$; $R^2$ is a member selected from phenyl, phenyl-$C_1$-$C_4$ alkyl, 5- to 6-membered heteroaryl and 5- to 6-membered heteroaryl-$C_1$-$C_4$ alkyl, wherein each $R^2$ is optionally substituted with from 1-5 $R^b$; $R^3$ is a member selected from $C_1$-$C_4$ alkyl, $C_3$-$C_4$ cycloalkyl, and 4- to 7-membered heterocycloalkyl wherein each $R^3$ is optionally substituted with from 1-3 $R^c$; $R^4$ is H; X is a member selected from H and halo, and in some embodiments X is selected from H and F. Each $R^a$, when present, is independently selected from halo, CN, hydroxyl, $C_1$-$C_4$ alkyl, $C_1$-$C_4$ haloalkyl, $C_1$-$C_4$ alkoxy, phenyl, phenyl-$C_1$-$C_4$ alkyl, phenyl-$C_1$-$C_4$ alkoxy, phenoxy, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from H, $C_1$-$C_4$ alkyl and phenyl, or optionally $R^{a1}$ and $R^{a2}$ when attached to a nitrogen atom are combined to form a 4- to 6-membered ring. Similarly, each $R^b$, when present, is independently selected from halo, CN, hydroxyl, $C_1$-$C_4$ alkyl, $C_1$-$C_4$ haloalkyl, $C_1$-$C_4$ alkoxy, phenoxy, phenyl-$C_1$-$C_4$ alkoxy, methylenedioxy, difluoromethylenedioxy, —$COR^{b1}$, —$CO_2R^{b1}$, —$SO_2R^{b1}$, —$SO_2NR^{b1}R^{b2}$, $CONR^{b1}R^{b2}$, $NR^{b1}R^{b2}$, 5- to 6-membered heteroaryl, and 5- to 6-membered heterocyclyl optionally substituted with oxo, wherein each $R^{b1}$ and $R^{b2}$ is independently selected from H and $C_1$-$C_4$ alkyl or optionally $R^{b1}$ and $R^{b2}$ when attached to a nitrogen atom are combined to form a 4- to 6-membered ring; and each $R^c$, when present, is independently selected from halo, hydroxyl and $C_1$-$C_2$ alkoxy.

In another aspect, provided is a pharmaceutical composition containing a compound or or pharmaceutically acceptable salt described herein and a pharmaceutically acceptable excipient.

In another aspect, provided is a method of treating hypertrophic cardiomyopathy (HCM) or a cardiac disorder having one or more pathophysiological features associated with HCM. The method includes administering to a subject in need thereof an effective amount of a compound or pharmaceutically acceptable salt described herein.

BRIEF DESCRIPTION OF THE DRAWINGS

FIG. 1 shows a schematic route for the synthesis of the compounds or pharmaceutically acceptable salts described herein (FIG. 1A) and a route for the preparation of chiral amines (FIG. 1B).

DETAILED DESCRIPTION OF THE INVENTION

I. General

A series of pyrimidine dione compounds and pharmaceutically acceptable salts thereof has been found to reduce excess contractility in hypercontractile states and/or promote cardiac relaxation in hearts with diastolic dysfunction by stabilizing the conformation of beta cardiac myosin post-ATP hydrolysis but prior to strongly binding the actin filament and releasing phosphate, thus reducing the proportion of myosin molecules that are available to participate in the "powerstroke" portion of the muscle contraction cycle. As such, the compounds can improve cardiac elasticity, reduce dynamic and/or static left ventricular outflow obstruction, improve diastolic left ventricular relaxation, reduce left ventricular diastolic (filling) pressures, reduce functional mitral regurgitation, and/or reduce left atrial and pulmonary capillary wedge pressures in patients with HCM helping overcome the debilitating exertional dyspnea and/or symptoms referable to left ventricular outflow obstruction (presyncope or syncope) that often accompanies the disease. The compounds can also be used to treat other cardiac disorders.

II. Definitions

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Unless stated otherwise, alkyl groups are unsubstituted. A "substituted alkyl" group can be substituted with one or more moieties selected from halo, hydroxy, amino, alkylamino, nitro, cyano, and alkoxy.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

As used herein, the term "heterocycloalkyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocycloalkyl groups can include any number of ring atoms, such as, 3 to 6, 4 to 6, 5 to 6, or 4 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Examples of heterocycloalkyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocycloalkyl groups are unsubstituted, but can be described, in some embodiments as substituted. "Substituted heterocycloalkyl" groups can be substituted with one or more moieties selected from halo, hydroxy, amino, alkylamino, nitro, cyano, and alkoxy.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2, 3-, 1,2,4- and 1,3,5-isomers), thiophene, furan, thiazole, isothiazole, oxazole, and isoxazole. Heteroaryl groups are unsubstituted, but can be described, in some embodiments as substituted. "Substituted heteroaryl" groups can be substituted with one or more moieties selected from halo, hydroxy, amino, alkylamino, nitro, cyano, and alkoxy.

As used herein, the term "alkoxy" refers to an alkyl group having an oxygen atom that connects the alkyl group to the point of attachment: i.e., alkyl-O—. As for the alkyl portion, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups are unsubstituted, but can be described, in some embodiments as substituted. "Substituted alkoxy" groups can be substituted with one or more moieties selected from halo, hydroxy, amino, alkylamino, nitro, cyano, and alkoxy.

As used herein, the terms "halo" and "halogen" refer to fluorine, chlorine, bromine and iodine.

As used herein, the term "pharmaceutically acceptable" refers to a substance that is compatible with a compound or salt as described herein, as well as with any other ingredients with which the compound is formulated. Furthermore, a pharmaceutically acceptable substance is not deleterious to the recipient of the substance.

As used herein, the term "salt" refers to an acid or base salt of a compound described herein. Pharmaceutically acceptable salts can be derived, for example, from mineral acids (hydrochloric acid, hydrobromic acid, phosphoric acid, and the like), organic acids (acetic acid, propionic acid, glutamic acid, citric acid and the like), and quaternary ammonium ions. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference. The neutral form of a compound may be regenerated by contacting the salt with a base or acid and isolating the parent compound in the conventional manner.

As used herein, the term "pharmaceutical composition" refers to a product comprising a compound or pharmaceutically acceptable salt described herein, an excipient as defined herein, and other optional ingredients in specified amounts, as well as any product which results directly or indirectly from combination of the specified ingredients in the specified amounts.

As used herein, the term "excipient" refers to a substance that aids the administration of an active agent to a subject. Pharmaceutical excipients include, but are not limited to, binders, fillers, disintegrants, lubricants, coatings, sweeteners, flavors and colors. One of skill in the art will recognize that other excipients can be useful.

As used herein, the terms "treat," "treating" and "treatment" refer to any indicia of success in the treatment or amelioration of a pathology, injury, condition, or symptom related to hypertrophic cardiomyopathy, including any objective or subjective parameter such as abatement; remission; diminishing of symptoms; making the pathology, injury, condition, or symptom more tolerable to the patient; decreasing the frequency or duration of the pathology, injury, condition, or symptom; or, in some situations, preventing the onset of the pathology, injury, condition, or symptom. Treatment or amelioration can be based on any objective or subjective parameter; including, e.g., the result of a physical examination.

III. Compounds and Pharmaceutically Acceptable Salts Thereof

In one aspect, provided is a compound having the formula:

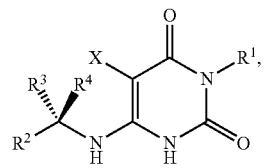

or a pharmaceutically acceptable salt thereof.

In the above formula, $R^1$ is a member selected from $C_1$-$C_8$ alkyl, $C_3$-$C_8$ cycloalkyl, $C_3$-$C_8$ cycloalkyl-$C_1$-$C_4$ alkyl, 4- to 7-membered heterocycloalkyl, phenyl, phenyl-$C_1$-$C_4$ alkyl, 5- to 6-membered heteroaryl and 5- to 6-membered heteroaryl-$C_1$-$C_4$ alkyl, wherein each $R^1$ is optionally substituted with from 1-3 $R^a$; $R^2$ is a member selected from phenyl, phenyl-$C_1$-$C_4$ alkyl, 5- to 6-membered heteroaryl and 5- to 6-membered heteroaryl-$C_1$-$C_4$ alkyl, wherein each $R^2$ is optionally substituted with from 1-5 $R^b$; $R^3$ is a member selected from $C_1$-$C_4$ alkyl, $C_3$-$C_4$ cycloalkyl, and 4- to 7-membered heterocycloalkyl wherein each $R^3$ is optionally substituted with from 1-3 $R^c$; $R^4$ is H; X is a member selected from H and halo, and in selected embodiments, is selected from H and F. Each $R^a$, when present, is independently selected from halo, CN, hydroxyl, $C_1$-$C_4$ alkyl, $C_1$-$C_4$ haloalkyl, $C_1$-$C_4$ alkoxy, phenyl, phenyl-$C_1$-$C_4$ alkyl, phenyl-$C_1$-$C_4$ alkoxy, phenoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from H, $C_1$-$C_4$ alkyl and phenyl, or optionally $R^{a1}$ and $R^{a2}$ when attached to a nitrogen atom are combined to form a 4- to 6-membered ring. Similarly, each $R^b$, when present, is independently selected from halo, CN, hydroxyl, $C_1$-$C_4$ alkyl, $C_1$-$C_4$ haloalkyl, $C_1$-$C_4$ alkoxy, phenoxy, phenyl-$C_1$-$C_4$ alkoxy, methylenedioxy, difluoromethylenedioxy, —$COR^{b1}$, —$CO_2R^{b1}$, —$SO_2R^{b1}$, —$SO_2NR^{b1}R^{b2}$, $CONR^{b1}R^{b2}$, $NR^{b1}R^{b2}$, 5- to 6-membered heteroaryl, and 5- to 6-membered heterocyclyl optionally substituted with oxo, wherein each $R^{b1}$ and $R^{b2}$ is independently selected from H and $C_1$-$C_4$ alkyl or optionally $R^{b1}$ and $R^{b2}$ when attached to a nitrogen atom are combined to form a 4- to 6-membered ring; and each $R^c$, when present, is independently selected from halo, hydroxyl and $C_1$-$C_2$ alkoxy.

In some embodiments, $R^1$ is selected from $C_1$-$C_8$ alkyl, $C_3$-$C_8$ cycloalkyl, 4- to 7-membered heterocycloalkyl, phenyl, or 5- to 6-membered heteroaryl, wherein each $R^1$ is optionally substituted with from 1-3 $R^a$. $R^2$ is phenyl, which is optionally substituted with from 1-5 $R^b$. $R^3$ is selected from $C_1$-$C_4$ alkyl, $C_3$-$C_4$ cycloalkyl, or 4- to 7-membered heterocycloalkyl, wherein each $R^3$ is optionally substituted with from 1-2 $R^c$. $R^4$ is H, and X is H or F. In some embodiments, each $R^a$, when present, is independently halo, CN, $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, or —$CONR^{a1}R^{a2}$, wherein each $R^{a1}$ and $R^{a2}$ is independently H or $C_1$-$C_4$ alkyl. Alternatively, $R^{a1}$ and $R^{a2}$, when attached to a nitrogen atom, are optionally combined to form a 4- to 6-membered ring. Each $R^b$, when present, is independently halo, CN, $C_1$-$C_4$ alkyl, $C_1$-$C_4$ alkoxy, —$COR^{b1}$, —$CO_2R^{b1}$, —$SO_2R^{b1}$, —$SO_2NR^{b1}R^{b2}$, $CONR^{b1}R^{b2}$, $NR^{b1}R^{b2}$, 5- to 6-membered heteroaryl, or 5- to 6-membered heterocyclyl optionally substituted with oxo, wherein each $R^{b1}$ and $R^{b2}$ is independently H or $C_1$-$C_4$ alkyl. Alternatively, $R^{b1}$ and $R^{b2}$, when attached to a nitrogen atom, are optionally combined to form a 4- to 6-membered ring. Each $R^c$, when present, is independently halo or $C_1$-$C_2$ alkoxy.

In some embodiments, X is H.

In some embodiments, $R^1$ is $C_3$-$C_4$ alkyl, $C_3$-$C_5$ cycloalkyl, or 4- to 6-membered heterocycloalkyl, wherein each $R^1$ is optionally substituted with from 1-2 $R^a$.

In some embodiments, $R^1$ is phenyl or 5- to 6-membered heteroaryl, wherein each $R^1$ is optionally substituted with from 1-3 $R^a$.

In some embodiments, $R^1$ is $C_3$-$C_4$ alkyl, $C_3$-$C_5$ cycloalkyl, or 4- to 6-membered heterocycloalkyl.

In some embodiments, $R^1$ is 4- to 6-membered heterocycloalkyl, optionally substituted with from 1-2 $R^a$ selected from $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently H or $C_1$-$C_4$ alkyl.

In some embodiments, $R^1$ is cyclobutyl, isopropyl, isobutyl, 1-methoxypropan-2-yl, cyclopentyl, cyclohexyl, 4-tetrahydropyranyl, 1-(methylsulfonyl)piperidin-4-yl, 1-(methoxycarbonyl)piperidin-4-yl, 4,4-difluorocyclohexyl, phenyl, 2-pyridyl, 3-pyridyl, 3-isoxazolyl, 5-isoxazolyl, or 1-methyl-3-pyrazolyl.

In some embodiments, $R^2$ is optionally substituted with from 1-2 $R^b$.

In some embodiments, $R^2$ is phenyl, 3-methylphenyl, 2-fluorophenyl, 3-fluorophenyl, 4-fluorophenyl, 2,5-difluorophenyl, 3,5-chlorophenyl, 3-chlorophenyl, 3-methoxyphenyl, 3-(3-oxazolidin-2-onyl)phenyl, 3-(2-methyl-1-imidazyl)phenyl, 3-(1-pyrazolyl)phenyl, or 3-(1,2,4-triazol-1-yl)phenyl.

In some embodiments, $R^3$ is $C_1$-$C_4$ alkyl, $C_1$-$C_4$ alkoxyalkyl, or $C_3$-$C_4$ cycloalkyl.

In some embodiments, $R^3$ is methyl, ethyl, propyl, cyclopropyl, cyclobutyl or 2-methoxymethyl.

In some embodiments, $R^3$ is methyl.

The compounds or pharmaceutically acceptable salts described herein can have any combination of the $R^1$, $R^2$, $R^3$, $R^4$, $R^a$, $R^{a1}$, $R^{a2}$, $R^b$, $R^{b1}$, $R^{b2}$, $R^c$, and X groups recited above. Selected embodiments recited for $R^2$, for example, can be combined with any of the selected embodiments recited for $R^1$ which, in turn, can be combined with any of the selected embodiments recited for $R^3$.

In some embodiments, for example, $R^1$ is $C_3$-$C_8$ alkyl; $R^3$ is $C_3$-$C_4$ cycloalkyl or 4- to 7-membered heterocycloalkyl; and $R^2$ is phenyl. In other embodiments, $R^1$ is 4- to 7-membered heterocycloalkyl or 5- to 6-membered heteroaryl which is optionally substituted with $C_1$-$C_4$ alkyl, —$CO_2R^{a1}$, —$SO_2NR^{a1}R^{a2}$, or —$SO_2R^{a1}$; $R^3$ is $C_3$-$C_4$ cycloalkyl or 4- to 7-membered heterocycloalkyl; and $R^2$ is phenyl. In still other embodiments, $R^1$ is $C_3$-$C_8$ cycloalkyl or phenyl, $R^3$ is $C_3$-$C_4$ cycloalkyl or 4- to 7-membered heterocycloalkyl; and $R^2$ is phenyl.

In other embodiments, $R^1$ is $C_3$-$C_8$ alkyl; $R^3$ is $C_1$-$C_4$ alkyl; and $R^2$ is phenyl. In yet other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_1$-$C_4$ alkyl; and $R^2$ is phenyl. In still other embodiments, $R^1$ is $C_3$-$C_8$ cycloalkyl or phenyl; $R^3$ is $C_1$-$C_4$ alkyl; and $R^2$ is phenyl.

In some embodiments, $R^1$ is $C_3$-$C_8$ alkyl; $R^3$ is $C_3$-$C_4$ cycloalkyl or 4- to 7-membered heterocycloalkyl; and $R^2$ is phenyl substituted with 1-2 $C_1$-$C_4$ alkoxy or halo. In still other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_3$-$C_4$ cycloalkyl or 4- to 7-membered heterocycloalkyl; and $R^2$ is phenyl substituted with 1-2 $C_1$-$C_4$ alkoxy or halo. In yet other embodiments, $R^1$ is $C_3$-$C_8$ cycloalkyl or phenyl; $R^3$ is $C_3$-$C_4$ cycloalkyl or 4- to 7-membered heterocycloalkyl; and $R^2$ is phenyl substituted with 1-2 $C_1$-$C_4$ alkoxy or halo.

In some embodiments, $R^1$ is $C_3$-$C_8$ alkyl; $R^3$ is $C_1$-$C_4$ alkyl; and $R^2$ is phenyl substituted with 1-2 $C_1$-$C_4$ alkoxy or halo. In other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_1$-$C_4$ alkyl; and $R^2$ is phenyl substituted with 1-2 $C_1$-$C_4$ alkoxy or halo. In other embodiments, $R^1$ is $C_3$-$C_8$ cycloalkyl or phenyl; $R^3$ is $C_1$-$C_4$ alkyl; and $R^2$ is phenyl substituted with 1-2 $C_1$-$C_4$ alkoxy or halo.

In some embodiments, $R^1$ is $C_3$-$C_8$ alkyl; $R^3$ is $C_3$-$C_4$ cycloalkyl or 4- to 7-membered heterocycloalkyl; and $R^2$ is phenyl substituted with 5- to 6-membered heteroaryl or 5- to 6-membered heterocyclyl optionally substituted with oxo. In other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_3$-$C_4$ cycloalkyl or 4- to 7-membered heterocycloalkyl; and $R^2$ is phenyl substituted with 5- to 6-membered heteroaryl or 5- to 6-membered heterocyclyl optionally substituted with oxo. In other embodiments, $R^1$ is $C_3$-$C_8$ cycloalkyl or phenyl, $R^3$ is $C_3$-$C_4$ cycloalkyl or 4- to 7-membered heterocycloalkyl; and $R^2$ is phenyl substituted with 5- to 6-membered heteroaryl or 5- to 6-membered heterocyclyl optionally substituted with oxo.

In some embodiments, $R^1$ is $C_3$-$C_8$ alkyl; $R^3$ is $C_1$-$C_4$ alkyl; and $R^2$ is phenyl substituted with 5- to 6-membered heteroaryl or 5- to 6-membered heterocyclyl optionally substituted with oxo. In other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_1$-$C_4$ alkyl; and $R^2$ is phenyl substituted with 5- to 6-membered heteroaryl or 5- to 6-membered heterocyclyl optionally substituted with oxo. In other embodiments, $R^1$ is $C_3$-$C_8$ cycloalkyl or phenyl; $R^3$ is $C_1$-$C_4$ alkyl; and $R^2$ is phenyl substituted with 5- to 6-membered heteroaryl or 5- to 6-membered heterocyclyl optionally substituted with oxo.

In some embodiments, $R^1$ is $C_3$-$C_8$ alkyl; $R^3$ is $C_3$-$C_4$ cycloalkyl or 4- to 7-membered heterocycloalkyl; and $R^2$ is phenyl substituted with CN, alkyl, —$COR^{b1}$, —$CO_2R^{b1}$, —$SO_2R^{b1}$, —$SO_2NR^{b1}R^{b2}$, $CONR^{b1}R^{b2}$, or $NR^{b1}R^{b2}$. In other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_3$-$C_4$ cycloalkyl or 4- to 7-membered heterocycloalkyl; and $R^2$ is phenyl substituted with CN, $C_1$-$C_4$ alkyl, —$COR^{b1}$, —$CO_2R^{b1}$, —$SO_2R^{b1}$, $CONR^{b1}R^{b2}$, or $NR^{b1}R^{b2}$. In other embodiments, $R^1$ is $C_3$-$C_8$ cycloalkyl or phenyl; $R^3$ is $C_3$-$C_4$ cycloalkyl or 4- to 7-membered heterocycloalkyl; and $R^2$ is phenyl substituted with CN, $C_1$-$C_4$ alkyl, —$COR^{b1}$, —$CO_2R^{b1}$, —$SO_2R^{b1}$, $CONR^{b1}R^{b2}$, or $NR^{b1}R^{b2}$.

In some embodiments, $R^1$ is $C_3$-$C_8$ alkyl; $R^3$ is $C_1$-$C_4$ alkyl; and $R^2$ is phenyl substituted with CN, $C_1$-$C_4$ alkyl, —$COR^{b1}$, —$CO_2R^{b1}$, $CONR^{b1}R^{b2}$, or $NR^{b1}R^{b2}$. In other embodiments, $R^1$ is 4- to 7-membered heterocycloalkyl or 5- to 6-membered heteroaryl which is optionally substituted with $C_1$-$C_4$ alkyl, —$CO_2R^{a1}$, or —$SO_2R^{a1}$; $R^3$ is $C_1$-$C_4$ alkyl; and $R^2$ is phenyl substituted with CN, $C_1$-$C_4$ alkyl, —$COR^{b1}$, —$CO_2R^{b1}$, —$SO_2R^{b1}$, $CONR^{b1}R^{b2}$, or $NR^{b1}R^{b2}$. In other embodiments, $R^1$ is $C_3$-$C_8$ cycloalkyl or phenyl; $R^3$ is $C_1$-$C_4$ alkyl; and $R^2$ is phenyl substituted with CN, $C_1$-$C_4$ alkyl, —$COR^{b1}$, —$CO_2R^{b1}$, —$SO_2R^{b1}$, $CONR^{b1}R^{b2}$, $NR^{b1}R^{b2}$, or —$CONR^{a1}R^{a2}$.

In some embodiments, $R^1$ is isopropyl; $R^2$ is optionally substituted with 1-2 $R^b$; and $R^3$ is methyl.

In some embodiments, $R^1$ is 4- to 6-membered heterocycloalkyl, optionally substituted with from 1-2 $R^a$ selected from $C_1$-$C_4$ alkyl, $C_1$-$C_4$ alkoxy, —$CO_2R^{a1}$, —$SO_2R^{a1}$, —$SO_2NR^{a1}R^2$, and —$CONR^{a1}R^{a2}$, wherein each $R^{a1}$ and $R^{a2}$ can independently be H or $C_1$-$C_4$ alkyl; $R^2$ is optionally substituted with 1-2 $R^b$; and $R^3$ is methyl.

In some embodiments, $R^1$ is phenyl or 5- to 6-membered heteroaryl, wherein each $R^1$ is optionally substituted with from 1-3 $R^a$; $R^2$ is optionally substituted with from 1-2 $R^b$; and $R^3$ is methyl.

X can be H in any of the embodiments set forth above. In other embodiments, X can be F in any of the embodiments set forth above. Still further, compounds provided herein with an identified stereochemistry (indicated as R or S, or with dashed or wedge bond designations) will be understood by one of skill in the art to be substantially free of other isomers (e.g., at least 80%, 90%, 95% up to 100% free of the other isomer).

In some embodiments, the compound is selected from:
(S)-3-isopropyl-6-((1-phenylethyl)amino)pyrimidine-2,4 (1H,3H)-dione;
(S)-5-fluoro-3-isopropyl-6-((1-phenylethyl)amino)pyrimidine-2,4(1H,3H)-dione;
(S)-5-bromo-3-isopropyl-6-((1-phenylethyl)amino)pyrimidine-2,4(1H,3H)-dione;
(S)-6-((1-(3-chlorophenyl)ethyl)amino)-5-fluoro-3-isopropylpyrimidine-2,4(1H,3H)-dione;
(S)-6-((1-(3,5-difluorophenyl)ethyl)amino)-3-isopropylpyrimidine-2,4(1H,3H)-dione;
(S)-6-((cyclopropyl(phenyl)methyl)amino)-3-isopropylpyrimidine-2,4(1H,3H)-dione;
(S)-6-((cyclopropyl(3-methoxyphenyl)methyl)amino)-3-isopropylpyrimidine-2,4(1H,3H)-dione;
(S)-6-((cyclobutyl(phenyl)methyl)amino)-3-isopropylpyrimidine-2,4(1H,3H)-dione;
(S)-6-((1-(3-fluorophenyl)ethyl)amino)-3-(tetrahydro-2H-pyran-4-yl)pyrimidine-2,4(1H,3H)-dione;
(S)-6-((1-(3-methoxyphenyl)ethyl)amino)-3-(tetrahydro-2H-pyran-4-yl)pyrimidine-2,4(1H,3H)-dione;
6-(((S)-1-phenylethyl)amino)-3-(tetrahydrofuran-3-yl)pyrimidine-2,4(1H,3H)-dione;
(S)-3-(1-(methylsulfonyl)piperidin-4-yl)-6-((1-phenylethyl)amino)pyrimidine-2,4(1H,3H)-dione;
methyl (S)-4-(2,6-dioxo-4-((1-phenylethyl)amino)-3,6-dihydropyrimidin-1(2H)-yl)piperidine-1-carboxylate;
3-((R)-sec-butyl)-6-(((S)-1-(3-methoxyphenyl)ethyl)amino) pyrimidine-2,4(1H,3H)-dione;
(S)-6-((1-phenylethyl)amino)-3-(pyridin-3-yl)pyrimidine-2,4(1H,3H)-dione;
(S)-3-(isoxazol-3-yl)-6-((1-phenylethyl)amino)pyrimidine-2,4(1H,3H)-dione;
(S)-6-((1-(3-(1H-pyrazol-1-yl)phenyl)ethyl)amino)-3-isopropylpyrimidine-2,4(1H,3H)-dione;
(S)-3-isopropyl-6-((1-(3-methoxyphenyl)ethyl)amino)pyrimidine-2,4(1H,3H)-dione;
(S)-3-isopropyl-6-((1-(2-methoxyphenyl)ethyl)amino)pyrimidine-2,4(1H,3H)-dione;
(S)-3-isopropyl-6-((1-phenylpropyl)amino)pyrimidine-2,4 (1H,3H)-dione;
(S)-3-isopropyl-5-methyl-6-((1-phenylethyl)amino)pyrimidine-2,4(1H,3H)-dione;
(S)-6-((1-(2-fluorophenyl)ethyl)amino)-3-isopropylpyrimidine-2,4(1H,3H)-dione;
(S)-6-((1-(3-fluorophenyl)ethyl)amino)-3-isopropylpyrimidine-2,4(1H,3H)-dione;
(S)-6-((1-(3-chlorophenyl)ethyl)amino)-3-isopropylpyrimidine-2,4(1H,3H)-dione;
(S)-6-((1-(4-fluorophenyl)ethyl)amino)-3-isopropylpyrimidine-2,4(1H,3H)-dione;
(S)-5-fluoro-3-isopropyl-6-((1-phenylpropyl)amino)pyrimidine-2,4(1H,3H)-dione;
(S)-5-fluoro-6-((1-(3-fluorophenyl)ethyl)amino)-3-isopropylpyrimidine-2,4(1H,3H)-dione;
(S)-5-fluoro-3-isopropyl-6-((1-(3-methoxyphenyl)ethyl) amino)pyrimidine-2,4(1H,3H)-dione;
(S)-6-((1-(2,5-difluorophenyl)ethyl)amino)-3-isopropylpyrimidine-2,4(1H,3H)-dione;
(S)-6-((1-(3-bromophenyl)ethyl)amino)-3-isopropylpyrimidine-2,4(1H,3H)-dione;
(S)-3-ethyl-6-((1-phenylpropyl)amino)pyrimidine-2,4(1H, 3H)-dione;
(S)-3-cyclopropyl-6-((1-phenylethyl)amino)pyrimidine-2,4 (1H,3H)-dione;
(S)-6-((1-phenylethyl)amino)-3-(pyridin-2-yl)pyrimidine-2,4(1H,3H)-dione;
(S)-3-(1-methyl-1H-pyrazol-3-yl)-6-((1-phenylethyl) amino)pyrimidine-2,4(1H,3H)-dione;
(S)-3-(isoxazol-5-yl)-6-((1-phenylethyl)amino)pyrimidine-2,4(1H,3H)-dione;
(S)-6-((1-(3-(1H-1,2,4-triazol-1-yl)phenyl)ethyl)amino)-3-isopropylpyrimidine-2,4(1H,3H)-dione;
(S)-3-isopropyl-6-((1-(3-(2-methyl-1H-imidazol-1-yl)phenyl)ethyl)amino)pyrimidine-2,4(1H,3H)-dione;
(S)-3-isopropyl-6-((1-(3-(2-oxooxazolidin-3-yl)phenyl) ethyl)amino)pyrimidine-2,4(1H,3H)-dione;
(S)-3-cyclohexyl-6-((1-phenylethyl)amino)pyrimidine-2,4 (1H,3H)-dione;
(S)-3-phenyl-6-((1-phenylethyl)amino)pyrimidine-2,4(1H, 3H)-dione;
(S)-3-ethyl-6-((1-phenylethyl)amino)pyrimidine-2,4(1H, 3H)-dione;
(S)-3-methyl-6-((1-phenylethyl)amino)pyrimidine-2,4(1H, 3H)-dione;
(S)-6-((1-phenylethyl)amino)-3-propylpyrimidine-2,4(1H, 3H)-dione;
(S)-3-(3,5-difluorophenyl)-6-((1-phenylethyl)amino)pyrimidine-2,4(1H,3H)-dione;
(S)-3-isopropyl-6-((1-(m-tolyl)ethyl)amino)pyrimidine-2,4 (1H,3H)-dione;
(S)-6-((1-(4-fluorophenyl)propan-2-yl)amino)-3-isopropylpyrimidine-2,4(1H,3H)-dione;
(R)-3-isopropyl-6-((2,2,2-trifluoro-1-phenylethyl)amino) pyrimidine-2,4(1H,3H)-dione;
3-((R)-1-(benzyloxy)propan-2-yl)-6-(((S)-1-phenylethyl) amino)pyrimidine-2,4(1H,3H)-dione;
3-((R)-1-hydroxypropan-2-yl)-6-(((S)-1-phenylethyl) amino)pyrimidine-2,4(1H,3H)-dione;
(S)-3-isopropyl-6-((1-(3-(trifluoromethyl)phenyl)ethyl) amino)pyrimidine-2,4(1H,3H)-dione;
(S)-2-(1-((1-isopropyl-2,6-dioxo-1,2,3,6-tetrahydropyrimidin-4-yl)amino)ethyl)benzonitrile
(S)-3-benzyl-6-((1-phenylethyl)amino)pyrimidine-2,4(1H, 3H)-dione;
(S)-3-(2,6-difluorophenyl)-6-((1-phenylethyl)amino)pyrimidine-2,4(1H,3H)-dione;
(S)-6-((1-(2,6-difluorophenyl)ethyl)amino)-3-isopropylpyrimidine-2,4(1H,3H)-dione;
(S)-3-isopropyl-6-((1-(pyridin-4-yl)propan-2-yl)amino)pyrimidine-2,4(1H,3H)-dione;
(S)-6-((1-(4-(benzyloxy)phenyl)ethyl)amino)-3-isopropylpyrimidine-2,4(1H,3H)-dione;
(S)-6-((1-(4-hydroxyphenyl)ethyl)amino)-3-isopropylpyrimidine-2,4(1H,3H)-dione;
(R)-6-((2-(benzyloxy)-1-phenylethyl)amino)-3-isopropylpyrimidine-2,4(1H,3H)-dione;

(S)-3-(6-methylpyridin-2-yl)-6-((1-phenylethyl)amino)pyrimidine-2,4(1H,3H)-dione;
(S)-3-(2,2-difluoroethyl)-6-((1-phenylethyl)amino)pyrimidine-2,4(1H,3H)-dione;
(S)-6-((1-(benzo[d][1,3]dioxol-5-yl)ethyl)amino)-3-(2,2,2-trifluoroethyl)pyrimidine-2,4(1H,3H)-dione;
(S)-3-isopropyl-6-((1-(o-tolyl)ethyl)amino)pyrimidine-2,4(1H,3H)-dione;
(S)-3-cyclobutyl-6-((1-phenylethyl)amino)pyrimidine-2,4(1H,3H)-dione;
(S)-3-isopropyl-6-((1-(2-(trifluoromethyl)phenyl)ethyl)amino)pyrimidine-2,4(1H,3H)-dione;
(S)-3-(1-methylcyclopropyl)-6-((1-phenylethyl)amino)pyrimidine-2,4(1H,3H)-dione;
(S)-6-((1-(3-(1H-imidazol-1-yl)phenyl)ethyl)amino)-3-isopropylpyrimidine-2,4(1H,3H)-dione;
(S)-6-((1-phenylethyl)amino)-3-(pyridazin-4-yl)pyrimidine-2,4(1H,3H)-dione;
(S)-4-((1-phenylethyl)amino)-2H-[1,5'-bipyrimidine]-2,6(3H)-dione;
(S)-6-((1-phenylethyl)amino)-3-(pyrazin-2-yl)pyrimidine-2,4(1H,3H)-dione;
(S)-3-isopropyl-6-((1-(pyridin-3-yl)ethyl)amino)pyrimidine-2,4(1H,3H)-dione;
(S)-3-(1-methyl-1H-pyrazol-4-yl)-6-((1-phenylethyl)amino)pyrimidine-2,4(1H,3H)-dione;
(S)-3-isopropyl-6-((1-phenylbutyl)amino)pyrimidine-2,4(1H,3H)-dione;
6-(((S)-1-phenylethyl)amino)-3-((R)-tetrahydro-2H-pyran-3-yl)pyrimidine-2,4(1H,3H)-dione;
(S)-3-cyclopentyl-6-((1-phenylethyl)amino)pyrimidine-2,4(1H,3H)-dione;
(S)-3-isopropyl-6-((2-methyl-1-phenylpropyl)amino)pyrimidine-2,4(1H,3H)-dione;
(S)-3-(4,4-difluorocyclohexyl)-6-((1-phenylethyl)amino)pyrimidine-2,4(1H,3H)-dione;
(S)-3-(pentan-3-yl)-6-((1-phenylethyl)amino)pyrimidine-2,4(1H,3H)-dione;
(S)-3-(1-benzoylpiperidin-4-yl)-6-((1-phenylethyl)amino)pyrimidine-2,4(1H,3H)-dione;
(S)-3-isopropyl-6-((4-phenylbutan-2-yl)amino)pyrimidine-2,4(1H,3H)-dione;
methyl (S)-2-(2,6-dioxo-4-((1-phenylethyl)amino)-3,6-dihydropyrimidin-1(2H)-yl)acetate
(S)-3-isopropyl-6-((1-phenylpropan-2-yl)amino)pyrimidine-2,4(1H,3H)-dione;
3-((S)-1-(benzyloxy)propan-2-yl)-6-(((S)-1-phenylethyl)amino)pyrimidine-2,4(1H,3H)-dione;
3-((S)-1-hydroxypropan-2-yl)-6-(((S)-1-phenylethyl)amino)pyrimidine-2,4(1H,3H)-dione;
(R)-6-((2-hydroxy-1-phenylethyl)amino)-3-isopropylpyrimidine-2,4(1H,3H)-dione;
6-(((S)-1-phenylethyl)amino)-3-((R)-1,1,1-trifluoropropan-2-yl)pyrimidine-2,4(1H,3H)-dione;
6-(((S)-1-phenylethyl)amino)-3-((S)-1,1,1-trifluoropropan-2-yl)pyrimidine-2,4(1H,3H)-dione;
6-(((S)-1-phenylethyl)amino)-3-(4,4,4-trifluorobutan-2-yl)pyrimidine-2,4(1H,3H)-dione;
(S)-6-((1-phenylethyl)amino)-3-(2,2,2-trifluoroethyl)pyrimidine-2,4(1H,3H)-dione;
(S)-3-(tert-butyl)-6-((1-phenylethyl)amino)pyrimidine-2,4(1H,3H)-dione;
(S)-3-(2-methoxyethyl)-6-((1-phenylethyl)amino)pyrimidine-2,4(1H,3H)-dione;
6-(((S)-1-phenylpropyl)amino)-3-((S)-1,1,1-trifluoropropan-2-yl)pyrimidine-2,4(1H,3H)-dione;
3-((R)-1-cyclopropylethyl)-6-(((S)-1-phenylethyl)amino)pyrimidine-2,4(1H,3H)-dione;
3-((S)-1-cyclopropylethyl)-6-(((S)-1-phenylethyl)amino)pyrimidine-2,4(1H,3H)-dione;
(S)-6-((cyclobutyl(phenyl)methyl)amino)-3-ethylpyrimidine-2,4(1H,3H)-dione;
(S)-6-((1-(benzo[d][1,3]dioxol-5-yl)ethyl)amino)-3-isopropylpyrimidine-2,4(1H,3H)-dione;
(S)-6-((1-(benzo[d][1,3]dioxol-5-yl)ethyl)amino)-3-ethylpyrimidine-2,4(1H,3H)-dione;
(S)-6-((1-phenylpropyl)amino)-3-(2,2,2-trifluoroethyl)pyrimidine-2,4(1H,3H)-dione;
(S)-3-(cyclopropylmethyl)-6-((1-phenylethyl)amino)pyrimidine-2,4(1H,3H)-dione;
(S)-6-((cyclopropyl(phenyl)methyl)amino)-3-(2,2,2-trifluoroethyl)pyrimidine-2,4(1H,3H)-dione;
(S)-6-((cyclobutyl(phenyl)methyl)amino)-3-(2,2,2-trifluoroethyl)pyrimidine-2,4(1H,3H)-dione;
(S)-3-(1,3-dihydroxypropan-2-yl)-6-((1-phenylethyl)amino)pyrimidine-2,4(1H,3H)-dione;
6-(((S)-1-(4-fluorophenyl)propan-2-yl)amino)-3-((S)-1,1,1-trifluoropropan-2-yl)pyrimidine-2,4(1H,3H)-dione;
(S)-6-((1-(3-hydroxyphenyl)ethyl)amino)-3-isopropylpyrimidine-2,4(1H,3H)-dione;
6-((1-(2-hydroxyphenyl)ethyl)amino)-3-isopropylpyrimidine-2,4(1H,3H)-dione;
(S)-6-((1-phenylethyl)amino)-3-(1-(trifluoromethyl)cyclopropyl)pyrimidine-2,4(1H,3H)-dione;
(S)-3-(3,5-difluorophenyl)-6-((1-(4-fluorophenyl)propan-2-yl)amino)pyrimidine-2,4(1H,3H)-dione;
(S)-6-((1-(2,2-difluorobenzo[d][1,3]dioxol-5-yl)ethyl)amino)-3-isopropylpyrimidine-2,4(1H,3H)-dione;
(S)-6-((1-(2-chlorophenyl)ethyl)amino)-3-isopropylpyrimidine-2,4(1H,3H)-dione;
(S)-3-isopropyl-6-((1-(4-methoxyphenyl)ethyl)amino)pyrimidine-2,4(1H,3H)-dione;
(S)-6-((cyclopropyl(phenyl)methyl)amino)-3-ethylpyrimidine-2,4(1H,3H)-dione;
(S)-6-((1-(3-chlorophenyl)ethyl)amino)-3-ethylpyrimidine-2,4(1H,3H)-dione;
(S)-3-ethyl-6-((1-(3-(trifluoromethyl)phenyl)ethyl)amino)pyrimidine-2,4(1H,3H)-dione;
(S)-3-(cyclopropylmethyl)-6-((1-(3-fluorophenyl)ethyl)amino)pyrimidine-2,4(1H,3H)-dione;
(S)-3-(cyclopropylmethyl)-6-((1-(3-(trifluoromethyl)phenyl)ethyl)amino)pyrimidine-2,4(1H,3H)-dione;
(S)-6-((1-(3-chlorophenyl)ethyl)amino)-3-(cyclopropylmethyl)pyrimidine-2,4(1H,3H)-dione;
(S)-5-chloro-6-((1-(2,2-difluorobenzo[d][1,3]dioxol-5-yl)ethyl)amino)-3-isopropylpyrimidine-2,4(1H,3H)-dione;
(S)-6-((1-(3-fluorophenyl)ethyl)amino)-3-propylpyrimidine-2,4(1H,3H)-dione;
(S)-6-((1-(3-chlorophenyl)ethyl)amino)-3-propylpyrimidine-2,4(1H,3H)-dione;
(S)-3-propyl-6-((1-(3-(trifluoromethyl)phenyl)ethyl)amino)pyrimidine-2,4(1H,3H)-dione;
(S)-3-cyclobutyl-6-((1-(4-fluorophenyl)ethyl)amino)pyrimidine-2,4(1H,3H)-dione;
(S)-6-((1-(2-hydroxyphenyl)ethyl)amino)-3-isopropylpyrimidine-2,4(1H,3H)-dione;
(S)-6-((1-(3,4-difluorophenyl)ethyl)amino)-3-ethylpyrimidine-2,4(1H,3H)-dione;
3-((S)-sec-butyl)-6-(((S)-1-(4-fluorophenyl)ethyl)amino)pyrimidine-2,4(1H,3H)-dione;
(S)-6-((1-(4-fluorophenyl)ethyl)amino)-3-propylpyrimidine-2,4(1H,3H)-dione; and (S)-3-(6-fluoropyridin-2-yl)-6-((1-phenylethyl)amino)pyrimidine-2,4(1H,3H)-dione, or a pharmaceutically acceptable salt of any of the above.

In some embodiments, the compound is selected from

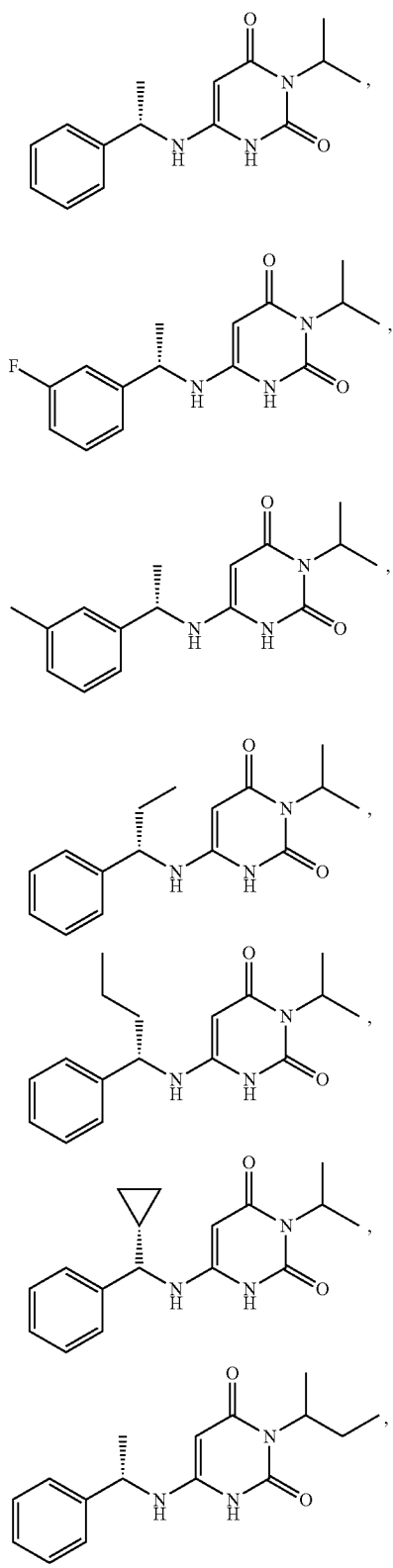

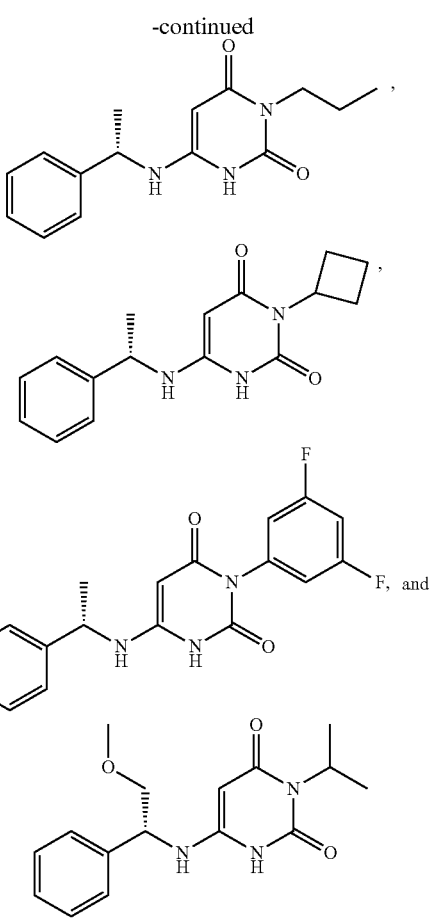

or a pharmaceutically acceptable salt thereof.

The compounds or pharmaceutically acceptable salts described herein (I) can be prepared via any suitable method. Compounds can be prepared, for example, by the route outlined in FIG. 1. As shown in FIG. 1A, a pyrimidine trione v can be synthesized via condensation of a urea iii with a malonate iv. The urea iii can be prepared via reaction of an amine i with an appropriate cyanate ii. The pyrimidine trione v is derivatized with a suitable leaving group (Lg) to provide intermediate vi. The leaving group can be, but is not limited to, a halogen such as a chloride or iodide. A halogenated intermediate vi can be prepared from pyrimidine triones by methods such as those described by Brown (*The Chemistry of Heterocyclic Compounds, The Pyrimidines*, John Wiley & Sons, 2009). Intermediates vi can be converted to compounds of formula I via reaction with amines vii. Certain chiral amines can be prepared from a ketone or aldehyde ix as shown in FIG. 1B; a sulfinyl imine xii derived from the ketone or aldehyde can be reacted with a Gringard reagent xiii to provide a chiral amine vii. One of skill in the art will appreciate that the compounds described herein can be prepared via other methods, such as those described by LaRock (*Comprehensive Organic Transformations: A Guide to Functional Group Preparations*, Wiley, 1999).

IV. Compositions

Also provided is a pharmaceutical composition containing a compound or pharmaceutically acceptable salt described herein and a pharmaceutically acceptable excipient. The compositions may be useful for treating hypertrophic cardiomyopathy in humans and other subjects.

The pharmaceutical compositions for the administration of the compounds or pharmaceutically acceptable salts described herein may conveniently be presented in unit dosage form and may be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active agent is generally included in an amount sufficient to produce the desired effect upon myocardial contractility (i.e. to decrease the often supranormal systolic contractility in HCM) and to improve left ventricular relaxation in diastole. Such improved relaxation can alleviate symptoms in hypertrophic cardiomyopathy and other etiologies of diastolic dysfunction. It can also ameliorate the effects of diastolic dysfunction causing impairment of coronary blood flow, improving the latter as an adjunctive agent in angina pectoris and ischemic heart disease. It can also confer benefits on salutary left ventricular remodeling in HCM and other causes of left ventricular hypertrophy due to chronic volume or pressure overload from, e.g., valvular heart disease or systemic hypertension.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions described herein may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3- butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds or pharmaceutically acceptable salts described herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds or pharmaceutically acceptable salts can be administered via ocular delivery by means of solutions or ointments. Still further, transdermal delivery of the subject compounds or pharmaceutically acceptable salts can be accomplished by means of iontophoretic patches and the like. For topical use, creams, ointments, jellies, solutions or suspensions, etc., containing the compounds or pharmaceutically acceptable salts described herein are employed. As used herein, topical application is also meant to include the use of mouth washes and gargles.

The compounds or pharmaceutically acceptable salts described herein may also be coupled to a carrier that is a suitable polymer for targetable drug carriers. Such polymers can include polyvinylpyrrolidone, pyran copolymer, polyhydroxy-propyl-methacrylamide-phenol, polyhydroxyethylaspartamide-phenol, or polyethyleneoxide-polylysine substituted with palmitoyl residues. Furthermore, the compounds or pharmaceutically acceptable salts described herein may be coupled to a carrier that is a biodegradable polymer useful in achieving controlled release of a drug, such as polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

V. Methods of Treating Cardiac Disorders

The mutations that lead to HCM cause significant perturbations in myosin mechanics. These mutations exert their effects via distinct mechanisms depending on their locations in the myosin gene. The well-studied HCM mutations, R403Q and R453C, are located in different sections of the motor domain and cause distinct mechanistic perturbations that lead to the common outcome of increased force production. Without wishing to be bound by any particular theory, it is believed that the compounds or pharmaceutically acceptable salts described herein can bind directly to the mutant sarcomeric proteins and correct for their aberrant function, either in cis (by affecting the same specific function) or in trans (by altering a complementary function). As such, they can provide therapeutic benefit for HCM patients by counteracting the hypercontractile and/or impaired relaxation associated with this disease.

Also provided is a method of treating hypertrophic cardiomyopathy (HCM) or a cardiac disorder having one or more pathophysiological features associated with HCM. The method includes administering to a subject in need thereof an effective amount of a compound or pharmaceutically acceptable salt described herein.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short and long term complications. The compounds or their pharmaceutically acceptable salts may reduce the severity of the chronic ischemic state associated with HCM and thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug-drug interactions, and/or side effects. The compounds or their pharmaceutically acceptable salts may reduce interstitial myocardial fibrosis and/or slow the progression, arrest, or reverse left ventricular hypertrophy.

Depending on the disease to be treated and the subject's condition, the compounds or pharmaceutically acceptable salts described herein may be administered by oral, parenteral (e.g., intramuscular, intraperitoneal, intravenous, ICV, intracisternal injection or infusion, subcutaneous injection, or implant), by implantation (e.g., as when the compound or pharmaceutically acceptable salt is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require improved ventricular relaxation during diastole, an appropriate dosage level will generally be about 0.001 to 100 mg per kg patient body weight per day which can be administered in single or multiple doses. In some embodiments, the dosage level will be about 0.01 to about 25 mg/kg per day; in some embodiments, about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. In some embodiments, for oral administration, the compositions are provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds or pharmaceutically acceptable salts may be administered on a regimen of 1 to 4 times per day, in some embodiments, once or twice per day.

It will be understood, however, that the specific dose level and frequency of dosage for any particular patient may be varied and will depend upon a variety of factors including the activity of the specific compound or pharmaceutically acceptable salt employed, the metabolic stability and length of action of that compound or pharmaceutically acceptable salt, the age, body weight, hereditary characteristics, general health, sex and diet of the subject, as well as the mode and time of administration, rate of excretion, drug combination, and the severity of the particular condition for the subject undergoing therapy.

Compounds and compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Suitable additional active agents include, for example: therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The weight ratio of the compound provided herein to the second active ingredient may be varied and will depend upon the effective dose of each ingredient. Generally, an effective dose of each will be used.

VI. Examples
Abbreviations
aq: aqueous
BBr$_3$: boron tribromide
CH$_2$Cl$_2$: dichloromethane
CH$_3$CN: acetonitrile
CH$_3$OH: methanol
DIAD: diisopropyl azodicarboxylate
DIEA: diisopropyl ethylamine
DMF: dimethyl formamide
DMSO: dimethyl sulfoxide
equiv.: equivalents
Et$_3$N: triethylamine
Et$_2$O: diethyl ether
EtOH: ethanol
FeSO$_4$: ferrous sulfate
h: hour(s)
HCl: hydrogen chloride
H$_2$O: water
K$_2$CO$_3$: potassium carbonate
KHSO$_4$: potassium bisulfate
KNCO: potassium isocyanate
LiBr: lithium bromide
MgSO$_4$: magnesium sulfate
mL: milliliter
MW: microwave (reaction done in microwave reactor)
NaCl: sodium chloride
NaH: sodium hydride
NaHCO$_3$: sodium bicarbonate
NaOEt: sodium ethoxide
NaOH: sodium hydroxide
NaOMe: sodium methoxide
Na$_2$SO$_4$: sodium sulfate
NH$_4$Cl: ammonium chloride
NMP: n-methyl pyrrolidinone
pH: −log [H$^+$]
POCl$_3$: phosphoryl trichloride
PPTS: pyridinium p-toluenesulfonate
RP-HPLC: reversed phase high pressure liquid chromatography
RT: room temperature
SEMCl: 2-(trimethylsilyl)ethoxymethyl chloride
TEBAC: triethylbenzylammonium chloride
TFA: trifluoroacetic acid
THF: tetrahydrofuran
TLC: thin layer chromatography Example 1

Preparation of (S)-3-Isopropyl-6-((1-phenylethyl)amino)pyrimidine-2,4(1H,3H)-dione

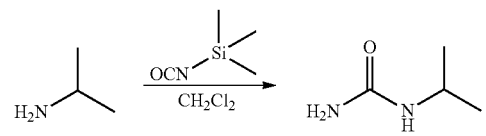

Compound 1.1. Isopropylurea. To a stirred solution of isopropylamine (15.3 g, 0.258 mol, 1.0 equiv) in CH$_2$Cl$_2$ (200 mL) under argon at 0° C. was added dropwise trimethylsilyl isocyanate (30 g, 0.26 mol, 1.0 equiv). The resulting mixture was allowed to reach ambient temperature and stirred overnight. After cooling to 0° C., CH$_3$OH (100 mL) was added dropwise. The resulting solution was stirred for 2 hours (h) at room temperature and then concentrated under reduced pressure. The crude residue was recrystallized from CH$_3$OH:Et$_2$O (1:20) to yield 15.4 g (58%) the title compound as a white solid. LC/MS: m/z (ES+) 103 (M+H)$^+$.

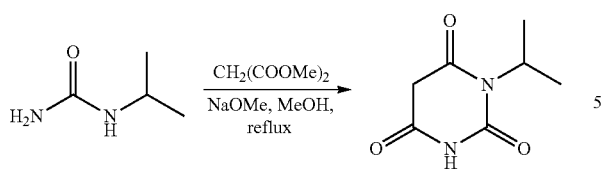

Compound 1.2. 1-Isopropyl barbituric acid. To a stirred solution of 1.1 (14.4 g, 0.14 mol, 1.00 equiv) in CH$_3$OH (500 mL) were added dimethyl malonate (19.55 g, 0.148 mol, 1.05 equiv) and sodium methoxide (18.9 g, 0.35 mol, 2.50 equiv). The resulting mixture was stirred overnight at 65° C. After cooling to ambient temperature and then to 0° C., the pH was carefully adjusted to 3 using aqueous concentrated HCl. The resulting mixture was concentrated under reduced pressure. The residue was taken up in EtOH (200 mL) and filtered. The filtrate was concentrated under reduced pressure and the residue was purified by silica gel column chromatography using CH$_2$Cl$_2$/CH$_3$OH (20:1) as eluent to yield 16.8 g (50%) of the title compound as a white solid. LC/MS: m/z (ES+) 171 (M+H)+. [1] $^1$H-NMR (300 MHz, d$_6$-DMSO): δ 11.19 (s, 1H), 4.83 (m, 1H), 3.58 (s, 2H), 1.32 (d, J=6.0 Hz, 6H).

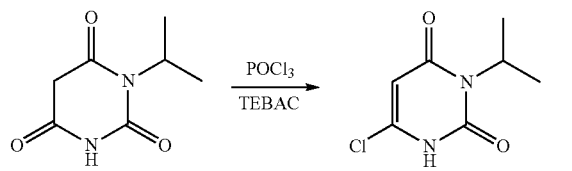

Compound 1.3. 6-chloro-3-isopropylpyrimidine-2,4(1H,3H)-dione. To a 100-mL round-bottom flask containing compound 1.2 (11.4 g, 66.99 mmol, 1.00 equiv) under argon were added triethylbenzylammonium chloride (21.3 g, 93.51 mmol, 1.40 equiv) and POCl$_3$ (30 mL). The resulting mixture was stirred overnight at 50° C. After cooling to room temperature, the mixture was concentrated under reduced pressure. The residue was dissolved in CH$_2$Cl$_2$ (150 mL) followed by slow addition of H$_2$O (100 mL). The phases were separated and the organic layer was washed with H$_2$O (100 mL), dried with anhydrous Na$_2$SO$_4$, and concentrated under reduced pressure. The crude residue was purified by silica gel column chromatography using EtOAc/petroleum ether (1:1) as eluent to yield 5.12 g (40%) of the title compound as a light yellow solid. $^1$H-NMR (300 MHz, d$_6$-DMSO): δ 12.22 (s, 1H), 5.88 (s, 1H), 4.95 (m, 1H), 1.34 (d, J=6.0 Hz, 6H).

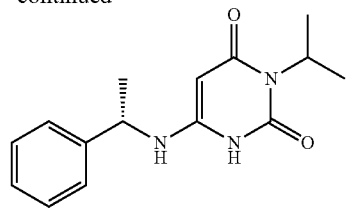

Compound 1. (S)-3-Isopropyl-6-((1-phenylethyl)amino)pyrimidine-2, 4(1H,3H)-dione. To a solution of 6-chloro-3-isopropylpyrimidine-2,4(1H,3H)-dione (1.3, 1.0 g, 5.31 mmol) in 1,4-dioxane (20 mL) was added (S)-α-methylbenzylamine (Sigma-Aldrich, 1.43 g, 11.7 mmol, 2.2 equiv). The reaction mixture was stirred at 80° C. for 24 h. After cooling to ambient temperature, the mixture was concentrated under reduced pressure. The residual was taken up in EtOAc (70 mL) and washed with aqueous 1N HCl (2×50 mL) and brine (40 mL). The organic layer was dried with anhydrous Na$_2$SO$_4$ and then concentrated under reduced pressure to half the original volume to yield a precipitate. Hexane (20 mL) was added and the mixture was stirred at room temperature. The resulting solid was collected by filtration, washed with hexane (20 mL), and dried to yield 1.0 g (69%) of the title compound as a white solid. LC/MS: m/z (ES+) 274 (M+H)+. $^1$H-NMR (400 MHz, d$_6$-DMSO): δ 9.77 (s, 1H), 7.32 (m, 4H), 7.24 (m, 1H), 6.50 (d, J=6.8 Hz, 1H), 4.87 (m, 1H), 4.52 (m, 1H), 4.31 (d, J=6.8 Hz, 1H), 1.37 (m, 3H), 1.24 (m, 6H). $^1$H NMR (400 MHz, CD$_3$OD) δ ppm 7.39-7.20 (m, 5H), 5.01 (m, 1H), 4.48 (m, 1H), 1.49 (d, J=6.7 Hz, 3H), 1.36 (m, 6H).

Example 2

Preparation of (S)-5-Fluoro-3-isopropyl-6-((1-phenylethyl)amino)pyrimidine-2,4(1H,3H)-dione (2)

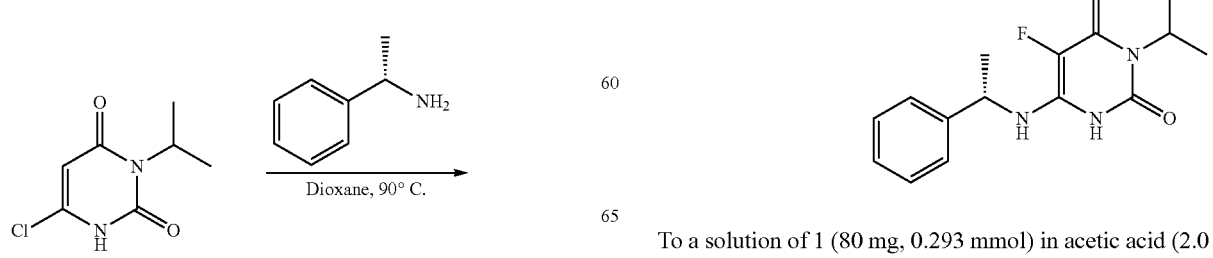

To a solution of 1 (80 mg, 0.293 mmol) in acetic acid (2.0 mL) was added selectfluor (104 mg, 0.293 mmol, 1.0 equiv.). The mixture was stirred at room temperature for 2 h. It was then concentrated under reduced pressure. The residue was purified by silica gel column chromatography, eluted with 0-50% EtOAc in hexanes to give 6 mg (7%) of the title compound as a white solid. LC/MS: m/z (ES+) 292 (M+H)+. $^1$H NMR (400 MHz, CD$_3$OD): δ ppm 7.36-7.24 (m, 5H), 5.04-4.97 (m, 1H), 4.94-4.88 (m, 1H), 1.54 (d, J=8.0 Hz, 3H), 1.39 (m, 6H).

Example 3

Preparation of (S)-5-Bromo-3-isopropyl-6-((1-phenylethyl)amino)pyrimidine-2,4(1H,3H)-dione (3)

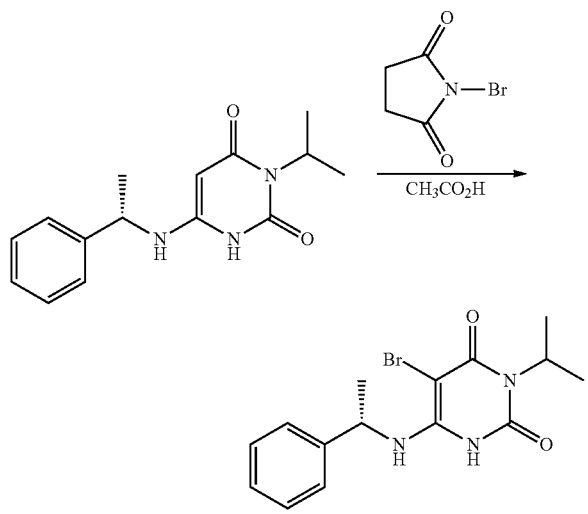

To a solution of 1 (55 mg, 0.201 mmol) in acetic acid (1.0 mL) was added N-bromosuccinamide (35 mg, 0.196 mmol). The mixture was stirred at room temperature for 1 hour. It was then concentrated under reduced pressure. The residue was purified by a silica gel column, eluted with 0-40% EtOAc in hexanes to give 52 mg (74%) of the title compound as a white solid. LC/MS: m/z (ES+) 352, 354 (M+H, bromine pattern)+. $^1$H-NMR (400 MHz, CDCl$_3$) δ ppm 8.96 (br s, 1H), 7.43-7.28 (m, 5H), 5.28 (d, J=7.4 Hz, 1H), 5.14 (m, 1H), 4.87 (m, 1H), 1.62 (d, J=6.7 Hz, 3H), 1.45-1.39 (m, 6H).

Example 4

Preparation of (S)-6-((1-(3-Chlorophenyl)ethyl)amino)-5-fluoro-3-isopropylpyrimidine-2,4(1H,3H)-dione

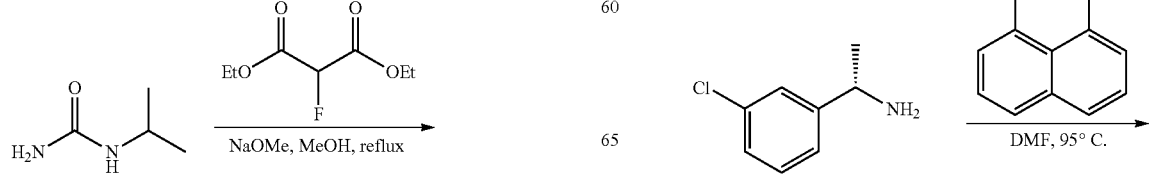

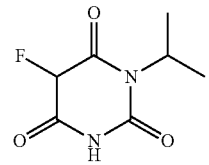

Compound 4.1. 5-Fluoro-1-isopropylpyrimidine-2,4,6 (1H,3H,5H)-trione). To a 100 mL round bottom flask containing a solution of 1.1 (1.31 g, 0.013 mol, 1.00 equiv) in CH$_3$OH (15 mL) were added diethyl fluoromalonate (2.41 g, 0.014 mol, 1.05 equiv) and sodium methoxide (1.74 g, 0.032 mol, 2.50 equiv). The reaction flask was equipped with a reflux condenser and was stirred for 4 h in an oil bath heated at 85° C. The reaction was cooled to 0° C. and was quenched with careful addition of concentrated HCl, adjusting to pH=2 with the addition of excess concentrated HCl. The reaction mixture was concentrated under reduced pressure and the resulting residue was dried for 18 h under high vacuum to provide 2.65 g of the title compound (98%). $^1$H-NMR (400 MHz, CDCl$_3$): δ ppm 5.53 (d, J=24.0 Hz, 1H), 4.91 (m, 2H), 1.46 (m, 6H).

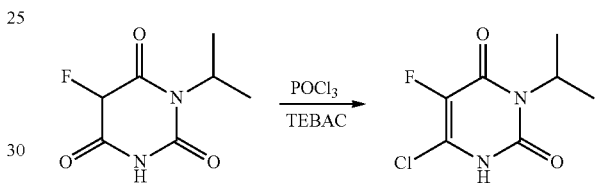

Compound 4.2. 6-Chloro-5-fluoro-3-isopropylpyrimidine-2,4(1H,3H)-dione. To a 100-mL round-bottom flask equipped with a reflux condenser containing 4.1 (2.65 g, 0.014 mmol, 1.00 equiv) were added triethylbenzylammonium chloride (4.50 g, 0.019 mmol, 1.40 equiv) and POCl$_3$ (25 mL). The reaction mixture was stirred for 4 h at 50° C. and then was cooled to room temperature. The mixture was concentrated under reduced pressure and the resulting residue was dissolved in CH$_2$Cl$_2$ (50 mL). Water (50 mL) was added slowly and the layers were separated. The organic layer was washed a second time with H$_2$O (100 mL), dried with anhydrous MgSO$_4$, and concentrated under reduced pressure. The resulting residue was purified by flash chromatography (silica gel, 30% EtOAc in hexanes) to yield 2.67 g (93%) of the title compound as a white solid. $^1$H-NMR (400 MHz, CDCl$_3$): δ ppm 5.19-5.05 (m, 2H), 1.48 (d, J=7.04 Hz, 6H).

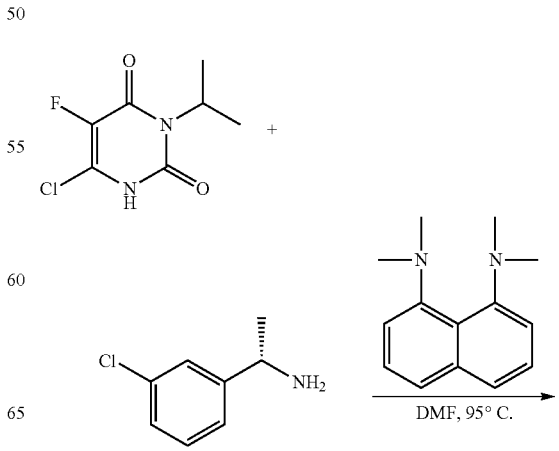

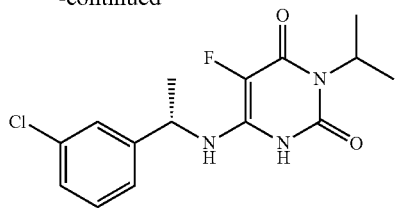

Compound 4. (S)-6-((1-(3-Chlorophenyl)ethyl)amino)-5-fluoro-3-isopropylpyrimidine-2,4(1H,3H)-dione. To a solution of 4.2 (150 mg, 0.70 mmol, 1 equiv) in DMF (2 mL) contained in a heavy wall pressure vessel were added (S)-3-chloro-α-methylbenzylamine (150 mg, 0.70 mmol, 1.0 equiv) and proton sponge (190 mg, 0.90 mol, 1.25 equiv). The pressure vessel was sealed and the reaction mixture was heated to 95° C. for 3 h behind a blast shield. The reaction mixture was cooled to room temperature and concentrated under reduced pressure. The resulting residue was purified by preparative RP-HPLC utilizing a Shimadzu, Prominence LC-20AP system equipped with a Phenomenex Gemini-NX C18 column (eluting with 10-90% CH$_3$CN/H$_2$O in 30 min., 20 mL/min (both containing 0.1% TFA)). The fractions containing pure compound were combined and lyophilized to provide 30 mg (13%) of the title compound as a white solid. LC/MS: m/z (ES+) 326 (M+H)$^+$. $^1$H-NMR (400 MHz, CDCl$_3$) δ ppm 9.47 (br s, 1H), 7.35-7.27 (m, 3H), 7.22-7.16 (m, 1H), 5.12 (m, 1H), 4.89 (m, 1H), 4.69 (d, J=5.9 Hz, 1H), 1.59 (d, J=6.7 Hz, 3H), 1.43 (m, 6H).

Example 5

Preparation of (S)-6-((1-(3,5-Difluorophenyl)ethyl)amino)-3-isopropylpyrimidine-2,4(1H,3H)-dione

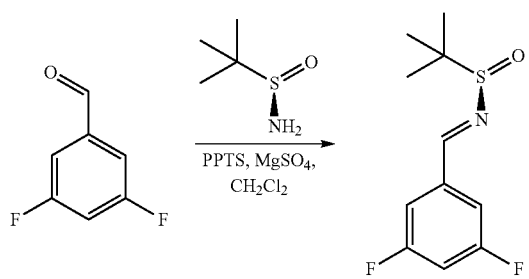

Compound 5.1. ((R,E)-N-(3,5-difluorobenzylidene)-2-methylpropane-2-sulfinamide. To a solution of 3,5-difluorobenzaldehyde (1.00 g, 7.04 mmol, 1.00 equiv) in CH$_2$Cl$_2$ (20 mL) were added pyridinium p-toluenesulfonate (0.089 g, 0.35 mmol, 0.05 equiv), (R)-(+)-2-methylpropane-2-sulfinamide (0.852 g, 7.03 mmol, 1.00 equiv), and MgSO$_4$ (4.2 g, 35.00 mmol, 5.00 equiv). The resulting mixture was stirred overnight at room temperature. The reaction mixture was filtered and concentrated under reduced pressure. The resulting residue was purified by flash chromatography (silica gel, 20% EtOAc in petroleum ether) to provide 500 mg (29%) of the title compound as a yellow oil.

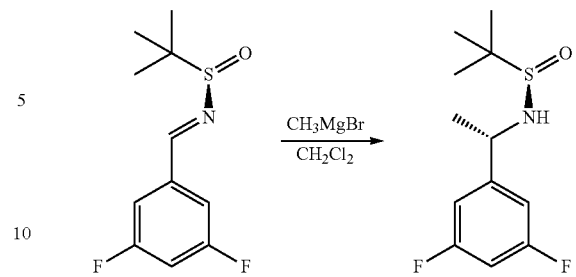

Compound 5.2. (R)—N—((S)-1-(3,5-difluorophenyl)ethyl)-2-methylpropane-2-sulfinamide. Methylmagnesium bromide (5.17 mL, 3M, 2.00 equiv) was added dropwise to a solution of 5.1 (1.9 g, 7.75 mmol, 1.00 equiv) in CH$_2$Cl$_2$ (50 mL) under argon at −48° C. The reaction mixture was warmed to room temperature and stirred overnight. The reaction was carefully quenched with a saturated aqueous NH$_4$Cl solution (20 mL). The layers were separated and the aqueous layer was further extracted with CH$_2$Cl$_2$ (3×50 mL). The combined organic layers were dried over anhydrous MgSO$_4$ and concentrated under reduced pressure to provide 1.3 g (64%) of the title compound as a yellow oil. $^1$H NMR (300 MHz, CDCl$_3$): δ ppm 6.92-6.81 (m, 2H), 6.75-6.65 (m, 1H), 4.65-4.55, (m, 1H), 3.46-3.42 (m, 1H), 1.53-1.44 (m, 3H), 1.26-1.22 (m, 9H).

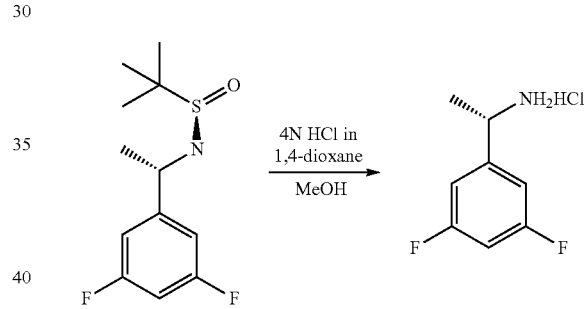

Compound 5.3. (S)-1-(3,5-Difluorophenyl)ethan-1-amine hydrochloride. To a solution of 5.2 (1.3 g, 4.97 mmol, 1.00 equiv) in CH$_3$OH (10 mL) was added 4N HO in 1,4-dioxane (2.67 mL, 2.00 equiv). The reaction mixture was stirred for 0.5 h at room temperature and then was concentrated under reduced pressure. The resulting residue was dissolved in CH$_3$OH (3 mL) and Et$_2$O (300 mL) was added. The resulting precipitate was isolated by filtration to provide 0.80 g (83%) of the title compound. $^1$H NMR (300 MHz, D$_2$O): δ ppm 6.98-6.83 (m, 3H), 4.45-4.38 (m, 1H), 1.51-1.48 (d, J=6.9 Hz, 3H).

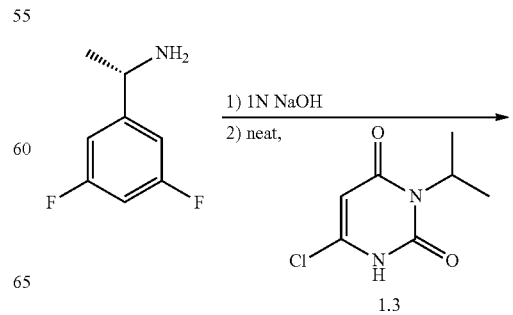

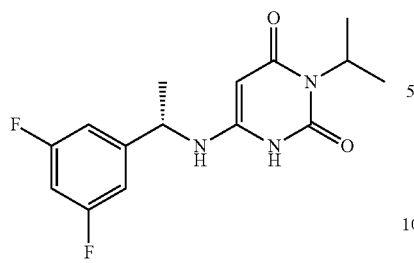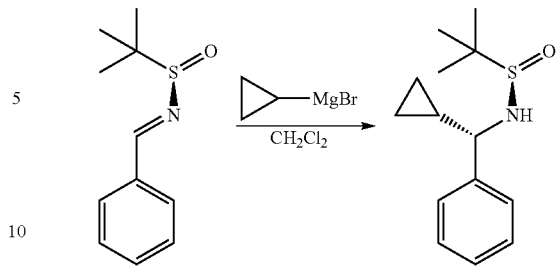

Compound 5. (S)-6-((1-(3,5-Difluorophenyl)ethyl)amino)-3-isopropylpyrimidine-2,4(1H,3H)-dione. Compound 5.3 (50 mg, 0.32 mmol, 1.00 equiv) was dissolved in 1N NaOH (10 mL), and the resulting mixture was stirred at 25° C. After 1 h, the mixture was extracted with EtOAc (5×10 mL). The combined organic layers were dried with anhydrous Na$_2$SO$_4$, filtered, and concentrated under reduced pressure. The resulting residue and compound 1.3 (35.6 mg, 0.19 mmol, 0.60 equiv) were combined. The mixture was stirred at 100° C. for 18 h, then was cooled to room temperature and concentrated under reduced pressure. The resulting residue was purified by preparative RP-HPLC to provide 28 mg (29%) of the title compound as an off white solid. LC/MS: m/z (ES+) 310 (M+H)$^+$. $^1$H-NMR (300 MHz, DMSO-d$_6$): δ ppm 9.83 (s, 1H), 7.06-7.12 (m, 3H), 6.54 (d, J=6.6 Hz, 1H), 4.91-4.82 (m, 1H), 4.54-4.46 (m, 1H), 4.30 (m, 1H), 1.34 (d, J=6.6 Hz, 3H), 1.22 (d, J=6.9 Hz, 6H).

Compound 6.2. (S)—N—((S)-Cyclopropyl(phenyl)methyl)-2-methylpropane-2-sulfinamide. The title compound was prepared using a protocol similar to that used for the preparation of 5.2 except 6.1 (1.0 g, 4.78 mmol, 1.00 equiv) and cyclopropylmagnesium bromide (9.6 mL, 1M, 2.00 equiv) were used in place of 5.1 and methylmagnesium bromide to provide 0.5 g (35%) of the title compound as a yellow oil. $^1$H NMR (300 MHz, DMSO-d$_6$): δ ppm 7.36-7.23 (m, 5H), 3.67-3.51 (m, 2H), 1.31 (m, 10H), 0.85-0.15 (m, 4H).

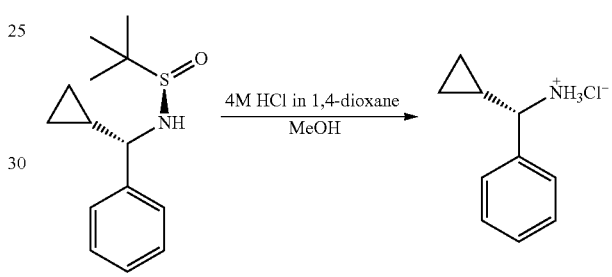

Compound 6.3. (S)-Cyclopropyl(phenyl)methanamine hydrochloride. The title compound was prepared using a protocol similar to that used for the preparation of 5.3 except 6.2 (500 mg, 1.69 mmol, 1.00 equiv) was used in place of 5.2 to provide 220 mg (88%) of the title compound as a yellow oil. $^1$H NMR (300 MHz, d$_6$-DMSO): δ ppm 7.37-7.31 (m, 5H), 3.53 (d, J =10.0 Hz, 1H), 1.37-1.25 (m, 1H), 0.75-0.55 (m, 1H), 0.53-0.31 (m, 2H), 0.25-0.15 (m, 1H).

Example 6

Preparation of (S)-6-((Cyclopropyl(phenyl)methyl)amino)-3-isopropylpyrimidine-2,4(1H,3H)-dione

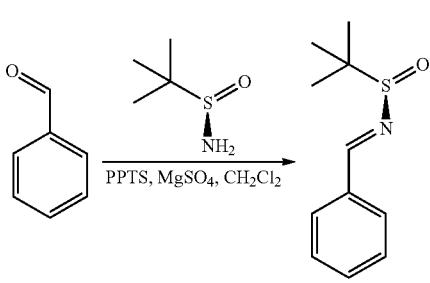

Compound 6.1. (R,E)-N-benzylidene-2-methylpropane-2-sulfinamide. The title compound was prepared in the same manner as 5.1 except benzaldehyde (5.0 g, 47.12 mmol, 1.00 equiv) was used in place of 3,5-difluorobenzaldehyde to provide 2.8 g (28%) of the title compound. $^1$H NMR (300 MHz, d$_6$-DMSO): δ ppm 8.62 (s, 1H), 7.89-7.87 (m, 2H), 7.55-7.49 (m, 3H), 1.31 (s, 9H).

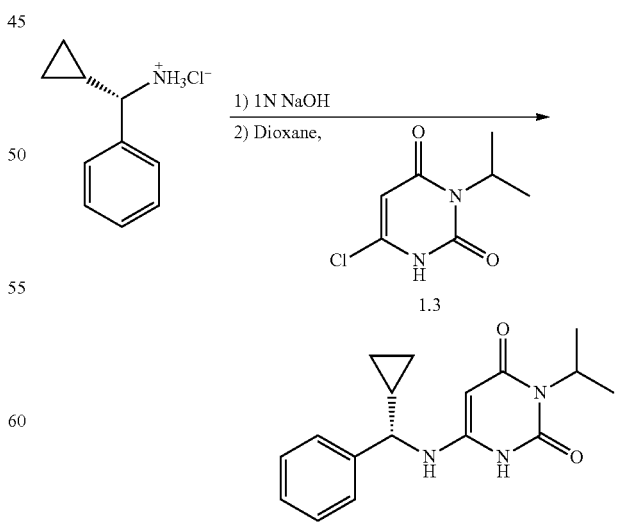

Compound 6. (S)-6-((Cyclopropyl(phenyl)methyl)amino)-3-isopropylpyrimidine-2,4(1H,3H)-dione. The title compound was prepared using a procedure similar to that used for the preparation of 5 except 6.3 (200 mg, 1.36 mmol, 1.00 equiv) was used instead of 5.3 and 1,4-dioxane was utilized as a solvent. After concentration under reduced pressure, purification utilizing a chiral HPLC (Phenomenex Lux 5μ Cellulose-4, 2.12*25, 5 μm column) with an isocratic mixture of EtOH:Hexane (1:4) as eluent provided 22 mg (5%) of the title compound as a white solid. LC/MS: m/z (ES+) 300 (M+H)+. $^1$H-NMR (300 MHz, DMSO-$d_6$) δ ppm 9.82 (s, 1H), 7.39-7.25 (m, 5H), 7.25-7.32 (m, 1H), 6.72 (m, 1H), 4.90 (m, 1H), 4.22 (s, 1H), 3.78 (m, 1H), 1.27 (m, 6H), 1.57 (m, 1H), 0.60 (m, 1H), 0.56-0.32 (m, 2H).

Example 7

Preparation of (S)-6-((cyclopropyl(3-methoxyphenyl)methyl)amino)-3-isopropylpyrimidine-2,4(1H,3H)-dione

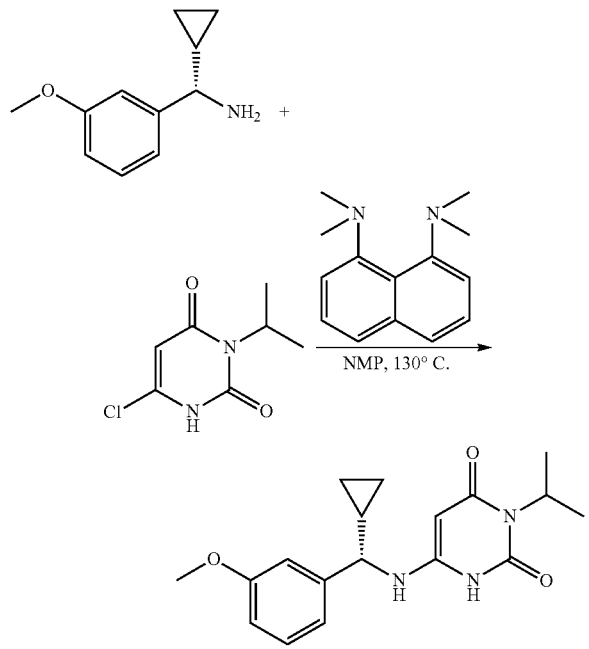

A solution of 6-chloro-3-isopropylpyrimidine-2,4(1H,3H)-dione (1.3, 50 mg, 0.265 mmol), (S)-cyclopropyl-(3-methoxyphenyl)methylamine (Sigma-Aldrich, 104 mg, 0.587 mmol), and proton sponge (85 mg, 0.397 mmol) in NMP (0.5 mL) was stirred at 130° C. for 2 h. After cooling to room temperature, the mixture was purified by preparative RP-HPLC (Shimadzu, Prominence LC-20AP system equipped with a Phenomenex Gemini-NX C18 column), eluting with 20-90% CH$_3$CN in H$_2$O (both containing 0.1% TFA). The fractions containing pure compound were combined and lyophilized to give 10 mg (11%) of the title compound as a white solid. LC/MS: m/z (ES+) 330 (M+H)+. $^1$H-NMR (400 MHz, CD$_3$OD): δ ppm 7.26 (t, J=7.8 Hz, H), 6.92-6.79 (m, 3H), 5.00 (m, 1H), 3.79 (s, 3H), 3.74 (d, J=8.6 Hz, 1H), 1.36 (d, J=7.0 Hz, 6H), 1.23-1.13 (m, 1H), 0.68-0.60 (m, 1H), 0.58-0.50 (m, 1H), 0.50-0.42 (m, 1H), 0.41-0.34 (m, 1H).

Example 8

Preparation of (S)-6-((Cyclobutyl(phenyl)methyl)amino)-3-isopropylpyrimidine-2,4(1H,3H)-dione

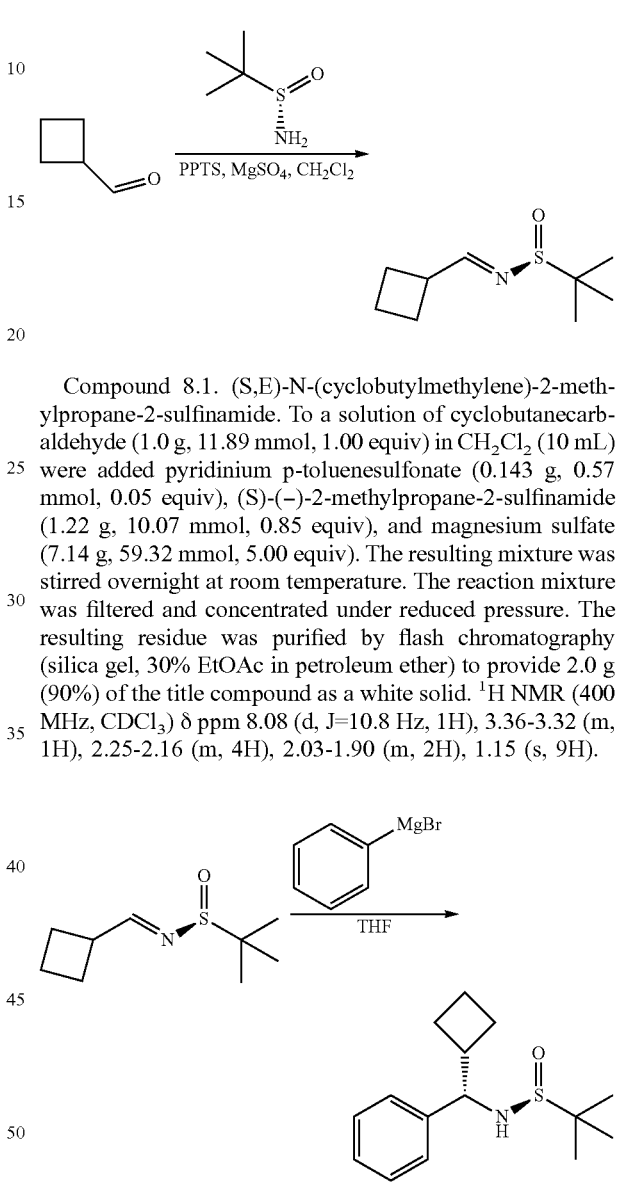

Compound 8.1. (S,E)-N-(cyclobutylmethylene)-2-methylpropane-2-sulfinamide. To a solution of cyclobutanecarbaldehyde (1.0 g, 11.89 mmol, 1.00 equiv) in CH$_2$Cl$_2$ (10 mL) were added pyridinium p-toluenesulfonate (0.143 g, 0.57 mmol, 0.05 equiv), (S)-(–)-2-methylpropane-2-sulfinamide (1.22 g, 10.07 mmol, 0.85 equiv), and magnesium sulfate (7.14 g, 59.32 mmol, 5.00 equiv). The resulting mixture was stirred overnight at room temperature. The reaction mixture was filtered and concentrated under reduced pressure. The resulting residue was purified by flash chromatography (silica gel, 30% EtOAc in petroleum ether) to provide 2.0 g (90%) of the title compound as a white solid. $^1$H NMR (400 MHz, CDCl$_3$) δ ppm 8.08 (d, J=10.8 Hz, 1H), 3.36-3.32 (m, 1H), 2.25-2.16 (m, 4H), 2.03-1.90 (m, 2H), 1.15 (s, 9H).

Compound 8.2. (S)—N—((S)-cyclobutyl(phenyl)methyl)-2-methylpropane-2-sulfinamide. Phenylmagnesium bromide (3M in Et$_2$O, 15.3 mL, 2.00 equiv) was added dropwise to a solution of 8.1 (4.3 g, 22.96 mmol, 1.00 equiv) in THF (40 mL). The reaction mixture was heated for 3 h at 65° C. It was then cooled to room temperature and carefully quenched with a saturated aqueous NH$_4$Cl solution (30 mL). The resulting mixture was extracted with EtOAc (3×30 mL), and the combined organic layers were dried with anhydrous Na$_2$SO$_4$ and concentrated under reduced pressure to provide 5.8 g (95%) of the title compound as a white solid. $^1$H-NMR (300 MHz, CDCl$_3$) δ 7.30-7.21 (m, 5H), 4.23 (d, J=9.6 Hz, 1H), 2.73-2.68 (m, 1H), 1.95-1.60 (m, 6H), 1.14 (s, 9H).

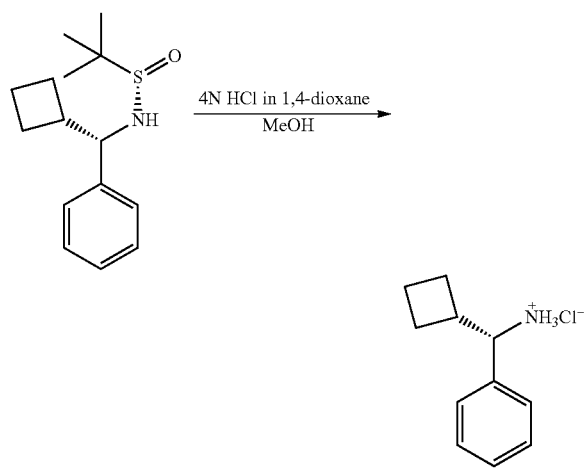

Compound 8.3. (S)-Cyclobutyl(phenyl)methanamine hydrochloride. The title compound was prepared using a procedure similar to that used for the preparation of 5.3 except 8.2 (5.8 g, 0.022 mol, 1.00 equiv) was used in place of 5.2 to provide 3.20 g (91%) of the title compound as a white solid. $^1$H NMR (300 MHz, D$_2$O): δ ppm 7.36-7.28 (m, 5H), 4.18 (m, 1H), 2.87-2.73 (m, 1H), 2.11-2.01 (m, 1H), 1.90-1.69 (m, 5H).

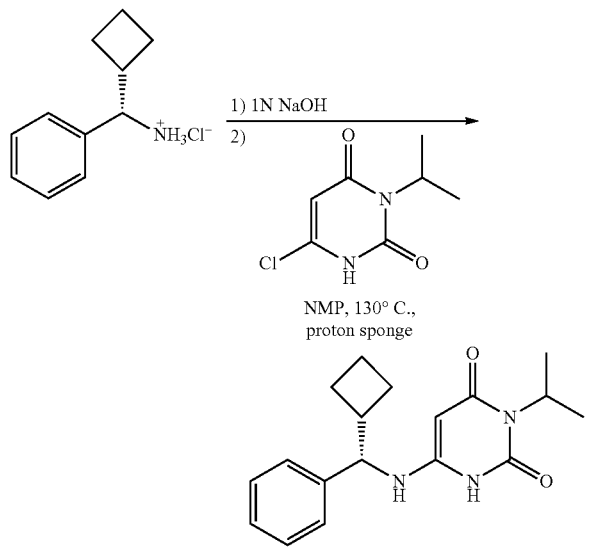

Compound 8. (S)-6-((Cyclobutyl(phenyl)methyl)amino)-3-isopropylpyrimidine-2,4(1H,3H)-dione. Compound 8.3 (0.200 g, 1.24 mmol, 1.00 equiv) was dissolved in 1N NaOH (10 mL), and was stirred for 1 h at 25° C. The reaction mixture was extracted with EtOAc (5×10 mL). The combined organic layers were dried over anhydrous Na$_2$SO$_4$, filtered and concentrated under reduced pressure. The resulting residue was dissolved in NMP and combined with 1.3 and proton sponge and heated as described for the preparation of 7. The title compound (35 mg, 9%) was isolated as a white solid. LC/MS: m/z (ES+) 314 (M+H)$^+$. $^1$H NMR (300 MHz, CD$_3$OD): δ ppm 7.38-7.26 (m, 5H), 5.08-4.97 (m, 1H), 4.25 (d, J=6.9 Hz, 1H), 2.68-2.58 (m, 1H), 2.19-2.13 (m, 1H), 1.98-1.83 (m, 5H), 1.36 (d, J=6.9 Hz, 6H-1).

Example 9

Preparation of (S)-6-((1-phenylethyl)amino)-3-(tetrahydro-2H-pyran-4-yl)pyrimidine-2,4(1H,3H)-dione

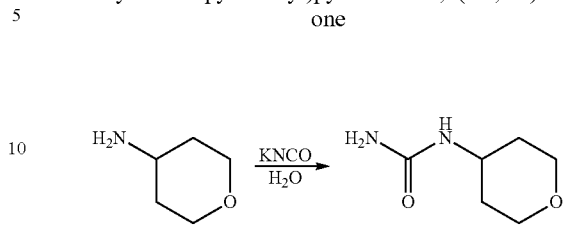

Compound 9.1. 1-(tetrahydro-2H-pyran-4-yl)urea. A mixture of tetrahydro-2H-pyran-4-amine (5.0 g, 49.4 mmol, 1.0 equiv.) and potassium isocyanate (4.0 g, 49.5 mmol, 1.0 equiv.) was refluxed in H$_2$O (50 mL) overnight. The reaction was cooled to room temperature and excess NaCl was added to help saturate the aqueous layer. The precipitate was isolated by filtration to provide the desired product (1.28 g, 8.88 mmol). The aqueous layer was washed with EtOAc (3×15 mL) and then was concentrated and azeotroped with toluene (3×100 mL). The resulting solid was suspended in 1:4 CH$_3$OH:EtOAc (100 mL) and filtered a total of four times. The combined organics were concentrated under reduced pressure and combined with the isolated precipitate to provide 5.01 g (70%) of the title compound. LC/MS: m/z (ES+) 145 (M+H)$^+$. $^1$H-NMR (400 MHz, DMSO-d$_6$): δ 6.14 (d, J=7.5 Hz, 1H), 5.47 (s, 2H), 3.85 (dt, J=11.6, 3.6 Hz, 2H), 3.65-3.52 (m, 1H), 3.38 (td, J=11.4, 2.2 Hz, 2H), 1.80-1.72 (m, 2H), 1.42-1.27 (m, 2H).

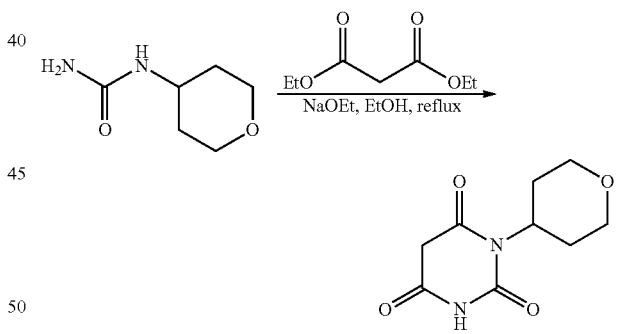

Compound 9.2. 1-(tetrahydro-2H-pyran-4-yl)pyrimidine-2,4,6(1H,3H,5H)-trione. Compound 9.1 (2.8 g, 19.4 mmol) was dissolved in EtOH (30 mL), and diethyl malonate (2.45 mL, 21.4 mmol, 1.1 equiv.), and NaOEt (7.55 mL, 23.3 mmol, 1.2 equiv.) were added. The reaction was stirred at 85° C. overnight, and then was cooled to room temperature. The reaction mixture was diluted with H$_2$O (5 mL), and excess KHSO$_4$ was added to saturate the aqueous layer. The reaction mixture was extracted with EtOAc (3×15 mL). The combined organic layers were dried with anhydrous MgSO$_4$, filtered and concentrated under reduced pressure. The resulting residue was purified by flash chromatography (silica gel, 0-25% CH$_3$OH in CH$_2$Cl$_2$) to provide 1.57 g of a mixture containing the title compound which was used without further purification. LC/MS: m/z (ES−) 211 (M−H)$^-$.

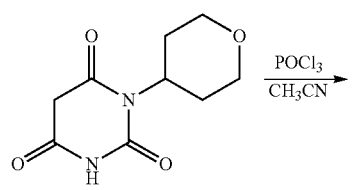

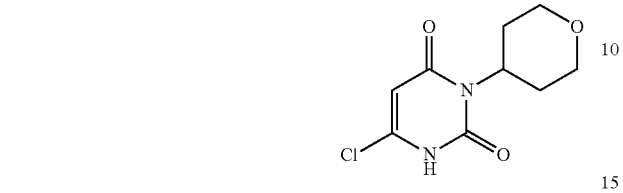

Compound 9.3. 6-chloro-3-(tetrahydro-2H-pyran-4-yl)pyrimidine-2,4(1H,3H)-dione. To a solution of 9.2 (1.57 g, 7.4 mmol, 1 equiv.) in CH₃CN (15 mL) was added POCl₃ (0.551 mL, 5.9 mmol, 0.8 equiv.). The reaction mixture was stirred at 80° C. overnight. An additional aliquot of POCl₃ (0.4 equiv.) was added and the reaction mixture was stirred at 80° C. for 3 h. Additional aliquots of POCl₃ (0.4 equiv.) were added after 3 h and 5 h of stirring at 80° C. The reaction mixture was then stirred at 90° C. for 1 h. The reaction was cooled to room temperature, concentrated, swirled with Et₂O (15 mL) and decanted. The resulting residue was rinsed with Et₂O (15 mL) and decanted until the Et₂O decanted clear. The resulting residue was carefully suspended in CH₃OH (10 mL), and filtered. The filtrate was concentrated to obtain a mixture of starting material and the title compound (≈85% pure, 1.6 g). LC/MS: m/z (ES−) 229 (M−H)⁻.

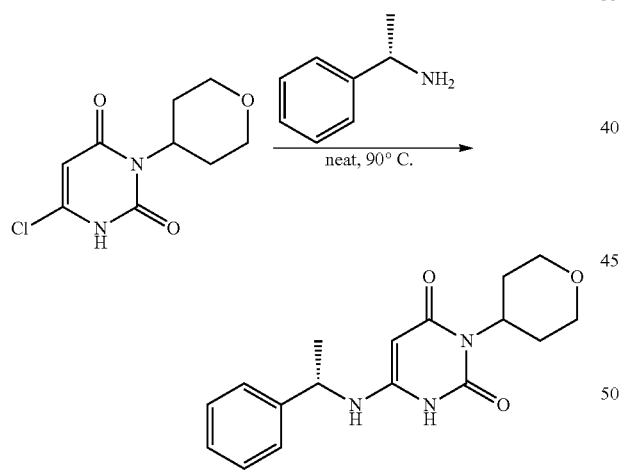

Compound 9. (S)-6-((1-phenylethyl)amino)-3-(tetrahydro-2H-pyran-4-yl)pyrimidine-2,4(1H,3H)-dione. A mixture of 9.3 (0.15 g, 0.65 mmol, 1 equiv.) and (S)-(−)-α-methylbenzylamine (470 mg, 3.88 mmol, 6.0 equiv.) was stirred overnight at 90° C. The reaction mixture was cooled to room temperature and the resulting residue was purified by preparative RP-HPLC (0-40% CH₃CN in H₂O in 30 min.), followed by a second purification on a preparatory TLC plate (2000 um) (7% CH₃OH in CH₂Cl₂) to provide 23 mg (11%) of the title compound. LC/MS: m/z (ES+) 316 (M+H)⁺. ¹H NMR (400 MHz, DMSO-d₆): δ ppm 10.23 (s, 1H), 7.40-7.32 (m, 4H), 7.31-7.17 (m, 1H), 6.93 (s, 1H), 4.84-4.71 (m, 1H), 4.56-4.43 (m, 1H), 4.35 (s, 1H), 3.93- 3.78 (m, 2H), 3.28 (t, J=12.1 Hz, 2H), 2.63-2.39 (m, 2H), 1.40 (d, J=6.7 Hz, 3H), 1.35-1.16 (m, 2H).

Example 10

Preparation of (S)-6-((1-(3-methoxyphenyl)ethyl)amino)-3-(tetrahydro-2H-pyran-4-yl)pyrimidine-2,4(1H,3H)-dione (10)

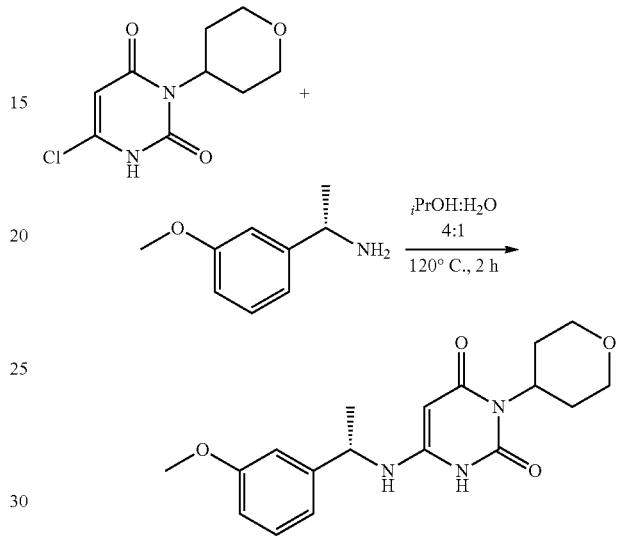

To a solution of 9.3 (0.58 g, 0.25 mmol) in a mixture of 2-propanol and H₂O (4:1, 1 mL) was added (S)-1-(3-methoxyphenyl)-ethylamine (0.113 g, 0.75 mmol, 3.0 equiv.). The reaction mixture was heated to 120° C. for 2 h. After cooling, the reaction mixture was concentrated under reduced pressure, dissolved in CH₃OH and filtered. The filtrate was purified by preparative RP-HPLC (20-100% CH₃CN in H₂O in 40 min. at 25 mL/min.) to provide 18 mg (21%) of the title compound as an off-white solid. LC/MS: m/z (ES+) 346 (M+H)⁺. ¹H NMR (400 MHz, acetone-d₆) δ 8.90 (s, 1H), 7.15 (dd, J=8.3, 8.1 Hz, 1H), 6.88 (s, 1H), 6.86 (d, 8.3 Hz, 1H), 6.68 (d, J=8.1 Hz, 1H), 6.15 (s, 1H), 4.74 (m, 1H), 4.48 (m, 1H), 4.35 (s, 1H), 3.82 (m, 2H), 3.68 (s, 3H), 3.2 (m, 2H), 2.55 (m, 2H) 1.44 (d, J=6.6 Hz, 3H), 1.15 (m, 2H).

Example 11

Preparation of 6-(((S)-1-phenylethyl)amino)-3-(tetrahydrofuran-3-yl)pyrimidine-2,4(1H,3H)-dione

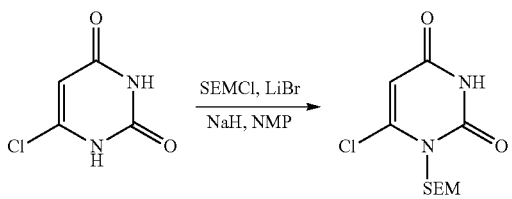 [SMILES: O=c1cc(Cl)[nH]c(=O)[nH]1 ; C[Si](C)(C)CCOCn1c(Cl)cc(=O)[nH]c1=O]

Compound 11.1. 6-chloro-1-((2-(trimethylsilyl)ethoxy)methyl)pyrimidine-2,4(1H,3H)-dione. To a mixture of 6-chloro-uracil (3.0 g, 20.47 mmol, 1 equiv.) and LiBr (1.78 g, 20.5 mmol, 1.0 equiv.) in NMP (70 mL) at 0° C. was added NaH (60% dispersion in mineral oil, 0.82 g, 20.5 mmol, 1.0 equiv.). The reaction mixture was stirred at 0° C. for 10 min, and 2-(trimethylsilyl)ethoxymethyl chloride (3.75 g, 22.5 mmol, 1.1 equiv.) was slowly added via an addition funnel. The reaction mixture was stirred overnight at room temperature and then diluted with EtOAc (150 mL). The mixture was washed with a saturated aqueous NH₄Cl solution (50 mL), saturated aqueous NaHCO₃ (50 mL), and brine (50 mL). The organic layer was dried with anhydrous Na₂SO₄ and concentrated under reduced pressure to provide 3.2 g (57%) of the title compound as a white solid. LC/MS: m/z (ES+) 299 (M+Na)⁺. ¹H NMR (400 MHz, CDCl₃): δ ppm 9.00-8.80 (br-s, 1H), 5.95 (s, 1H), 5.45 (s, 2H)), 3.63 (t, J=7.0 Hz, 2H), 1.48 (t, J=7.0 Hz, 2H), 0.01 (s, 9H).

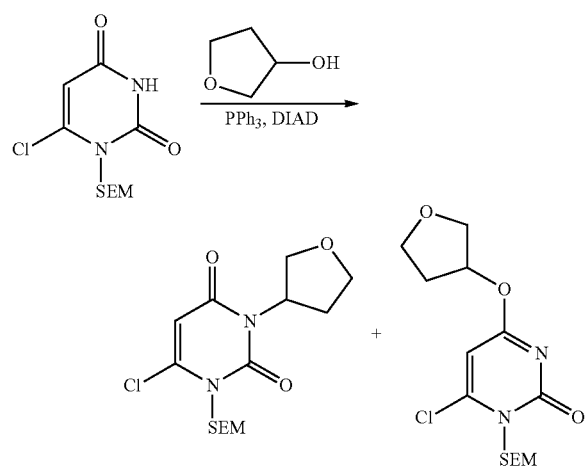

Compound 11.2. 6-chloro-3-(tetrahydrofuran-3-yl)-1-((2-(trimethylsilyl)ethoxy)methyl)pyrimidine-2,4(1H,3H)-dione. To a solution of 11.1 (277 mg, 1.0 mmol, 1 equiv.), 3-hydroxytetrahydrofuran (106 mg, 1.2 mmol, 1.2 equiv.), and triphenylphosphine (320 mg, 1.2 mmol, 1.2 equiv.) in THF (7.5 mL) at 0° C., was added diisopropyl azodicarboxylate (0.240 g, 1.2 mmol, 1.2 equiv.) dropwise. The reaction mixture was stirred at room temperature for 30 minutes. The reaction mixture was concentrated under reduced pressure and the resulting residue was purified by preparative RP-HPLC (20-100% CH₃CN in H₂O with 0.1% formic acid buffer in 40 min. at 25 mL/min.) to provide 102 mg (29%) of the title compound. LC/MS: m/z (ES+) 347 (M+H)⁺. ¹H NMR (400 MHz, CDCl₃) δ 5.92 (s, 1H), 5.58 (m, 1H), 5.41 (s, 2H), 4.20 (m, 1H), 4.00-3.85 (m, 3H), 3.65 (t, J=7.0 Hz, 2H), 2.35-2.20 (m, 1H), 2.20-2.08 (m, 1H), 0.95 (t, 2H), 0.01 (s, 9H); ¹³C NMR (CDCl₃) δ 160.7, 150.7, 145.6, 102.0, 74.8, 68.7, 67.9, 67.5, 51.9, 28.7, 18.0, 0.0.

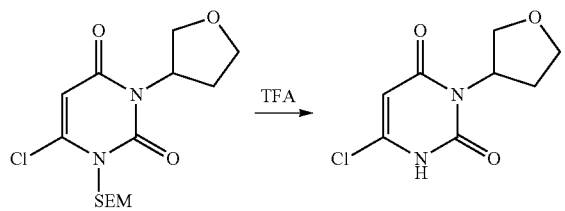 [SMILES: C[Si](C)(C)CCOCn1c(Cl)cc(=O)n(C2CCOC2)c1=O ; O=c1cc(Cl)[nH]c(=O)n1C1CCOC1]

Compound 11.3. 6-chloro-3-(tetrahydrofuran-3-yl)pyrimidine-2,4(1H,3H)-dione. Compound 11.2 (0.50 g, 1.4 mmol, 1.0 equiv.) was dissolved in trifluoroacetic acid (1 mL). The reaction mixture was stirred at room temperature for 30 minutes and then was concentrated under reduced pressure. The resulting residue was purified by preparative RP-HPLC (10% CH₃CN in H₂O in 40 min. at 25 mL/min.) to provide 300 mg (96%) of the title compound as a white solid. LC/MS: m/z (ES+) 217 (M+H)⁺. ¹H NMR (400 MHz, DMSO-d₆): δ ppm 5.90 (s, 1H), 5.35 (m, 1H), 4.00 (m, 1H), 3.85-3.68 (m, 3H), 2.20 (m, 1H), 2.01 (m, 1H).

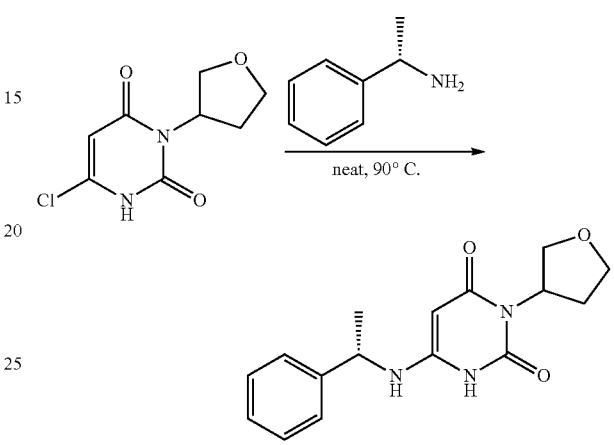

Compound 11. 6-(((S)-1-phenylethyl)amino)-3-(tetrahydrofuran-3-yl)pyrimidine-2,4(1H,3H)-dione. The title compound was prepared using a procedure similar to that used for the preparation of 9 except 11.3 (22 mg, 0.10 mmol, 1.00 equiv) was used in place of 9.3 to provide 15 mg (50%) of the title compound as a white solid. LC/MS: m/z (ES+) 302 (M+H)⁺. ¹H NMR (400 MHz, CDCl₃): δ ppm 10.50 (1H), 7.50-7.20 (m, 5H), 5.90 (m, 1H), 5.60 (m, 1H), 4.78 (m, 1H), 4.45 (s, 1H), 4.20 (m, 1H), 4.05-3.90 (m, 2H), 3.90-3.80 (m, 1H), 2.45-2.10 (m, 2H), 1.55 (d, J=6.7 Hz, 3H).

Example 12

Preparation of (S)-3-(1-(methylsulfonyl)piperidin-4-yl)-6-((1-phenylethylamino)pyrimidine-2,4(1H,3H)-dione

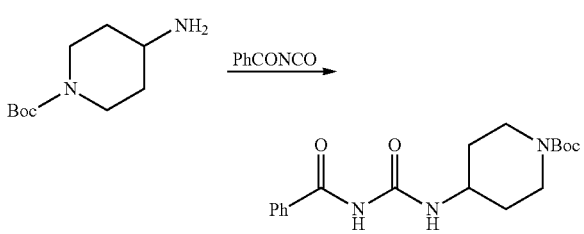

Compound 12.1. tert-Butyl 4-(3-benzoylureido)piperidine-1-carboxylate. To a solution of benzoylisocyanate (4.8 g, 32.6 mmol) in CH₂Cl₂ (180 mL) at 0° C. was added 4-amino-1-N-boc-piperidine (6.0 g, 30 mmol). The reaction mixture was stirred at room temperature for 4 h and concentrated. The residue was treated with Et₂O (100 mL). The precipitate was filtered and washed with Et₂O to yield 5.70 g (55%) of the title compound as a white solid. LC/MS: m/z (ES+) 337 (M+H)⁺.

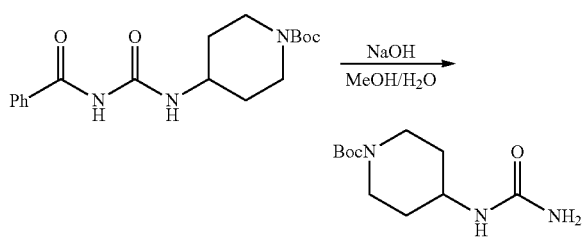

Compound 12.2. tert-Butyl 4-ureidopiperidine-1-carboxylate. To a mixture of 12.1 (5.60 g, 16.1 mmol) in CH$_3$OH (70 mL) and H$_2$O (70 mL) was added sodium hydroxide (11.6 g, 290 mmol) portionwise. The reaction mixture was stirred at room temperature overnight and then refluxed for 1 h. The mixture was cooled to room temperature and concentrated under reduced pressure to remove CH$_3$OH. The precipitate was filtered, washed with H$_2$O, and dried to yield 3.2 g (82%) of the title compound as a white solid. LC/MS: m/z (ES+) 266 (M+Na)$^+$.

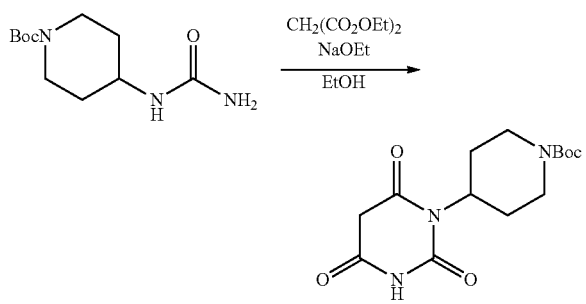

Compound 12.3. tert-Butyl 4-(2,4,6-trioxo-tetrahydropyrimidin-1(2H)-yl)piperidine-1-carboxylate. To a mixture of 12.2 (3.63 g, 14.9 mmol), diethylmalonate (2.6 mL, 16.5 mmol, 1.1 equiv.) and anhydrous ethanol (60 mL) was added NaOEt (21% in EtOH, 6.6 mL, 17.7 mmol, 1.2 equiv.). The mixture was refluxed for 14 h and concentrated. The residue was taken up in H$_2$O (15 mL) and washed with EtOAc (2×30 mL). The aqueous layer was separated and adjusted to pH=5 with concentrated. HCl. The precipitate was filtered, washed with H$_2$O and dried to give 3.70 g (80%) of the title compound as an off-white solid. LC/MS: m/z (ES+) 334 (M+Na)$^+$.

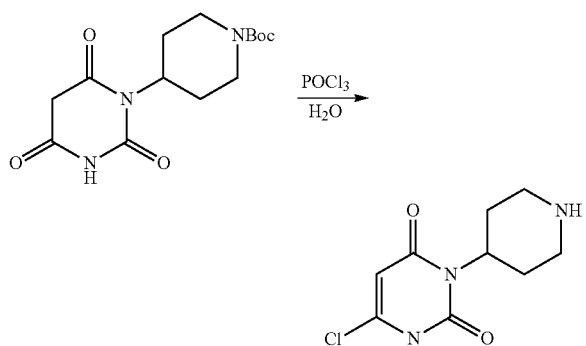

Compound 12.4. 6-chloro-3-(piperidin-4-yl)pyrimidine-2,4(1H,3H)-dione. To a mixture of 12.3 (2.55 g, 8.19 mmol) and POCl$_3$ (10 mL, 100.65 mmol) was added H$_2$O (0.41 mL, 22.78 mmol) dropwise. The mixture was stirred at 120° C. for 30 min and then concentrated. The residue was carefully taken up in ice water (20 g). To the mixture was added K$_2$CO$_3$ (~8.0 g) portionwise until the pH was ~7. The precipitate was filtered, washed with H$_2$O (20 mL) and EtOAc (50 mL). The resulting material was dried to yield 1.45 g (77%) of the title compound as an off-white solid. LC/MS: m/z (ES+) 230 (M+H)$^+$.

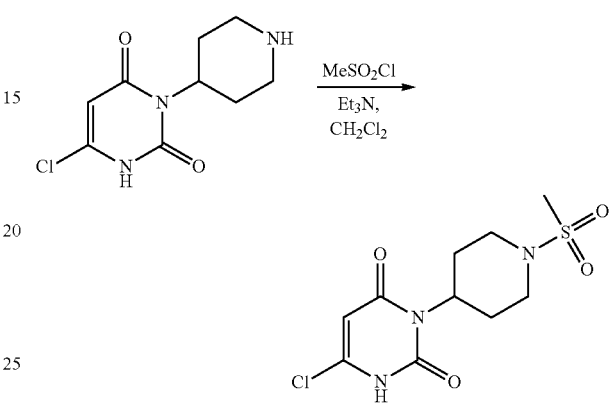

Compound 12.5. 6-chloro-3-(1-(methylsulfonyl)piperidin-4-yl)pyrimidine-2,4(1H,3H)-dione. To a mixture of 12.4 (380 mg, 1.65 mmol, 1.0 equiv.) and CH$_2$Cl$_2$ (8 mL) was added Et$_3$N (0.70 mL, 4.95 mmol, 3 equiv.) and methanesulfonyl chloride (0.23 mL, 2.5 mmol, 1.5 equiv.). The mixture was stirred at room temperature for 2 h and then quenched with H$_2$O (3 mL) to yield precipitate. The precipitate was filtered and washed with CH$_2$Cl$_2$ (3×3 mL). The filtrate was concentrated to ~1.5 mL. Filtration of a second precipitate was followed by washing with H$_2$O (2×1 mL) and CH$_2$Cl$_2$ (3×2 mL). The precipitates were combined to afford 320 mg (63%) of the title compound as an off-white solid. LC/MS: m/z (ES+) 308 (M+H)$^+$.

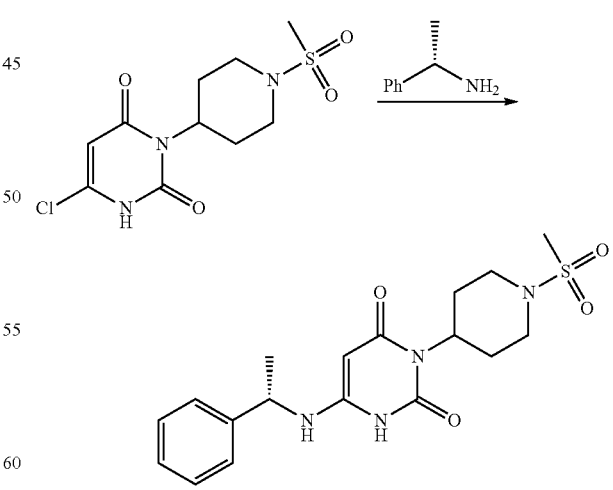

Compound 12. (S)-3-(1-(methylsulfonyl)piperidin-4-yl)-6-((1-phenylethylamino)pyrimidine-2,4(1H,3H)-dione. A mixture of 12.5 (20 mg, 0.065 mmol) and (S)-α-methylbenzylamine (180 mg, 1.5 mmol, 23 equiv.) was stirred at 125° C. for 1 h. The mixture was concentrated under reduced pressure, dissolved in CH₃OH and filtered. The filtrate was purified using preparative RP-HPLC eluting with linear gradient 20% to 100% CH₃CN in H₂O (0.1% formic acid buffer) over 40 min to give 16 mg (63%) of the title compound as an off-white solid. LC/MS: m/z (ES+) 393 (M+H)⁺. ¹H-NMR (400 MHz, DMSO-d₆): δ ppm 9.40 (br s, 1H), 7.35-7.25 (m, 4H), 7.15 (m, 1H), 6.55 (s, 1H), 4.58 (m, 1H), 4.42 (m, 1H), 4.30 (s, 1H), 3.52 (m, 2H), 2.79 (s, 3H), 2.70-2.62 (m, 2H), 2.50-2.48 (m, 2H), 1.48-1.38 (m, 2H), 1.32 (d, J=6.8 Hz, 3H).

Example 13

Preparation of (S)-methyl 4-(2,6-dioxo-4-(1-phenylethylamino)-2,3-dihydropyrimidin-1(6H)-yl)piperidine-1-carboxylate

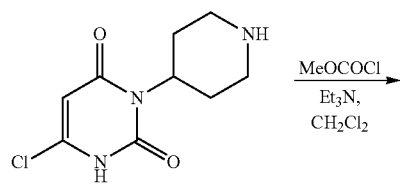

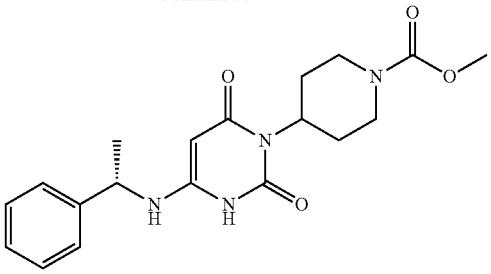

Compound 13. (S)-methyl 4-(2,6-dioxo-4-(1-phenylethylamino)-2,3-dihydropyrimidin-1(6H)-yl)piperidine-1-carboxylate. A mixture of 13.1 (58 mg, 0.20 mmol) and (S)-α-methylbenzylamine (240 mg, 1.5 mmol) was stirred at 120° C. for 0.5 h. The title compound was prepared using a procedure similar to that used for the preparation of 9 to provide 40 mg (63%) of the title compound as an off-white solid. LC/MS: m/z (ES+) 373 (M+H)⁺. ¹H-NMR (400 MHz, CDCl₃): δ ppm 9.85 (s, 1H), 7.29-7.15 (m, 5H), 5.75 (br s, 1), 4.80 (m, 1H), 4.60 (s, 1H), 4.35 (m, 1H), 4.20-4.00 (m, 2H), 3.58 (s, 3H), 2.80-2.70 (m, 2H), 2.46 (m, 2H), 1.50 (m, 2H), 1.38 (d, J=6.7 Hz, 3H).

Example 14

Preparation of 3-(R)-sec-butyl-6-(((S)-1-(3-methoxyphenyl)ethylamino)pyrimidine-2,4(1H,3H)-dione

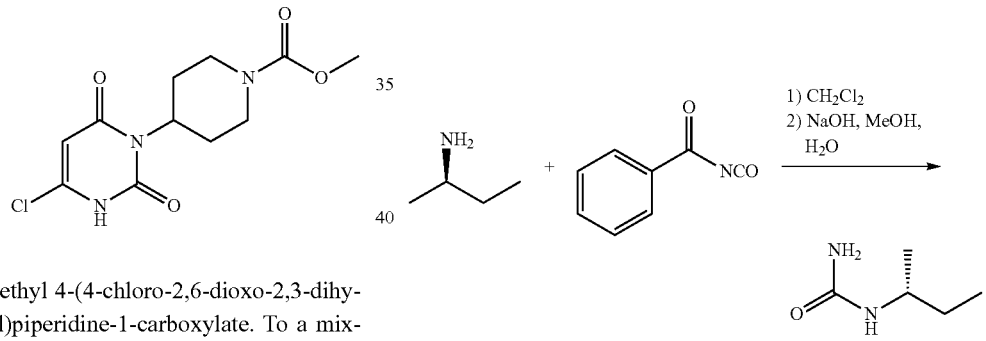

Compound 13.1. Methyl 4-(4-chloro-2,6-dioxo-2,3-dihydropyrimidin-1(6H)-yl)piperidine-1-carboxylate. To a mixture of 12.4 (115 mg, 0.5 mmol, 1.0 equiv.) and CH₂Cl₂ (2 mL) was added Et₃N (0.14 mL, 1.5 mmol, 3.0 equiv.), followed by methyl chloroformate (95 mg, 1.0 mmol, 2.0 equiv.). The mixture was stirred at room temperature for 1 h, diluted with CH₂Cl₂ (8 mL), washed with a saturated aqueous NaHCO₃ solution (1 mL), H₂O (1 mL), brine (1 mL), dried with anhydrous Na₂SO₄ and concentrated to yield 105 mg (73%) of an off-white solid. LC/MS: m/z (ES+) 288 (M+H)⁺.

Compound 14.1. (R)-1-sec-butylurea. Benzoyl isocyanate (5.36 g, 36.5 mmol, 1.05 equiv.) was dissolved in CH₂Cl₂ (20 mL) and cooled to 0° C. in an ice bath. (R)-butan-2-amine (2.54 g, 34.7 mmol, 1 equiv.) in CH₂Cl₂ (10 mL) was carefully added while stirring. The mixture was allowed to stir for 3 h at room temperature. After the reaction was deemed complete, the mixture was concentrated. The residue was suspended in Et₂O (20 mL) and filtered. The solid was taken up in a 1:1 mixture of CH₃OH and H₂O (200 mL) followed by the addition of NaOH (6.9 g, 174 mmol, 5 equiv.). The reaction was stirred overnight at room temperature. The CH₃OH was evaporated from the solution and the resulting precipitate (1.66 g, 39%) was collected. LC/MS: m/z (ES+) 117 (M+H)⁺.

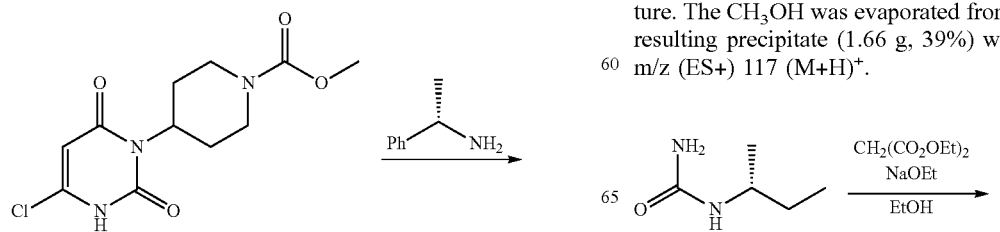

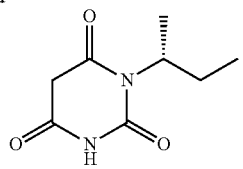

Compound 14.2. (R)-1-sec-butylpyrimidine-2,4,6(1H,3H,5H)-trione. Compound 14.1 (1.66 g, 14.3 mmol, 1.0 equiv.) was dissolved in EtOH (10 mL), and diethyl malonate (1.8 mL, 15.7 mmol, 1.1 equiv.), and NaOEt (5.6 mL, 17.1 mmol, 1.2 equiv.) were added. The reaction was stirred at 80° C. for 2 h and then cooled to room temperature. Water (20 mL) was added and then EtOH was removed by evaporation. KHSO$_4$ (excess) was added to saturate the aqueous layer which was then extracted with EtOAc. The combined organics were dried with anhydrous MgSO$_4$ and concentrated to yield 1.6 g (61%) of the title compound as a crude residue which was used without further purification. LC/MS: m/z (ES−) 183 (M−H)⁻.

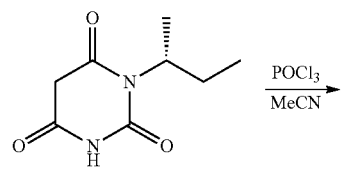

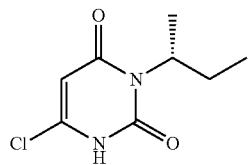

Compound 14.3. (R)-3-sec-butyl-6-chloropyrimidine-2,4 (1H,3H)-dione. A mixture of 14.2 (1.6 g, 8.7 mmol, 1 equiv.) and POCl$_3$ (648 µL, 7.0 mmol, 0.8 equiv.) in CH$_3$CN (10 mL) was stirred at 90° C. for 2 h. Additional POCl$_3$ (0.8 equiv.) was added and stirred at 90° C. for 3 h. The reaction was cooled to room temperature, carefully quenched with CH$_3$OH (10 mL), stirred for 30 minutes and purified with normal phase HPLC 0-25% CH$_3$OH/CH$_2$Cl$_2$ followed by a CH$_3$OH flush. The product and starting material co-eluted. The mixture was concentrated, the residue was taken up in CH$_3$CN (10 mL) and POCl$_3$ (648 uL) was added. The reaction was stirred at 90° C. for 3 h and then cooled to room temperature. The reaction was carefully quenched with CH$_3$OH (10 mL) and stirred for 30 minutes. The reaction mixture was purified by normal phase HPLC with previous condition, concentrated and dried under vacuum to yield 450 mg (32%) of the title compound as an off-white solid. LC/MS: m/z (ES−) 201 (M−H)⁻.

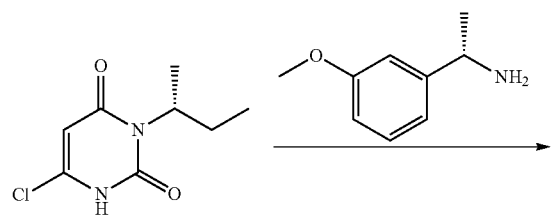

Compound 14. 3-(R)-sec-butyl-6-((S)-1-(3-methoxyphenyl)ethylamino)pyrimidine-2,4(1H,3H)-dione. A mixture 14.3 (150 mg, 0.74 mmol, 1.0 equiv.) in neat (S)-1-(3-methoxyphenyl)ethanamine (400 uL) was stirred overnight at 90° C. The reaction was purified using preparative RP-HPLC on an Agilent system with a gradient of 0-40% CH$_3$CN in H$_2$O over 45 min to yield 13 mg (6%) of the title compound as an off-white solid. LC/MS: m/z (ES+) 318 (M+H)⁺. $^1$H-NMR (400 MHz, DMSO-d$_6$): δ ppm 9.79 (s, 1H), 7.28 (t, J=8.1 Hz, 1H), 6.94-6.88 (m, 2H), 6.84 (dd, J=8.2, 1.7 Hz, 1H), 6.51 (d, J=6.4 Hz, 1H), 4.72-4.59 (m, 1H), 4.47 (m, 1H), 4.35 (s, 1H), 3.76 (s, 3H), 1.98-1.84 (m, 1H), 1.61 (m, 1H), 1.39 (d, J=6.7 Hz, 3H), 1.25 (d, J=6.9 Hz, 3H), 0.70 (t, J=7.4 Hz, 3H).

Example 15

Preparation of (S)-6-(1-phenylethylamino)-3-(pyridin-3-yl)-pyrimidine-2,4(1H,3H)-dione

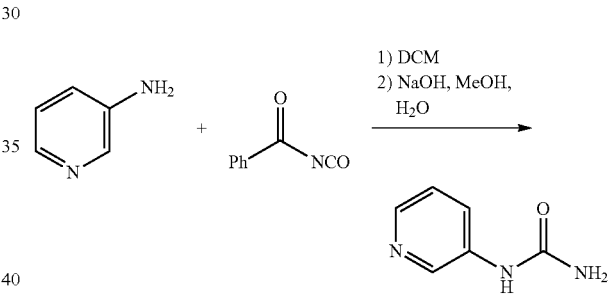

Compound 15.1. 1-(pyridin-3-yl)urea. Benzoyl isocyanate (3.28 g, 22.3 mmol, 1.05 equiv.) was taken up in CH$_2$Cl$_2$ (30 mL) and cooled to −10° C. Pyridin-3-amine (2 g, 21.2 mmol, 1 equiv.) was added in portions while stirring. The mixture was allowed to stir for 3 h at room temperature. After the reaction was deemed complete, it was concentrated and then taken up in a 1:1 mixture of CH$_3$OH and H$_2$O (100 mL) followed by the addition of NaOH (4.25 g, 106.3 mmol, 5 equiv.). The reaction was allowed to stir overnight at room temperature, concentrated to dryness, and then azeotroped three times with toluene. A mixture of 10% CH$_3$OH in EtOAc (100 mL) was added to the solid and stirred for 10 minutes followed by filtration. The solid was suspended and filtered two additional times. The combined filtrates were filtered once more to remove any solids that passed through the filter and concentrated. The residue was triturated with EtOAc (5 mL) and dried under vacuum to yield 3.5 g of crude material (off-white solid) that was utilized without further purification. LC/MS: m/z (ES+) 138 (M+H)⁺.

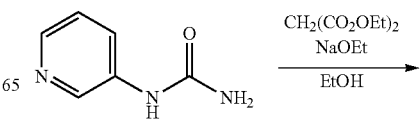

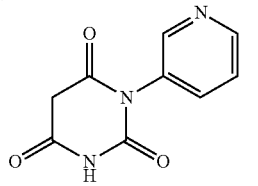

Compound 15.2. 1-(pyridin-3-yl)pyrimidine-2,4,6(1H,3H,5H)-trione. Compound 15.1 (3.0 g, 21.8 mmol, 1.0 equiv.) was taken up in EtOH (20 mL), followed by the addition of diethyl malonate (2.75 mL, 24.1 mmol, 1.1 equiv.), and NaOEt (8.5 mL, 26.3 mmol, 1.2 equiv.). The reaction was stirred at 85° C. overnight and then cooled to room temperature. Water (100 mL) was added slowly followed by careful addition of sodium bicarbonate (8 g). The resulting mixture was washed three times with EtOAc. The aqueous layer was concentrated to 50 mL and $CH_3OH$ (150 mL) was added. The precipitate was removed by filtration and the filtrate was concentrated. The resulting residue was purified flash chromatography (silica gel, 0-25% $CH_3OH$/$CH_2Cl_2$) to yield 1.70 g (38%) of the title compound as a light yellowish solid. LC/MS: m/z (ES+) 206 (M+H)$^+$.

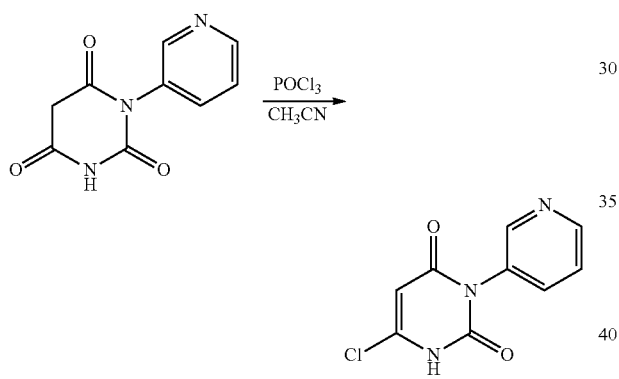

Compound 15.3. 6-chloro-3-(pyridin-3-yl)pyrimidine-2,4(1H,3H)-dione. A mixture of 15.2 (700 mg, 3.41 mmol, 1.0 equiv.) and $POCl_3$ (255 μL, 2.7 mmol, 0.8 equiv.) in $CH_3CN$ (10 mL) was stirred at 90° C. for 2 h. Additional $POCl_3$ (0.8 equiv) was added and stirring was continued at 90° C. for 2 h. Additional $POCl_3$ (1.6 equiv.) was added followed by the careful addition of $H_2O$ (150 ul 2.5 equiv.) The reaction was stirred overnight at 90° C. After cooling to room temperature, the mixture was filtered and the solid was carefully washed with $CH_3OH$ (1 mL). Ethyl acetate (20 mL) was added to the filtrate and the resulting precipitate was collected by filtration and dried under vacuum to yield 230 mg (30%) of the title compound as a light yellowish solid. LC/MS: m/z (ES+) 224 (M+H)$^+$.

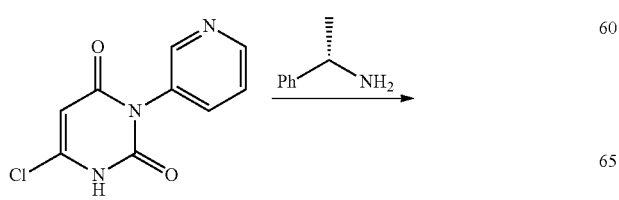

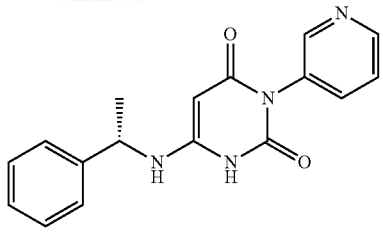

Compound 15. (S)-6-((1-phenylethylamino)-3-(pyridin-3-yl)pyrimidine-2,4(1H,3H)-dione. A mixture of 15.3 (100 mg, 0.45 mmol, 1 equiv.) in neat (5)-(−)-α-methylbenzylamine (500 uL) was stirred overnight at 100° C. After cooling, the reaction was purified using preparative RP-HPLC on an Agilent system with a gradient of 0-40% $CH_3CN$ in $H_2O$ over 45 min., followed by a second purification on a preparatory TLC plate (2000 um) with 7% $CH_3OH$/$CH_2Cl_2$ to yield 39.5 mg (28%) of the title compound. LC/MS: m/z (ES+) 309 (M+H)$^+$. $^1$H-NMR (400 MHz, DMSO-d$_6$): δ ppm 11.15 (s, 1H), 8.49 (dd, J=4.8, 1.4 Hz, 1H), 8.34 (d, J=2.4 Hz, 1H), 7.65-7.58 (m, 1H), 7.44 (dd, J=8.1, 4.8 Hz, 1H), 7.37 (m, 5H), 7.26 (m, 1H), 4.61-4.53 (m, 1H), 4.48 (s, 1H), 1.39 (d, J=6.8 Hz, 3H).

Example 16

Preparation of (S)-3-(Isoxazol-3-yl)-6-((1-phenylethylamino)pyrimidine-2,4(1H,3H)-dione (16)

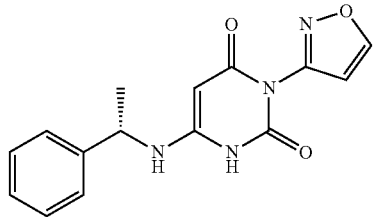 [SMILES: C[C@H](Nc1cc(=O)n(-c2ccon2)c(=O)[nH]1)c1ccccc1]

The title compound was prepared using procedures similar to those used for the preparation of compound 15 except isoxazol-3-amine was used in place of pyridin-3-amine. LC/MS: m/z (ES+) 299 (M+H)$^+$. $^1$H-NMR (400 MHz, DMSO-d$_6$): δ ppm 8.96 (s, 1H), 7.38 (d, J =3.9 Hz, 4H), 7.28 (dd, J=8.4, 4.3 Hz, 2H), 7.10 (s, 1H), 6.63 (s, 1H), 4.74-4.52 (m, 1H), 4.48 (s, 1H), 1.44 (d, J=6.6 Hz, 3H).

Example 17

Preparation of (S)-6-((1-(3-(1H-pyrazol-1-yl)phenyl)ethyl)amino)-3-isopropylpyrimidine-2,4(1H,3H)-dione (17)

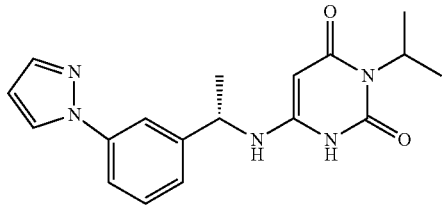 [SMILES: CC(C)n1c(=O)cc(N[C@@H](C)c2cccc(-n3cccn3)c2)[nH]c1=O]

The title compound was prepared by Ullman coupling (P. E. Fanta. "The Ullmann Synthesis of Biaryls". *Synthesis*, 1974, 9-21) of 35 with 1H-pyrazole in the presence of copper iodide, cesium carbonate, and trans-N,N'-dimethyl-cyclohexane-1,2-diamine. LC/MS: m/z (ES+) 340 (M+H)+. 
$^1$H-NMR (400 MHz, CD$_3$OD): δ ppm 8.26 (s, 1H), 7.70 (m, 2H), 7.66 (m, 1H), 7.51 (m, 1H), 7.34 (m, 1H), 6.55 (s, 1H), 5.05 (m, 1H), 4.62 (m, 1H), 1.58 (d, J=6.8 Hz, 3H), 1.37 (m, 6H).

Example 18

Preparation of Additional Pyrimidine Dione Compounds

The compounds in Table 1 were prepared according to the examples as described above.

TABLE 1

| Structure | Compound No. Ref. Example | Observed Mass and/or $^1$H NMR |
|---|---|---|
| | 19R<br>1 | 274 (M + H)+<br>$^1$H-NMR (400 MHz, CD$_3$OD): δ ppm 7.42-7.22 (m, 5H), 5.06-4.94 (m, 1H), 4.49 (m, 1H), 1.49 (d, J = 7.0 Hz, 3H), 1.36 (m, 6H). |
| | 20R<br>1 | 304 (M + H)+<br>$^1$H-NMR (400 MHz, CDCl$_3$): δ ppm 10.39 (br s, 1H), 7.29-7.23 (m, 1H), 6.88-6.79 (m, 3H), 5.31 (br s, 1H), 5.09 (m, 1H), 4.78 (br s, 1H), 4.48-4.34 (m, 1H), 3.80 (s, 3H), 1.51 (d, J = 7.0 Hz, 3H), 1.44-1.38 (m, 6H). |
| | 21<br>1 | 304 (M + H)+<br>$^1$H-NMR (400 MHz, CD$_3$OD): δ ppm 7.26 (t, J = 7.9 Hz, 1H), 6.92-6.85 (m, 2H), 6.85-6.80 (m, 1H), 5.01 (m ,1H), 4.45 (d, J = 7.0 Hz, 1H), 3.79 (s, 3H), 1.48 (d, J = 7.0 Hz, 3H), 1.37 (d, J = 7.0 Hz, 6H). |
| | 22<br>1 | 304 (M + H)+<br>$^1$H-NMR (400 MHz, CD$_3$OD): δ ppm 7.29-7.17 (m, 1 H), 7.00 (d, J = 7.4 Hz, 1 H), 6.93 (m, 1 H), 5.05-4.97 (m, 1 H), 4.83 (s, 1 H), 4.80-4.74 (m, 1 H), 3.89 (s, 3 H), 1.45 (d, J = 6.7 Hz, 3 H), 1.38-1.34 (m, 6 H). |
| | 24<br>1 | 288 (M + H)+<br>$^1$H-NMR (400 MHz, DMSO-d$_6$): δ ppm 9.76 (br s, 1H), 7.41-7.13 (m, 5H), 6.50 (d, J = 7.0 Hz, 1H), 4.88 (m, 1H), 4.31 (d, J = 2.4 Hz, 1H), 4.24 (m, 1H), 1.83-1.58 (m, 2H), 1.35-1.10 (m, 6H), 0.83 (m, 3H). |

TABLE 1-continued

Compounds and Analytical Data

| Structure | Compound No. Ref. Example | Observed Mass and/or ¹H NMR |
|---|---|---|
| | 25<br>1 | 288 (M + H)⁺<br>¹H-NMR (400 MHz, DMSO-d₆): δ ppm 7.46-7.29 (m, 4H), 7.27-7.21 (m, 1H), 6.27 (d, J = 9.0 Hz, 1H), 6.08 (br s, 1H), 5.13 (m, 1H), 4.98 (m, 1H), 1.78 (s, 3H), 1.46 (m, 3H), 1.29 (m, 6H). |
| | 26<br>1 | 292 (M + H)⁺<br>¹H-NMR (400 MHz, CDCl₃): δ ppm 10.45 (br s, 1H), 7.30-7.23 (m, 2H), 7.16-7.01 (m, 2H), 5.13 (dt, J = 13.8, 7.0 Hz, 1H), 4.99 (br s, 1H), 4.74-4.63 (m, 2H), 1.55 (d, J = 6.7 Hz, 3H), 1.43 (m, 6H). |
| | 27<br>1 | 292 (M + H)⁺<br>¹H-NMR (400 MHz, CDCl₃): δ ppm 10.28 (br s, 1H), 7.36-7.28 (m, 1H), 7.06 (d, J = 7.8 Hz, 1H), 7.02-6.93 (m, 2H), 5.17-5.04 (m, 1H), 4.95-4.82 (m, 1H), 4.75-4.70 (m, 1H), 4.50-4.40 (m, 1H), 1.53 (d, J = 7.0 Hz, 3H), 1.46-1.37 (m, 6H). |
| | 28<br>1 | 308 (M + H)⁺<br>¹H NMR (400 MHz, CD₃OD): δ ppm 7.39-7.31 (m, 2H), 7.29-7.23 (m, 2H), 5.01 (m, 1H), 4.50 (q, J = 6.7 Hz, 1H), 1.48 (d, J = 7.0 Hz, 3H), 1.37 (d, J = 7.0 Hz, 6H). |
| | 29<br>1 | 304 (M + H)⁺<br>¹H NMR (400 MHz, CD₃OD): δ ppm 7.38-7.26 (m, 5H), 5.04-4.97 (m, 1H), 4.56 (dd, J = 7.4, 3.9 Hz, 1H), 3.67-3.63 (m, 1H), 3.56-3.51 (m, 1H), 3.37 (s, 3H), 1.36 (m, 6H). |
| | 30<br>1 | 292 (M + H)⁺<br>¹H-NMR (400 MHz, CD₃OD): δ ppm 7.34 (m, 2H), 7.08 (m, 2H), 5.07-4.95 (m, 1H), 4.50 (q, J = 6.8 Hz, 1H), 1.48 (d, J = 6.7 Hz, 3H), 1.37 (m, 6H). |

TABLE 1-continued

Compounds and Analytical Data

| Structure | Compound No. Ref. Example | Observed Mass and/or $^1$H NMR |
|---|---|---|
| 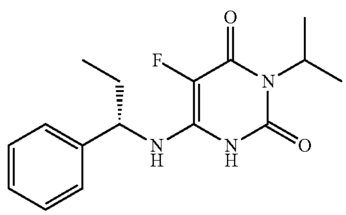 [SMILES: CC[C@H](Nc1[nH]c(=O)n(C(C)C)c(=O)c1F)c1ccccc1] | 31<br>4 & 5 | 306 (M + H)$^+$<br>$^1$H-NMR (400 MHz, CDCl$_3$): δ ppm 9.70 (br s, 1H), 7.39-7.22 (m, 5H), 5.19-5.07 (m, 1H), 4.85 (br s, 1H), 4.73-4.61 (m, 1H), 1.88 (dq, J = 14.3, 7.0 Hz, 2H), 1.45 (m, 6H), 0.96 (t, J = 7.4 Hz, 3H). |
| 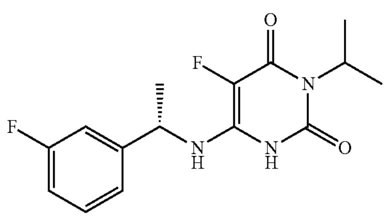 [SMILES: CC(C)n1c(=O)[nH]c(N[C@@H](C)c2cccc(F)c2)c(F)c1=O] | 32<br>4 & 5 | 310 (M + H)$^+$<br>$^1$H-NMR (400 MHz, CDCl$_3$): δ ppm 9.89 (br s, 1 H), 7.40-7.29 (m, 1 H), 7.13-6.95 (m, 3 H), 5.12 (m, 1 H), 5.02-4.87 (m, 1 H), 4.82-4.69 (m, 1 H), 1.59 (d, J = 6.7 Hz, 3 H), 1.42 (m, 6 H), |
| 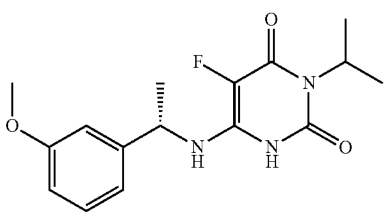 [SMILES: COc1cccc([C@H](C)Nc2[nH]c(=O)n(C(C)C)c(=O)c2F)c1] | 33<br>4 & 5 | 322 (M + H)$^+$<br>$^1$H-NMR (400 MHz, CDCl$_3$): δ ppm 9.50 (br s, 1H), 7.30 (dd, J = 9.00, 7.83 Hz, 1H), 6.93-6.90 (m, 3H), 5.19-5.04 (m, 1H), 4.88 (m, 1H), 4.75 (m, 1H), 3.79 (s, 3H), 1.59 (d, J = 6.7 Hz, 3H), 1.43 (d, J = 7.0 Hz, 6H). |
| 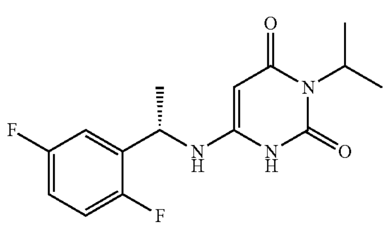 [SMILES: CC(C)n1c(=O)cc(N[C@@H](C)c2cc(F)ccc2F)[nH]c1=O] | 34<br>6 | 310 (M + H)$^+$<br>$^1$H-NMR (300 MHz, DMSO-d$_6$): δ ppm 9.74 (s, 1H), 7.32-7.24 (m, 2H), 7.21-7.13 (m, 1H), 6.60 (s, 1H), 4.95-4.86 (m, 1H), 4.69-4.62 (m, 1H), 4.32 (s, 1H), 1.49-1.42 (d, J = 6.6 Hz, 3H), 1.28-1.26 (d, J = 6.9 Hz, 6H). |
| 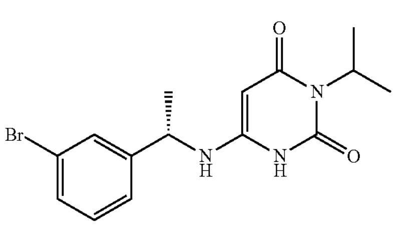 | 35<br>6 | 352 (M + H)$^+$<br>$^1$H-NMR (300 MHz, DMSO-d$_6$): δ ppm 9.85 (s, 1H), 7.59 (s, 1H), 7.48 (m, 1H), 7.38-7.32 (m, 2H), 6.59 (d, J = 5.4 Hz, 1H), 4.95-4.88 (m, 1H), 4.57-4.50 (m, 1H), 4.36 (s, 1H), 1.41 (d, J = 6.6 Hz, 3H), 1.25 (d, J = 6.9 Hz, 6H). |
| 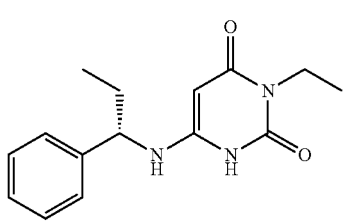 [SMILES: CC[C@H](Nc1cc(=O)n(CC)c(=O)[nH]1)c1ccccc1] | 36<br>1 & 5 | 274 (M + H)$^+$<br>$^1$H-NMR (300 MHz, DMSO-d$_6$): δ ppm 9.96 (br s, 1H), 7.39-7.24 (m, 5H), 6.58 (d, J = 6.6 Hz, 1H), 4.38 (s, 1H), 4.28 (q, J = 6.9 Hz, 1H), 3.65 (q, J = 6.6 Hz, 2H), 1.78-1.66 (m, 2H), 0.99 (t, J = 6.9 Hz, 3H), 0.86 (t, J = 7.2 Hz, 3H). |

TABLE 1-continued

Compounds and Analytical Data

| Structure | Compound No. Ref. Example | Observed Mass and/or ¹H NMR |
|---|---|---|
| 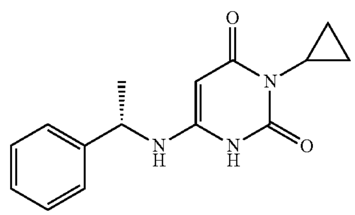 [SMILES: C[C@H](Nc1cc(=O)n(C2CC2)c(=O)[nH]1)c1ccccc1] | 37<br>1 & 5 | 272 (M + H)⁺<br>¹H-NMR (400 MHz, DMSO-d₆): δ ppm 9.83 (s, 1H), 7.37 (m, 4H), 7.26 (m, 1H), 6.52 (m, 1H), 4.50 (m, 1H), 4.33 (s, 1H), 2.37 (m, 1H), 1.41 (d, J = 6.8 Hz, 3H), 0.85 (m, 2H), 0.60 (m, 2H). |
| 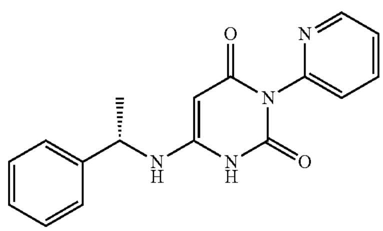 [SMILES: C[C@H](Nc1cc(=O)n(-c2ccccn2)c(=O)[nH]1)c1ccccc1] | 38<br>15 | 309 (M + H)⁺<br>¹H-NMR (400 MHz, DMSO-d₆): δ ppm 10.92 (s, 1H), 8.57-8.42 (m, 1H), 7.85 (ddd, J = 7.8, 7.8, 1.7 Hz, 1H), 7.46-7.31 (m, 5H), 7.32-7.19 (m, 2H), 7.13 (m, 1H), 4.67-4.52 (m, 1H), 4.41 (s, 1H), 1.39 (d, J = 6.8 Hz, 3H). |
| 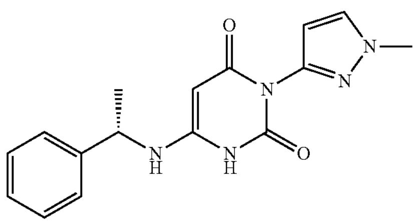 [SMILES: C[C@H](Nc1cc(=O)n(-c2ccn(C)n2)c(=O)[nH]1)c1ccccc1] | 39<br>15 | 312 (M + H)⁺<br>¹H-NMR (400 MHz, DMSO-d₆): δ ppm 7.65 (d, J = 2.2 Hz, 1H), 7.41-7.35 (m, 5H), 7.32-7.24 (m, 2H), 6.77 (d, J = 5.9 Hz, 1H), 6.04 (d, J = 2.1 Hz, 1H), 4.63-4.55 (m, 1H), 4.42 (s, 1H), 3.79 (s, 3H), 1.44 (d, J = 6.7 Hz, 3H). |
| 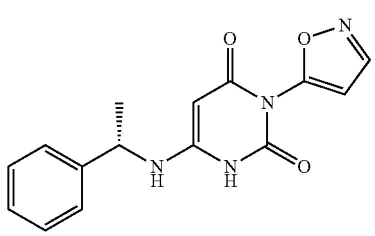 [SMILES: C[C@H](Nc1cc(=O)n(-c2ccno2)c(=O)[nH]1)c1ccccc1] | 40<br>15 | 299 (M + H)⁺<br>¹H-NMR (400 MHz, DMSO-d₆): δ ppm 11.07 (s, 1H), 8.93 (s, 1H), 7.43-7.31 (m, 4H), 7.31-7.04 (m, 2H), 6.59 (s, 1H), 4.62 (m, 1H), 4.43 (s, 1H), 1.40 (d, J = 6.7 Hz, 3H). |
| 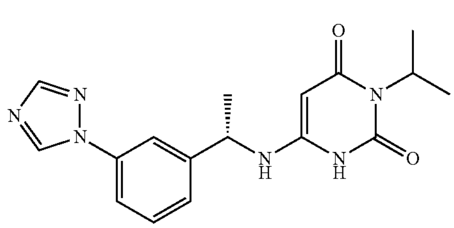 [SMILES: CC(C)n1c(=O)cc(N[C@@H](C)c2cccc(-n3cncn3)c2)[nH]c1=O] | 41<br>17 | 341 (M + H)⁺<br>¹H-NMR (400 MHz, CDCl₃): δ ppm 10.42 (s, 1H), 8.67 (s, 1H), 8.13 (s, 1H), 7.71 (s, 1H), 7.61 (m, 1H), 7.51 (m, 1H), 7.37 (m, 1H), 5.41 (m, 1H), 5.13 (m, 1H), 4.68 (m, 1H), 4.55 (m, 1H), 1.59 (d, J = 6.8 Hz, 3H), 1.44 (m, 6H). |
| 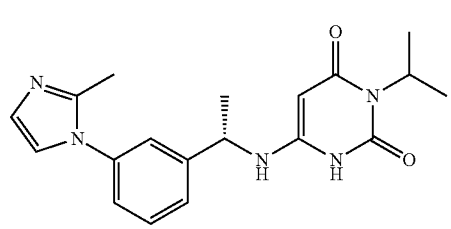 [SMILES: Cc1nccn1-c1cccc([C@H](C)Nc2cc(=O)n(C(C)C)c(=O)[nH]2)c1] | 42<br>17 | 354 (M + H)⁺<br>¹H-NMR (400 MHz, DMSO-d₆): δ ppm 9.85 (s, 1H), 7.52 (m, 1H), 7.39 (m, 2H), 7.34 (m, 2H), 6.94 (m, 1H), 6.60 (m, 1H), 4.90 (m, 1H), 4.62 (m, 1H), 4.38 (s, 1H), 2.26 (s, 3H), 1.44 (d, J = 9.2 Hz, 3H), 1.28 (d, J = 9.2 Hz, 6H). |

TABLE 1-continued

Compounds and Analytical Data

| Structure | Compound No. Ref. Example | Observed Mass and/or ¹H NMR |
|---|---|---|
| 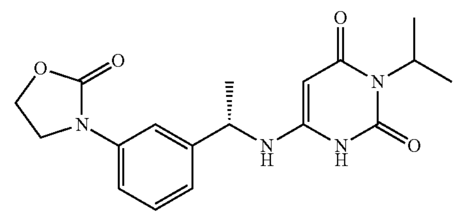 [SMILES: CC(C)n1c(=O)cc(N[C@@H](C)c2cccc(N3CCOC3=O)c2)[nH]c1=O] | 43<br>17 | 359 (M + H)⁺<br>¹H-NMR (400 MHz, DMSO-d₆): δ ppm 9.84 (s, 1H), 7.62 (s, 1H), 7.42 (m, 2H), 7.12 (d, J = 7.2 Hz, 1H), 6.61 (bs, 1H), 4.91 (m, 1H), 4.69-4.43 (m, 3H), 4.34 (s, 1H), 4.09 (m, 2H), 1.42 (d, J = 6.8 Hz, 3H), 1.28 (m, 6H). |
| 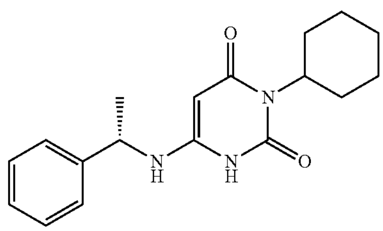 [SMILES: C[C@H](Nc1cc(=O)n(C2CCCCC2)c(=O)[nH]1)c1ccccc1] | 44<br>15 | 314 (M + H)⁺<br>¹H-NMR (400 MHz, CD₃OD): δ ppm 7.28-7.13 (m, 5H), 4.52 (m, 1H), 4.39 (m, 2H), 2.22 (m, 2H), 1.69 (m, 2H), 1.54 (m, 1H), 1.44-1.40 (m, 2H), 1.40 (d, J = 67 Hz, 3H), 1.30-1.20 (m, 2H), 1.20-1.08 (m, 1H). |
| 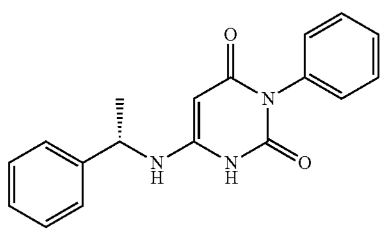 [SMILES: C[C@H](Nc1cc(=O)n(-c2ccccc2)c(=O)[nH]1)c1ccccc1] | 45<br>15 | 308 (M + H)⁺<br>¹H-NMR (400 MHz, CDCl₃): δ ppm 9.84 (s, 1H), 7.43-7.17 (m, 6H), 7.12 (d, J = 7.3 Hz, 2H), 7.05 (d, J = 6.8 Hz, 2H), 5.55 (br s, 1H), 4.68 (s, 1H), 4.25 (m, 1H), 1.18 (d, J = 6.7 Hz, 3H). |
| 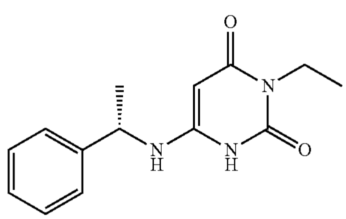 [SMILES: CCn1c(=O)cc(N[C@@H](C)c2ccccc2)[nH]c1=O] | 46<br>15 | 260 (M + H)⁺<br>¹H-NMR (400 MHz, CD₃OD): δ ppm 7.37-7.30 (m, 4H), 7.10-7.06 (m, 1H), 4.55 (s, 1H), 4.51 (q, J = 6.7 Hz, 1H), 3.81 (q, J = 7.0 Hz, 2H), 1.50 (d, J = 7.0 Hz, 3H), 1.11 (t, J = 7.0 Hz, 3H). |
| 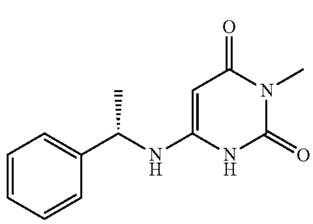 [SMILES: C[C@H](Nc1cc(=O)n(C)c(=O)[nH]1)c1ccccc1] | 47<br>15 | 246 (M + H)⁺<br>¹H-NMR (400 MHz, DMSO-d₆): δ ppm 10.02 (s, 1H), 7.38-7.30 (m, 4H), 7.26-7.22 (m, 1H), 6.56 (s, 1H), 4.52 (q, J = 6.7 Hz, 1H), 4.39 (s, 1H), 2.97 (s, 3H) 1.40 (d, J = 6.7 Hz, 3H). |

Example 48

Preparation of (S)-6-((1-phenylethyl)-amino-3-propylpyrimidine-2,4-(1H,3H)-dione

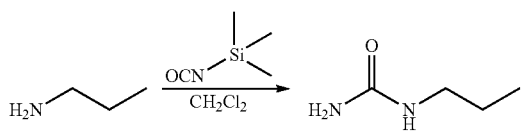

Compound 48.1. 1-propylurea. To a stirred solution of n-propylamine (2.15 g, 36.5 mmol, 1.00 equiv) in CH₂Cl₂ (35 mL) at 0° C. was added dropwise trimethylsilyl isocyanate (4.94 g (85% purity), 36.5 mmol, 1.00 equiv). The reaction mixture was stirred at room temperature for 72 h and was then cooled to 0° C. The chilled mixture was quenched by the dropwise addition of CH₃OH (10 mL) and was concentrated under reduced pressure. The resulting solid was suspended in Et₂O (30 mL) and was filtered. The solid was further washed with Et₂O (30 mL) and dried to afford 2.0 g (38%) of the title compound as a white solid.

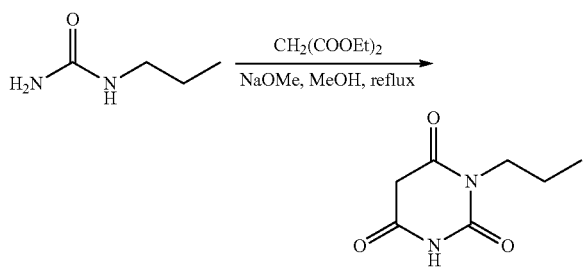

Compound 48.2. 1-propylpyrimidine-2,4,6(1H,3H,5H)-trione. To 48.1 (600 mg, 5.88 mmol, 1.00 equiv) in CH$_3$OH (1 mL) was added diethyl malonate (960 mg, 6.0 mmol, 1.02 equiv.) and sodium methoxide (1 mL, 25% NaOCH$_3$ in CH$_3$OH by weight). The reaction mixture was heated in the microwave reactor at 130° C. for 1 h. The mixture was cooled and the mixture was carefully adjusted to pH=3 with concentrated HCl. The volatiles were removed and H$_2$O was added (10 mL). Solid precipitated and was filtered. It was further washed with additional H$_2$O (10 mL) and dried to afford 560 mg (56%) of title compound as a white solid.

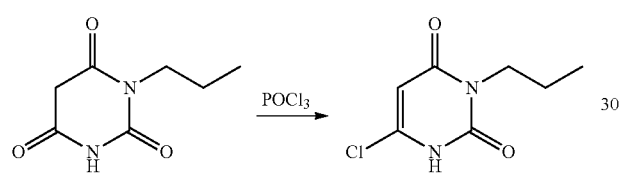

Compound 48.3. 6-chloro-3-propylpyrimidine-2,4(1H,3H)-dione. Compound 48.2 (560 mg, 3.30 mmol) and POCl$_3$ (2 mL) were added to a heavy wall pressure vessel which was subsequently sealed. The resulting solution was heated to 70° C. and stirred for 50 minutes behind a blast shield. The reaction mixture was cooled and concentrated under reduced pressure. To the resulting residue was added CH$_2$Cl$_2$ (30 mL) which was then removed under reduced pressure. The addition and evaporation of CH$_2$Cl$_2$ (30 mL) was conducted one additional time and then the resulting residue was diluted with CH$_2$Cl$_2$ (50 mL). To the organic layer was carefully added a saturated aqueous NaHCO$_3$ solution (50 mL). The layers were separated and the organics were further washed with H$_2$O (30 mL) and brine (30 mL). The organic layer was concentrated and purified by flash column chromatography (silica gel, utilizing 10% EtOAc in CH$_2$Cl$_2$) to afford 160 mg (26%) of the title compound as a white solid.

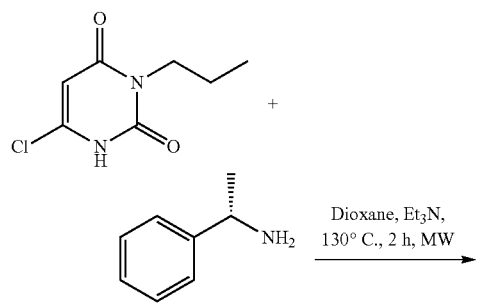

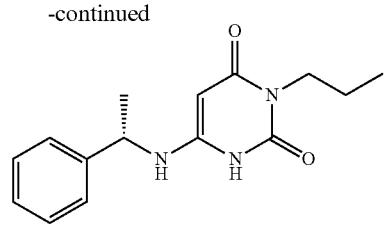

Compound 48. (S)-6-((1-phenylethyl)amino)-3-propylpyrimidine-2,4(1H,3H)-dione. To 48.3 (160 mg, 0.85 mmol, 1.0 equiv.) in 1,4-dioxane (1.5 mL) was added Et$_3$N (200 µL) and (S)-α-methylbenzylamine (235 mg, 1.94 mmol, 2.3 equiv.). The mixture was heated in a microwave reactor at 130° C. for 2 h. The mixture was cooled and concentrated. The resulting residue was treated with an 8:3 mixture of H$_2$O:CH$_3$CN which resulted in precipitation. The solid was filtered and successively washed with H$_2$O (10 mL) and EtOAc (10 mL). The solid was dried to give 67 mg (29%) of the title compound as a white solid. LC/MS: m/z (ES+) 274 (M+H)$^+$. $^1$H-NMR (400 MHz, DMSO-d$_6$): δ ppm 9.92 (br s, 1H), 7.36-7.22 (m, 5H), 6.54 (d, J=7.0 Hz, 1H), 4.50 (quin, J=6.7 Hz, 1H), 4.35 (s, 1H), 3.54 (dd, J=8.0, 6.9 Hz, 2H), 1.42-1.36 (m, 5H), 0.76 (t, J=7.6 Hz, 3H).

Example 49

Preparation of (S)-3-(3,5-difluorophenyl)-6-((1-phenylethyl)amino)pyrimidine-2,4(1H,3H)-dione

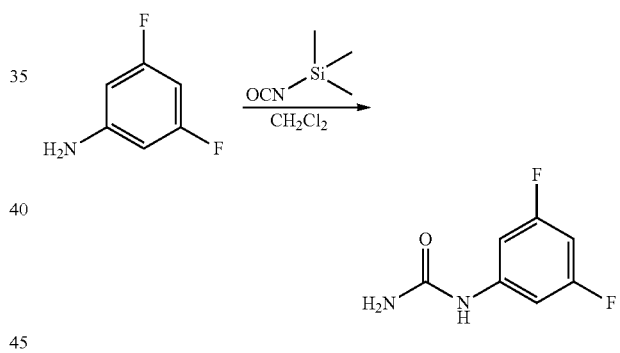

Compound 49.1. 1-(3,5-difluorophenyl)urea. To a stirred solution of 3,5-difluoroaniline (4.0 g, 31 mmol, 1.00 equiv) in CH$_2$Cl$_2$ (50 mL) under argon at room temperature was added dropwise trimethylsilyl isocyanate (3.56 g, 30.90 mmol, 1.00 equiv). The reaction mixture was stirred overnight and quenched by the dropwise addition of CH$_3$OH (50 mL). The reaction mixture was concentrated under reduced pressure and the resulting residue was purified by flash chromatography (silica gel, eluting with CHCl$_3$/CH$_3$OH (10:1 to 7:1)) to yield 2.0 g (38%) of the title compound as a white solid. $^1$H-NMR (400 MHz, DMSO-d$_6$): δ ppm 8.96 (s, 1H), 7.16-7.10 (m, 2H), 6.72-6.66 (m, 1H), 6.07 (br s, 2H).

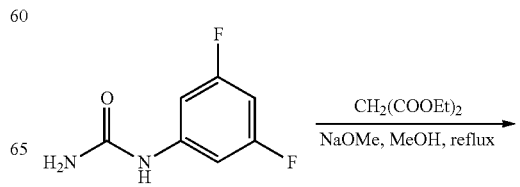

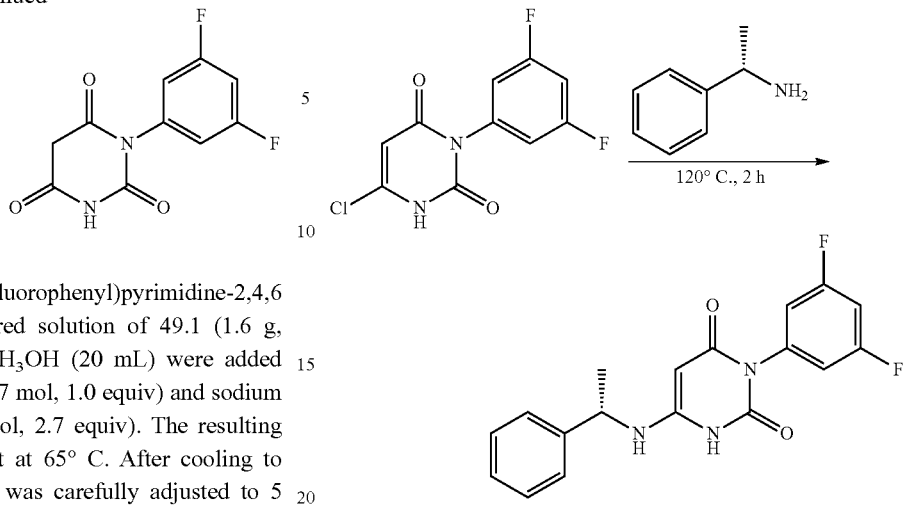

Compound 49.2. 1-(3,5-difluorophenyl)pyrimidine-2,4,6 (1H,3H,5H)-trione. To a stirred solution of 49.1 (1.6 g, 0.0093 mol, 1.1 equiv) in CH₃OH (20 mL) were added diethyl malonate (1.4 g, 0.0087 mol, 1.0 equiv) and sodium methoxide (1.25 g, 0.0231 mol, 2.7 equiv). The resulting mixture was stirred overnight at 65° C. After cooling to ambient temperature, the pH was carefully adjusted to 5 using aqueous 1N HCl. The resulting solution was extracted with EtOAc (3×50 mL). The organic layers were combined and concentrated under reduced pressure. The residue was washed with CH₃OH (50 mL) and the resulting solid was isolated by filtration to give 700 mg (31%) of the title compound as a white solid. ¹H-NMR (400 MHz, DMSO-d₆): δ ppm 11.66 (s, 1H), 7.43-7.35 (m, 1H), 7.11-7.08 (m, 2H), 3.77 (s, 2H).

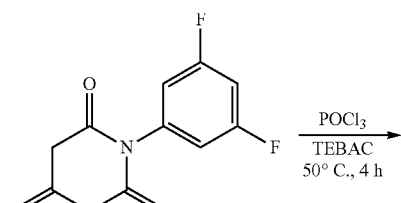

Compound 49.3. 6-chloro-3-(3,5-difluorophenyl)pyrimidine-2,4(1H,3H)-dione. To a 25-mL round-bottom flask under argon containing 49.2 (740 mg, 3.08 mmol, 1.00 equiv) were added triethylbenzylammonium chloride (840 mg, 1.20 equiv) and POCl₃ (3 mL). The resulting solution was stirred for 4 h at 50° C. The reaction cooled and quenched by the careful addition of water/ice (20 mL). The pH of the solution was adjusted to 5 with 2N sodium hydroxide. The resulting solution was extracted with EtOAc (2×10 mL) and the organic layers were combined. The organic layer was washed with brine (10 mL), dried over anhydrous MgSO₄, filtered, and concentrated under reduced pressure. This resulted in 500 mg (crude) of the title compound as a white solid. ¹H-NMR (400 MHz, DMSO-d₆): δ ppm 12.60 (br, 1H), 7.38-7.32 (m, 1H), 7.21-7.16 (m, 2H), 6.05 (s, 1H).

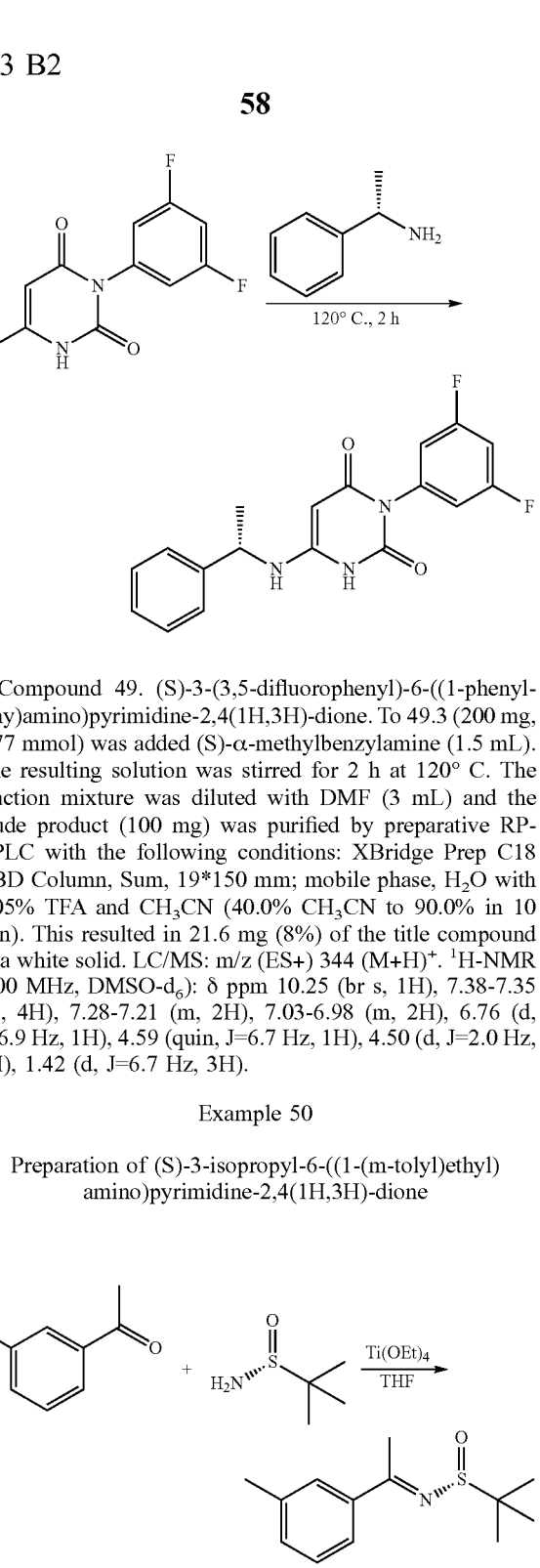

Compound 49. (S)-3-(3,5-difluorophenyl)-6-((1-phenylethy)amino)pyrimidine-2,4(1H,3H)-dione. To 49.3 (200 mg, 0.77 mmol) was added (S)-α-methylbenzylamine (1.5 mL). The resulting solution was stirred for 2 h at 120° C. The reaction mixture was diluted with DMF (3 mL) and the crude product (100 mg) was purified by preparative RP-HPLC with the following conditions: XBridge Prep C18 OBD Column, Sum, 19*150 mm; mobile phase, H₂O with 0.05% TFA and CH₃CN (40.0% CH₃CN to 90.0% in 10 min). This resulted in 21.6 mg (8%) of the title compound as a white solid. LC/MS: m/z (ES+) 344 (M+H)⁺. ¹H-NMR (300 MHz, DMSO-d₆): δ ppm 10.25 (br s, 1H), 7.38-7.35 (m, 4H), 7.28-7.21 (m, 2H), 7.03-6.98 (m, 2H), 6.76 (d, J=6.9 Hz, 1H), 4.59 (quin, J=6.7 Hz, 1H), 4.50 (d, J=2.0 Hz, 1H), 1.42 (d, J=6.7 Hz, 3H).

Example 50

Preparation of (S)-3-isopropyl-6-((1-(m-tolyl)ethyl)amino)pyrimidine-2,4(1H,3H)-dione Compound 50.1. (R,E)-2-methyl-N-(1-(m-tolyl)ethylidene)propane-2-sulfinamide. To a stirred solution of 1-(3-methylphenyl)ethanone (1.61 g, 12.0 mmol, 1.00 equiv.) and (R)-(+)-2-methyl-2-propanesulfinamide (1.94 g, 14 mmol, 1.33 equiv.) in THF (50 mL) was added Ti(OEt)₄ (3.19 g, 14 mmol, 1.17 equiv.) dropwise. The reaction mixture was stirred for 16 h at 60° C., cooled to room temperature, and quenched with a saturated aqueous NaHCO₃ solution (50 mL). The layers were separated and the aqueous layer was further extracted with EtOAc (2×100 mL). The combined organics were concentrated and the resulting residue was purified by flash chromatography (silica gel, eluting with 0-5% CH$_3$OH in CH$_2$Cl$_2$) to afford 1.51 g (53%) of the title compound as a white solid. LC/MS: m/z (ES+) 238 (M+H)$^+$.

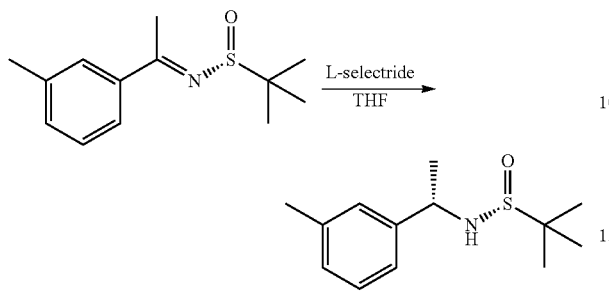

Compound 50.2. (R)-2-methyl-N—((S)-1-(m-tolyl)ethyl)propane-2-sulfinamide. To a solution of 50.1 (1.51 g, 6.37 mmol) in THF (30 mL) at −78° C. under an N$_2$ atmosphere was added L-selectride (dropwise, 10 mL, 1.0 M in THF, 10 mmol). The reaction mixture was warmed to 0° C., stirred for 1 h, and carefully quenched with a saturated aqueous NH$_4$Cl solution (30 mL). The layers were separated and the aqueous layer was further extracted with EtOAc (2×50 mL). The combined organics were concentrated and the resulting residue was purified by flash chromatography (silica gel, eluted with 0-5% CH$_3$OH in CH$_2$Cl$_2$) to afford 0.85 g (56%) of the title compound. LC/MS: m/z (ES+) 240 (M+H)$^+$.

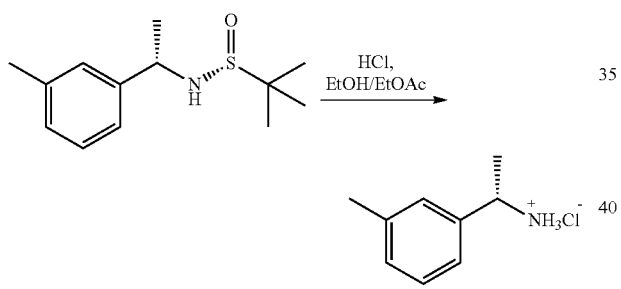

Compound 50.3. (S)-1-(m-tolyl)ethan-1-amine hydrochloride. To absolute EtOH (10 mL) was added AcCl (1.5 mL, dropwise). The mixture was stirred for 10 minutes and then was added to 50.2 (0.85 g, 3.56 mmol) in EtOH (3 mL). The reaction mixture was stirred for 2 h at ambient temperature and was concentrated. The resulting solid was suspended in Et$_2$O and filtered. The solid was washed with additional Et$_2$O and dried to give 402 mg (66%) of the title compound as white solid. LC/MS: m/z (ES+) 136 (M+H)$^+$.

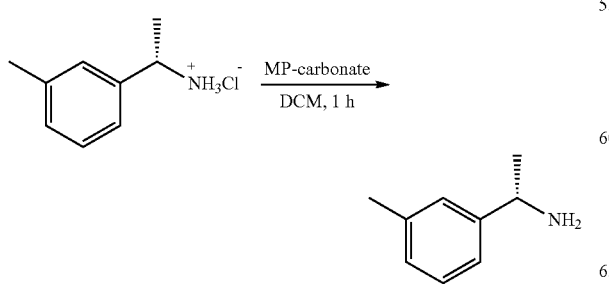

Compound 50.4. (S)-1-(m-tolyl)ethan-1-amine. To a stirred solution of 50.3 (205 mg, 1.20 mmol) in CH$_2$Cl$_2$ (10 mL) was added MP-carbonate (1.0 g, 3.18 mmol/g). The reaction mixture was stirred at room temperature for 1 h and was then filtered. The solid beads were washed with an additional 10 mL CH$_2$Cl$_2$ and the combined filtrates were concentrated to give the title compound which was pushed forward without any purification.

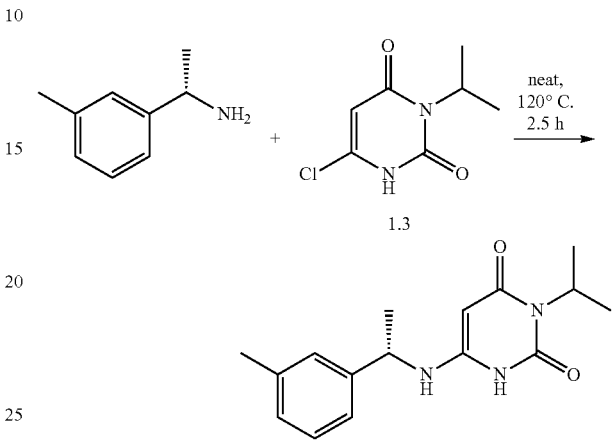

Compound 50. (S)-3-isopropyl-6-((1-(m-tolyl)ethyl)amino)pyrimidine-2,4(1H,3H)-dione. To 50.4 (presumed ~1.2 mmol from previous reaction, 2.0 equiv.) in a 0.5 to 2.0 mL microwave tube was added compound 1.3 (110 mg, 0.59 mmol, 1.0 equiv.). The microwave tube was sealed and heated at 120° C. behind a blast shield for 2.5 h. Upon cooling (to ~60° C.), NMP (2.5 mL) was added to the reaction mixture. The mixture was sonicated and heated (to ~60° C.) until the solid completely dissolved. The resulting solution was cooled to 40° C. and a 3:1 mixture of H$_2$O/CH$_3$CN (5 mL) was added. A solid precipitated and was collected through filtration. The light beige solid was subsequently washed with H$_2$O and dried to give 97 mg (57%) of the title compound as a white solid. LC/MS: m/z (ES+) 288 (M+H)$^+$. $^1$H-NMR (400 MHz, DMSO-d$_6$): δ ppm 9.73 (br s, 1H), 7.22 (t, J=8.0 Hz, 1H), 7.12-7.04 (m, 3H), 6.45 (d, J=8.0 Hz, 1H), 4.90-4.86 (m, 1H), 4.42 (q, J=6.7 Hz, 1H), 4.31 (d, J=2.4 Hz, 1H), 2.29 (s, 3H), 1.36 (d, J=6.7 Hz, 3H), 1.27-1.23 (m, 6H).

Example 51

Preparation of (S)-6-((1-(4-fluorophenyl)propan-2-yl)amino)-3-isopropylpyrimidine-2,4(1H,3H)-dione

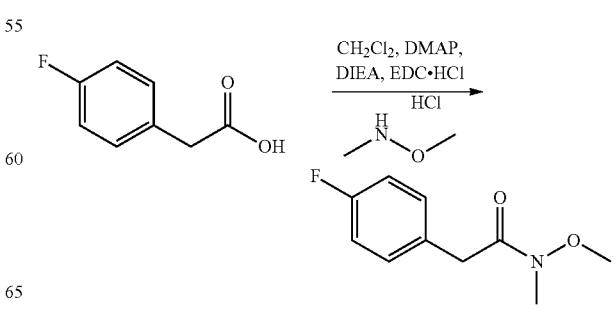

Compound 51.1. 2-(4-fluorophenyl)-N-methoxy-N-methylacetamide. To a stirred solution of 2-(4-fluorophenyl)acetic acid (15 g, 97.32 mmol, 1.00 equiv) in CH₂Cl₂ (300 mL) was added methoxy(methyl)amine hydrochloride (11.1 g, 113.79 mmol, 1.20 equiv), 4-dimethylaminopyridine (12 g, 98.22 mmol, 1.00 equiv), 1-Ethyl-3-(3-dimethylaminopropyl) carbodiimide hydrochloride (28.2 g, 147.10 mmol, 1.50 equiv), and DIEA (37.5 g, 290.14 mmol, 3.00 equiv). The resulting solution was stirred at room temperature for 16 h and then diluted with EtOAc (150 mL). The organics were washed with aqueous 1N HCl (2×150 mL) and brine (2×150 mL). It was then dried over anhydrous Na₂SO₄ and concentrated under reduced pressure. The crude residue was purified by flash chromatography (silica gel, eluting with EtOAc/petroleum ether (1:3)). This resulted in 18 g (88%) of the title compound as yellow oil. ¹H-NMR (400 MHz, CDCl₃): δ ppm 7.29-7.25 (m, 2H), 7.03-6.99 (m, 2H), 3.75 (s, 2H), 3.65 (s, 3H), 3.21 (s, 3H).

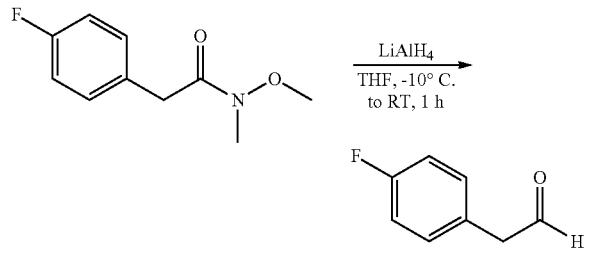

Compound 51.2. 2-(4-fluorophenyl)acetaldehyde. To a stirred solution of 51.1 (3 g, 15.21 mmol, 1.00 equiv) in THF (60 mL) under argon at −10° C. was added LiAlH₄ (1.15 g, 30.30 mmol, 2.00 equiv) in several batches (CAREFUL . . . EXOTHERMIC REACTION). The resulting solution was stirred for 1 h at room temperature before being cooled to −10° C. The reaction was then quenched by the careful addition of a saturated aqueous NH₄Cl solution (50 mL). The resulting solid was filtered and the filtrate was extracted with EtOAc (3×50 mL). The organic layers were combined, washed with brine (50 mL), dried with anhydrous Na₂SO₄ and concentrated under reduced pressure to give 2.5 g (crude) of the title compound as a yellow oil.

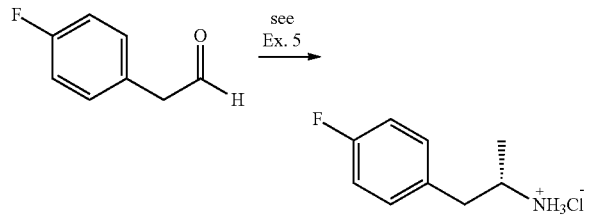

Compound 51.3. (S)-1-(4-fluorophenyl)propan-2-amine hydrochloride. The title compound was synthesized according to methods described for the preparation of 5.3, utilizing 51.2 in place of 3,5-difluorobenzaldehyde. LC/MS: m/z (ES+) 154 (M+H)⁺.

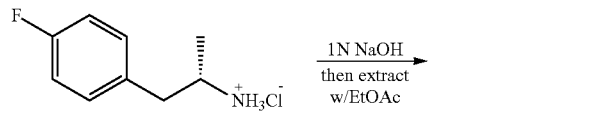

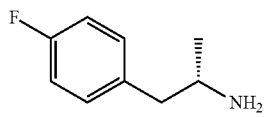

Compound 51.4. (S)-1-(4-fluorophenyl)propan-2-amine. To an aqueous solution of 1N NaOH (5 mL) was added 51.3 (300 mg, 1.59 mmol). The resulting mixture was stirred for one hour at 25° C. The resulting solution was extracted with EtOAc (2×10 mL). The organic layer was dried over anhydrous sodium sulfate and concentrated under reduced pressure to yield 160 mg (65%) of the title compound. LC/MS: m/z (ES+) 154 (M+H)⁺.

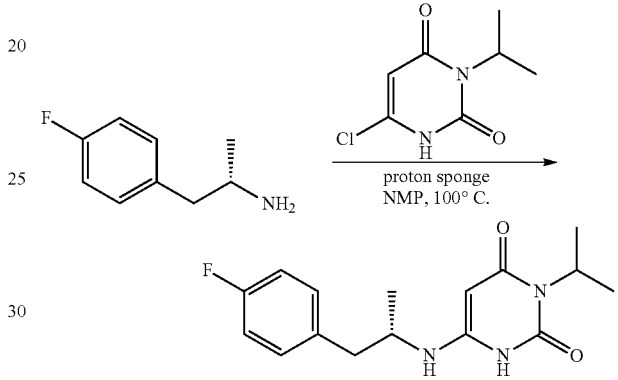

Compound 51. (S)-6-((1-(4-fluorophenyl)propan-2-yl)amino)-3-isopropylpyrimidine-2,4(1H,3H)-dione. To a stirred solution of 51.4 (160 mg, 1.04 mmol, 2.00 equiv) in NMP (0.5 mL) was added 1.3 (99 mg, 0.52 mmol, 1.00 equiv) and proton sponge (168 mg, 0.78 mmol, 1.50 equiv). The resulting solution was stirred for 5 h at 100° C. in an oil bath. The reaction mixture was concentrated under reduced pressure. The residue (100 mg) was purified by preparative RP-HPLC to afford 30 mg (19%) of the title compound as gray solid. LC/MS: m/z (ES+) 306 (M+H)⁺. ¹H-NMR (400 MHz, DMSO-d₆): δ ppm 9.81 (br s, 1H), 7.27 (dd, J=8.8, 5.6 Hz, 2H), 7.17-7.12 (m, 2H), 5.89 (d, J=7.6 Hz, 1H), 5.00-4.92 (m, 1H), 4.58 (s, 1H), 3.69-3.65 (m, 1H), 2.74 (d, J=6.4 Hz, 2H), 1.31 (d, J=6.8 Hz, 6H), 1.08 (d, J=6.4 Hz, 3H).

Example 52

Preparation of (R)-3-isopropyl-6-((2,2,2-trifluoro-1-phenylethyl)amino)pyrimidine-2,4(1H,3H)-dione (52)

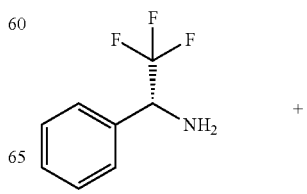

+

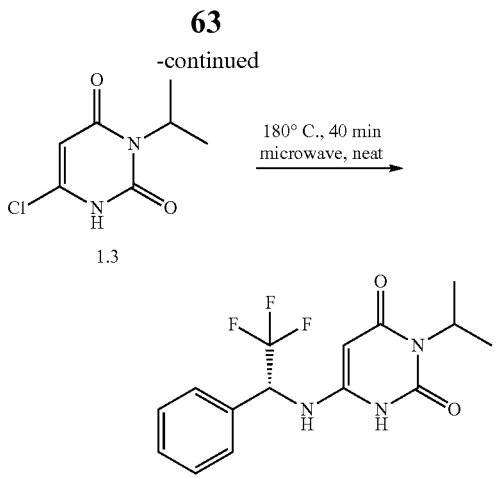

To a 0.2-0.5 mL microwave vial was added 1.3 (85 mg, 0.45 mmol) and (R)-2,2,2-trifluoro-1-phenylethan-1-amine (200 uL, excess). The reaction mixture sealed and heated at 180° C. in a microwave reactor for 40 minutes. The reaction mixture was cooled to ambient temperature and then NMP (1 mL) was added to completely dissolve the solid. Next, a 2:1 $H_2O/CH_3CN$ mixture (6 mL) was added which resulted in precipitation. The solid was isolated by filtration, washed with $H_2O$ and dried to give 50 mg (34%) of the title compound as a white solid. LC/MS: m/z (ES+) 328 (M+H)+. $^1$H-NMR (400 MHz, DMSO-$d_6$): δ ppm 9.79 (br s, 1H), 7.50-7.40 (m, 5H), 5.66-5.56 (m, 2H), 4.92-4.87 (m, 2H), 1.28-1.25 (m, 6H).

Example 53

Preparation of 3-((R)-1-(benzyloxy)propan-2-yl)-6-(((S)-1-phenylethyl)amino)pyrimidine-2,4(1H,3H)-dione

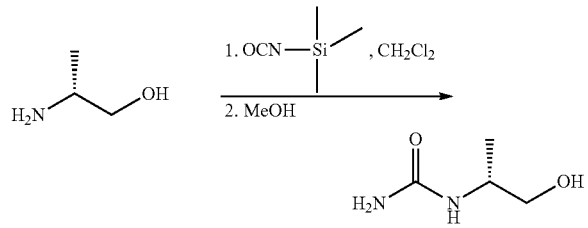

Compound 53.1. (R)-1-(1-hydroxypropan-2-yl)urea. To a stirred solution of (R)-(−)-2-amino-1-propanol (0.65 g, 8.68 mmol, 1 equiv.) in $CH_2Cl_2$ (10 mL) under $N_2$ at 0° C. was added dropwise trimethylsilyl isocyanate (1.00 g, 8.68 mmol, 1.0 equiv.). The reaction mixture was stirred overnight while slowly warming to room temperature. After cooling to 0° C., $CH_3OH$ (10 mL) was added dropwise. The resulting solution was stirred for 2 h at room temperature and was then concentrated under reduced pressure to provide the title compound (1.02 g, 99%) as a white solid.

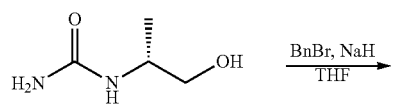

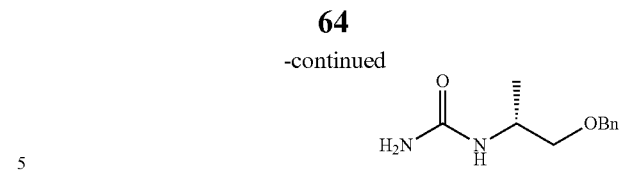

Compound 53.2. (R)-1-(1-(benzyloxy)propan-2-yl)urea. To a suspension of sodium hydride (0.52 g, 13.2 mmol, 1.5 equiv.) in THF (10 mL) at 0° C. was added 53.1 (1.02 g, 8.67 mmol, 1 equiv.). The reaction mixture was stirred for 20 minutes at 0° C. under $N_2$ before benzyl bromide (1.03 mL, 8.67 mmol, 1 equiv.) was added. The reaction mixture was stirred overnight while slowly warming to room temperature. The reaction mixture was quenched with $H_2O$ (3 mL) and was extracted into EtOAc (15 mL), dried with anhydrous $Na_2SO_4$, filtered, and concentrated. The resulting residue was purified by flash chromatography (10% $CH_3OH$ in $CH_2Cl_2$) to provide 510 mg (28%) of the title compound. LC/MS: m/z (ES+) 209 (M+H)+. $^1$H-NMR (400 MHz, CDCl$_3$): δ ppm 7.42-7.27 (m, 5H), 4.79 (d, J=6.7 Hz, 1H), 4.52 (d, J=2.7 Hz, 2H), 3.91 (s, 1H), 3.51 (dd, J=9.4, 3.9 Hz, 1H), 3.40 (dd, J=9.2, 5.3 Hz, 1H), 1.19 (d, J=7.0 Hz, 3H).

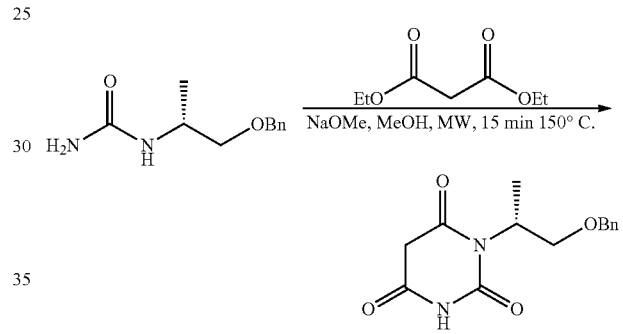

Compound 53.3. (R)-1-(1-(benzyloxy)propan-2-yl)pyrimidine-2,4,6(1H,3H,5H)-trione. To a microwave vial containing 53.2 (0.51 g, 2.42 mmol, 1 equiv.) in $CH_3OH$ (10 mL) was added diethyl malonate (2.55 g, 2.55 mmol, 1.05 equiv.) followed by sodium methoxide (25% wt. soln. in $CH_3OH$, 1.31 g, 6.06 mmol, 2.5 equiv.). The vial was capped and the reaction mixture was heated in a microwave reactor for 15 minutes at 150° C. After cooling to room temperature, the reaction mixture was quenched with $H_2O$ (2 mL) and the pH was adjusted to 3 with concentrated HCl. The reaction mixture was transferred to a round bottom flask and was concentrated under reduced pressure. The resulting residue was purified by flash chromatography (5% $CH_3OH$ in $CH_2Cl_2$) to provide 0.62 g (92%) of the title compound as a white solid. LC/MS: m/z (ES+) 277 (M+H)+. $^1$H-NMR (400 MHz, CDCl$_3$): δ ppm 7.99 (s, 1H), 7.38-7.22 (m, 5H), 5.16-5.11 (m, 1H), 4.52 (d, J=12.0 Hz, 1H), 4.45 (d, J=12.0 Hz, 1H), 4.02 (t, J=9.8 Hz, 1H), 3.56 (q, J=1.57 Hz, 2H), 1.37 (d, J=7.00 Hz, 3H).

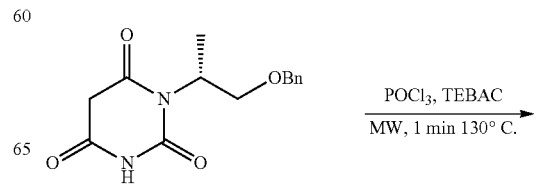

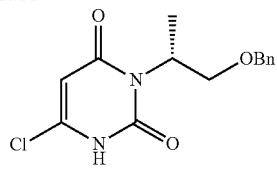

Compound 53.4. (R)-3-(1-(benzyloxy)propan-2-yl)-6-chloropyrimidine-2,4(1H,3H)-dione. To a microwave vial containing 53.3 (0.25 g, 0.91 mmol, 1 equiv.) was added triethylbenzylammonium chloride (0.28 g, 1.26 mmol, 1.4 equiv.) and POCl₃ (1 mL). The vial was capped and the reaction mixture was heated in a microwave reactor for 1 minute at 130° C. The reaction mixture was transferred to a round bottom flask and was concentrated under reduced pressure. The resulting residue was dissolved in CH₂Cl₂ (5 mL) and water (2 mL) was carefully added. The mixture was stirred for 10 minutes. The layers were separated and the organic layer was dried with Na₂SO₄, filtered and concentrated under reduced pressure. The resulting residue was purified by flash chromatography (silica gel, 5% CH₃OH in CH₂Cl₂) to provide 150 mg (55%) of the title compound. LC/MS: m/z (ES+) 295 (M+H)⁺. ¹H-NMR (400 MHz, CDCl₃): δ ppm 10.27 (s, 1H), 7.36-7.20 (m, 5H), 5.32-5.21 (m, 2H), 4.57 (d, J=12.0 Hz, 1H), 4.48 (d, J=12.0 Hz, 1H), 4.10 (dd, J=10.0, 9.2 Hz, 1H), 1.40 (d, J=7.0 Hz, 3H).

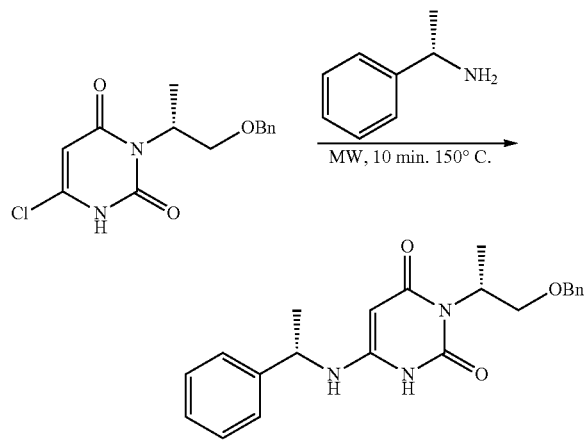

Compound 53. 3-((R)-1-(benzyloxy)propan-2-yl)-6-(((S)-1-phenylethyl)amino)pyrimidine-2,4(1H,3H)-dione. To a microwave vial containing (S)-α-methylbenzylamine (1.5 mL) was added 53.4 (0.12 g, 0.42 mmol). The vial was capped and the reaction mixture was heated in a microwave reactor for 10 minutes at 150° C. After cooling, the reaction mixture was filtered through a plug of silica gel (10% CH₃OH in CH₂Cl) and the filtrate was concentrated under reduced pressure. The resulting residue was dissolved in CH₂Cl₂ (10 mL) and was washed with 10% HCl (5 mL). The organic layer was dried with anhydrous Na₂SO₄, filtered and concentrated to provide 150 mg (94%) of the title compound. LC/MS: m/z (ES+) 380 (M+H)⁺. ¹H-NMR (400 MHz, CDCl₃): δ ppm 9.96 (br s 1H), 7.35-7.24 (m, 10H), 4.70 (br s, 1H), 4.53-4.41 (m, 4H), 4.03-3.99 (m, 1H), 3.65-3.61 (m, 1H), 1.49 (d, J=6.7 Hz, 3H), 1.37 (d, J=7.0 Hz, 3H).

Example 54

Preparation of 3-((R)-1-hydroxypropan-2-yl)-6-(((S)-1-phenylethyl)amino)pyrimidine-2,4(1H,3H)-dione (54)

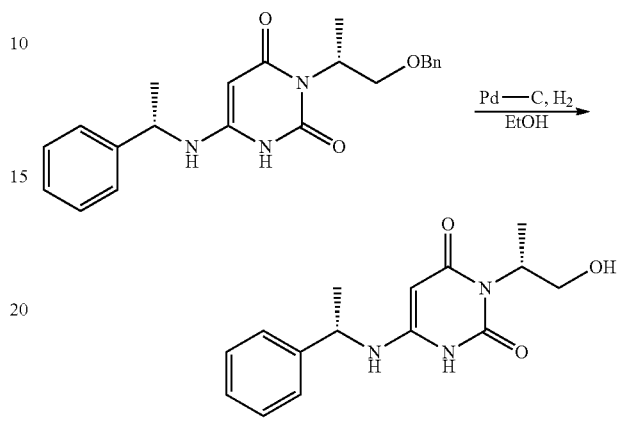

To a solution of 53 (0.10 g, 0.26 mmol, 1 equiv.) in EtOH (2 mL) was added palladium on carbon (10 wt. % loading (dry basis), matrix activated carbon, wet support, Degussa type, 0.025 g). The reaction flask was purged with nitrogen and was then fitted with a H₂(g) balloon. The reaction mixture was evacuated and then filled with H₂(g). This pump/purge process was repeated three times and the reaction mixture was stirred for 4 h at room temperature. After purging with nitrogen, the reaction mixture was filtered and the filtrate was concentrated under reduced pressure. The resulting residue was suspended in CH₃CN (2 mL) and the precipitate was isolated by filtration. The precipitate was dissolved in CH₂Cl₂: CH₃OH (1:1, 2 mL) and was filtered through a 0.2 μM PTFE 25 mm filter and was concentrated under reduced pressure to provide 27 mg (35%) of the title compound. LC/MS: m/z (ES+) 290 (M+H)⁺. ¹H-NMR (400 MHz, CDCl₃): δ ppm 9.67 (s, 1H), 7.35-7.24 (m, 5H), 5.64 (d, J=5.5 Hz, 1H), 5.08-5.04 (m, 1H), 4.66 (s, 1H), 4.42-4.35 (m, 1H), 4.24 (s, 1H), 4.04-3.91 (m, 1H), 3.78-3.68 (m, 1H), 1.50 (d, J=6.70 Hz, 3H), 1.35 (d, J=7.00 Hz, 3H).

Example 55

Preparation of (S)-3-isopropyl-6-((1-(3-(trifluoromethyl)phenyl)ethyl)amino)pyrimidine-2,4(1H,3H)-dione

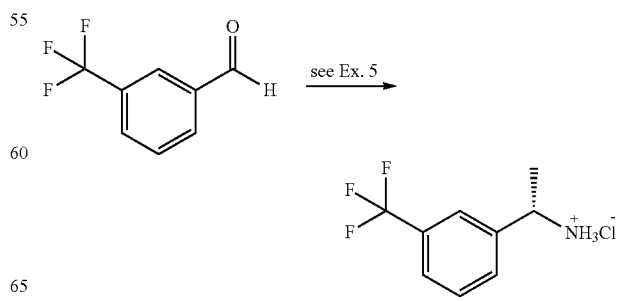

Compound 55.1. (S)-1-(3-(trifluoromethyl)phenyl)ethan-1-amine hydrochloride. The title compound was synthesized according to methods described for the preparation of 5.3, utilizing 3-(trifluoromethyl)benzaldehyde in place of 3,5-difluorobenzaldehyde.

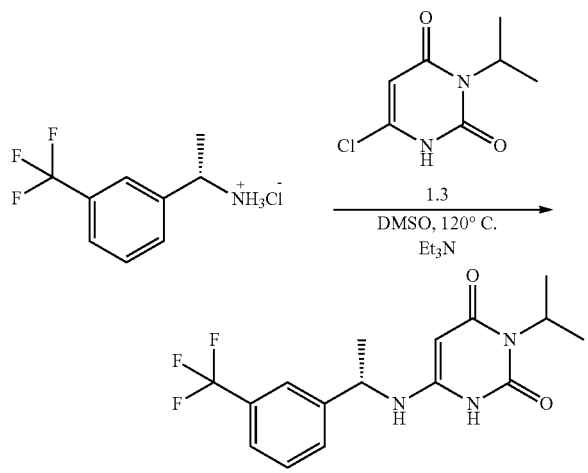

Compound 55. (S)-3-isopropyl-6-((1-(3-(trifluoromethyl)phenyl)ethyl)amino)pyrimidine-2,4(1H,3H)-dione. To a stirred solution of 55.1 (59.8 mg, 0.27 mmol, 1.00 equiv) in DMSO (1.5 mL) under an inert argon atmosphere was added Et₃N (0.2 mL) and 1.3 (50 mg, 0.27 mmol, 1.00 equiv). The resulting solution was stirred for 6 h at 120° C. in an oil bath. After cooling, the mixture was concentrated under reduced pressure and the resulting residue (75 mg) was purified by preparative RP-HPLC to give 6.5 mg (7%) of the title compound as a white solid. LC/MS: m/z (ES+) 342 (M+H)⁺. ¹H-NMR (300 MHz, DMSO-d₆): δ ppm 7.78 (s, 1H), 7.74-7.60 (m, 3H), 7.20 (br, 1H), 6.02 (br, 1H), 4.96 (dt, J=10.1, 5.1 Hz, 1H), 4.67-4.64 (m, 1H), 4.36 (s, 1H), 1.44 (d, J=6.8 Hz, 3H), 1.31-1.28 (m, 6H).

Example 56

Preparation of (S)-3-isopropyl-6-((1-(2-cyanophenyl)ethyl)amino)pyrimidine-2,4(1H,3H)-dione (56)

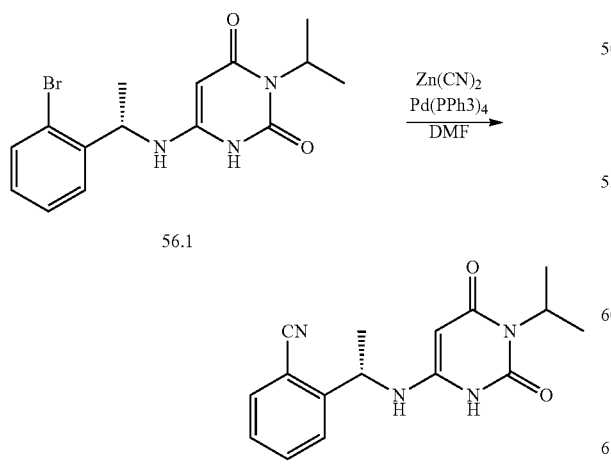

Intermediate 56.1 was prepared using procedures similar to those for the preparation of compound 35, utilizing 1.3 and (S)-1-(2-bromophenyl)ethan-1-amine hydrochloride (synthesized from the corresponding 2-bromobenzaldehyde using methods described for example 6.3). To a stirred solution of 56.1 (40 mg, 0.11 mmol, 1.00 equiv,) in DMF (2 mL) was added Zn(CN)₂ (20 mg, 0.17 mmol, 1.50 equiv) and tetrakis(triphenylphosphine) palladium (131 mg, 0.11 mmol, 0.20 equiv). CAUTION: CYANIDE CONTAINING REACTION. The resulting solution was stirred under an argon atmosphere at 100° C. in an oil bath for 2 h. Upon cooling, the reaction was quenched with a saturated aqueous FeSO₄ solution (5 mL). The resulting mixture was diluted with EtOAc (20 mL) and washed with a saturated aqueous FeSO₄ solution (2×20 mL). The organic layer was dried with anhydrous Na₂SO₄, filtered, and concentrated under reduced pressure. The crude product (5 mg) was purified by chiral preparative HPLC with the following conditions: Column, Phenomenex Lux-2 5u Cellulose-2, 30*150 mm; mobile phase, Hexanes and EtOH (hold 50.0% EtOH in 35 min); resulting in 2.1 mg (6%) of the title compound. LC/MS: m/z (ES+) 299 (M+H)⁺. ¹H-NMR (300 MHz, CD₃CN): δ ppm 8.59 (br s, 1H), 7.73 (d, J=8.4 Hz, 1H), 7.61-7.56 (m, 1H), 7.48-7.45 (m, 2H), 5.09-4.94 (m, 3H), 1.46 (d, J=6.6 Hz, 3H), 1.34-1.26 (m, 6H).

Example 57

Preparation of (S)-3-benzyl-6-((1-phenylethyl)amino)pyrimidine-2,4(1H,3H)-dione

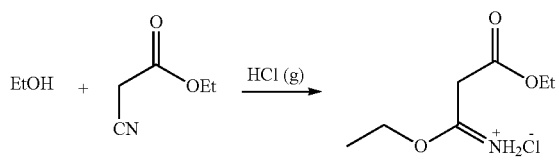

Compound 57.1. 3-ethoxy-3-oxo-1-(1-ethoxy)propan-1-iminium chloride. To a stirred solution of ethyl cyanoacetate (5.0 g, 44 mmol) in anhydrous Et₂O (5 mL) was added absolute EtOH (3 mL). The reaction mixture was cooled to 0° C. and HCl gas was bubbled in for 10 minutes. The reaction mixture was warmed to room temperature and was stirred for 16 h. The white precipitate that formed was filtered and washed with Et₂O (40 mL) and dried to give (6.99 g) the title compound as a white solid. LC/MS: m/z (ES+) 160 (M+H)⁺.

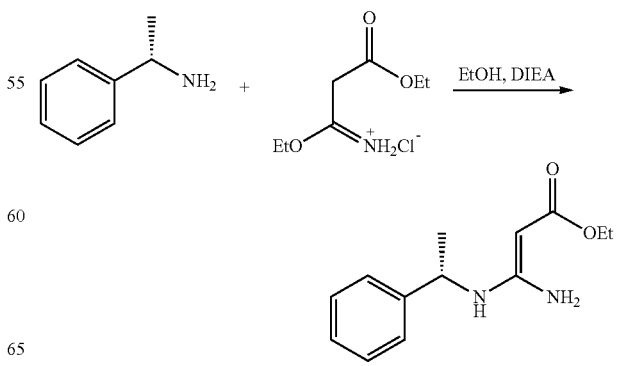

Compound 57.2. Ethyl (S,E/Z)-3-amino-3-((1-phenylethyl)amino)acrylate. To a stirred solution of 57.1 (585 mg, 3.0 mmol) in EtOH (15 mL) was added DIEA (0.8 mL), and (S)-α-methylbenzylamine (290 mg, 2.4 mmol). The reaction was stirred for 16 h and was concentrated. The crude was purified by flash column chromatography (silica gel, eluting with CH₃OH in CH₂Cl₂ (0 to 10%)) to yield 0.57 g (98%) of the title compound as a clear oil. NMR analysis revealed that the product was a mixture of E/Z isomers. LC/MS: m/z (ES+) 235 (M+H)⁺.

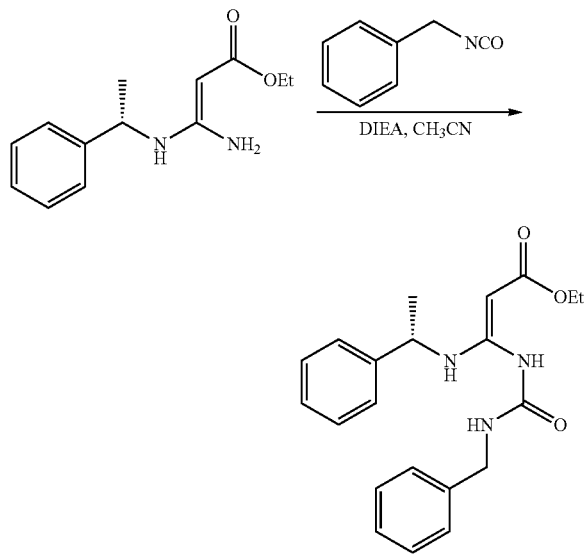

Compound 57.3. Ethyl (S,Z)-3-(3-benzylureido)-3-((1-phenylethyl)amino)acrylate. Two reactions were set up in parallel and later combined since both resulted in formation of product (by HPLC). In the first reaction, benzyl isocyanate (150 uL, 1.2 mmol) was added to a stirred solution of 57.2 (143 mg, 0.61 mmol) in CH₃CN (1 mL). After 10 min., DIEA (300 uL) was added. The reaction was stirred for an additional 10 min and was quenched with H₂O (12 mL). Solid precipitated and was removed by filtration. In the second reaction, benzyl isocyanate (150 uL, 1.2 mmol) was added to a stirred solution of 57.2 (143 mg, 0.61 mmol) and DIEA (300 uL) in CH₃CN (1 mL). After 10 min, the reaction mixture was quenched with H₂O (10 mL). The resulting mixture was diluted with EtOAc (40 mL) and the layers were separated. To the organic layer was added the filtrate from first reaction. The layers were separated and the organics were concentrated to give the title compound which was utilized without further purification.

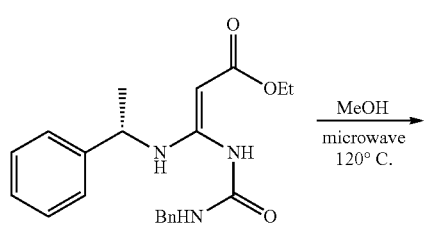

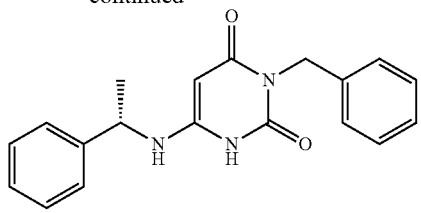

Compound 57. (S)-3-benzyl-6-((1-phenylethyl)amino)pyrimidine-2,4(1H,3H)-dione. Two reactions were conducted and later combined since both resulted in formation of product (by HPLC). The first reaction utilized ⅓ of crude 57.3 in CH₃OH (1 mL). It was heated in a microwave reactor at 120° C. for 10 min. The remaining ⅔ of crude 57.3 in CH₃OH (2 mL) was heated in a microwave reactor at 120° C. for 20 min. After cooling to ambient temperature, the reactions were combined and the CH₃OH was removed under reduced pressure. A 50/50 mixture of CH₃CN/H₂O with 0.1% TFA (5 mL) was added to the resulting residue. Solid precipitated and was filtered. The resulting brown solid was washed with EtOAc to give 7 mg of the title compound as a white solid. LC/MS: m/z (ES+) 322 (M+H)⁺. ¹H-NMR (400 MHz, DMSO-d₆): δ ppm 10.05 (br s, 1H), 7.35-7.31 (m, 4H), 7.26-7.16 (m, 6H), 6.61 (d, J=7.0 Hz, 1H), 4.79 (s, 2H), 4.52 (quin, J=6.8 Hz, 1H), 4.42 (d, J=2.3 Hz, 1H), 1.39 (d, J=6.7 Hz, 3H).

Example 58

Preparation of (S)-3-(2,6-difluorophenyl)-6-((1-phenylethyl)amino)pyrimidine-2,4(1H,3H)-dione (58)

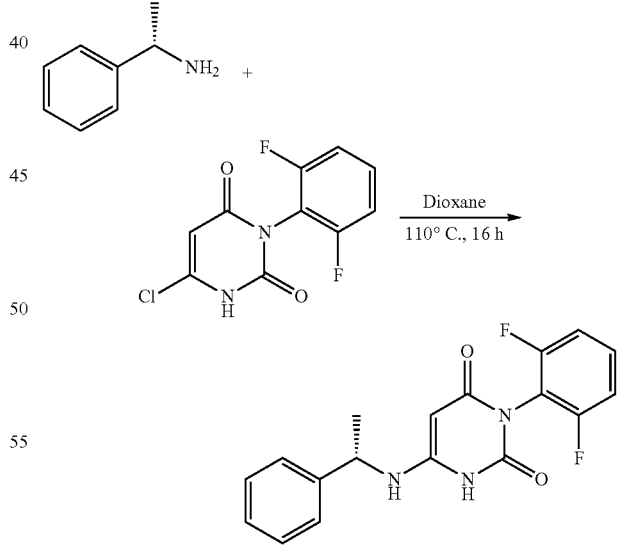

The title compound was synthesized according to a slightly modified procedure as described in Example 50. Here, 1,4-dioxane was utilized as a solvent and the reaction was heated at 110° C. for 16 h. The resulting mixture was cooled and concentrated under reduced pressure. The crude was purified by preparative RP-HPLC to give 19 mg of the title compound as a white solid. LC/MS: m/z (ES+) 344

(M+H)+. 1H-NMR (400 MHz, DMSO-d6): δ ppm 10.44 (br s, 1H), 7.52-7.42 (m, 2H), 7.39-7.36 (m, 3H), 7.34-7.16 (m, 3H), 6.91 (br s, 1H), 4.65-4.56 (m, 1H), 4.52 (s, 1H), 1.43 (d, J=6.7 Hz, 3H).

Example 59

Preparation of (S)-6-((1-(2,6-difluorophenyl)ethyl)amino)-3-isopropylpyrimidine-2,4(1H,3H)-dione

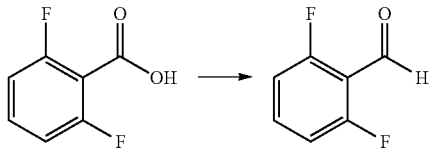 [SMILES: O=C(O)c1c(F)cccc1F ; O=Cc1c(F)cccc1F]

Compound 59.1. 2,6-difluorobenzaldehyde. The title compound was synthesized according to methods described for the preparation of 51.2. Here, commercially available 2,6-difluorobenzoic acid was utilized instead of 2-(4-fluorophenyl)acetic acid.

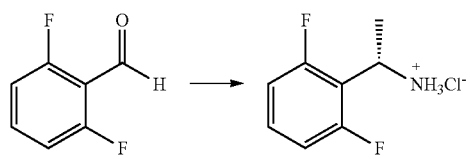

Compound 59.2. (S)-1-(2,6-difluorophenyl)ethan-1-amine hydrochloride. The title compound was synthesized according to methods described for the preparation of 5.3. Here, 59.1 was utilized instead of 3,5-difluorobenzaldehyde.

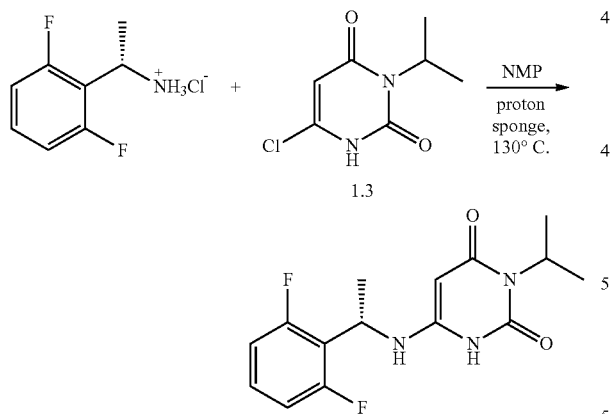

Compound 59. (S)-6-((1-(2,6-difluorophenyl)ethyl)amino)-3-isopropylpyrimidine-2,4(1H,3H)-dione. Reaction of 59.1 with 1.3 was conducted in a similar manner as the procedure described in Example 51. Here though, the reaction mixture was heated at 130° C. for 5 h. Analysis of the reaction mixture via chiral HPLC revealed non-trivial amounts of the enantiomer. Separation of the enantiomers was performed utilizing preparative chiral HPLC with an isocratic mixture of EtOH:Hexane (1:4) as eluent from a Phenomenex Lux-2 5μCellulose-2, 30*150 mm column (40 min run). LC/MS: m/z (ES+) 310 (M+H)+. 1H-NMR (400 MHz, DMSO-d6): δ ppm 9.80 (br s, 1H), 7.45-7.41 (m, 1H), 7.18-7.14 (m, 2H), 6.52 (d, J=8.0 Hz, 1H), 4.94-4.88 (m, 1H), 4.79 (quint, J=7.6 Hz, 1H), 4.41 (s, 1H), 1.56 (d, J=6.8 Hz, 3H), 1.30-1.26 (m, 6H).

Example 60

Preparation of (R)-6-((1-(2,6-difluorophenyl)ethyl)amino)-3-isopropylpyrimidine-2,4(1H,3H)-dione (60R)

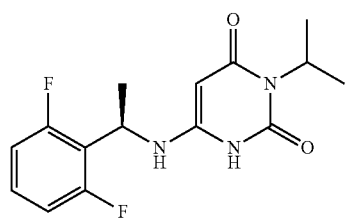 [SMILES: CC(C)n1c(=O)cc(N[C@H](C)c2c(F)cccc2F)[nH]c1=O]

The title compound was generated as a by-product of the chemistry conducted in Example 59. It was isolated via preparative chiral HPLC with an isocratic mixture of EtOH:Hexane (1:4) as eluent from a Phenomenex Lux-2 5μ Cellulose-2, 30*150 mm column (40 min run). LC/MS: m/z (ES+) 310 (M+H)+. 1H-NMR (400 MHz, DMSO-d6): δ ppm 9.98-9.61 (br, 1H), 7.45-7.41 (m, 1H), 7.18-7.14 (m, 2H), 6.52 (d, J=8.0 Hz, 1H), 4.94-4.88 (m, 1H), 4.79 (quint, J=7.6 Hz, 1H), 4.41 (s, 1H), 1.56 (d, J=6.8 Hz, 3H), 1.30-1.26 (m, 6H).

Example 61

Preparation of (S)-3-isopropyl-6-((1-pyridin-4-yl)propan-2-yl)amino)pyrimidine-2,4(1H,3H)-dione

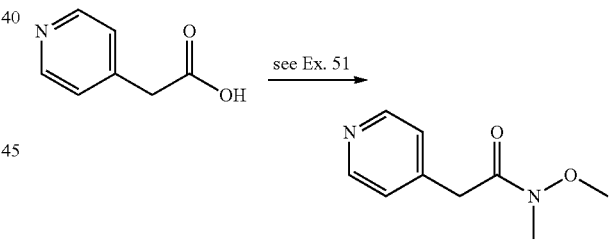

Compound 61.1. N-methoxy-N-methyl-2-(pyridin-4-yl)acetamide. The title compound was synthesized according to methods described for the preparation of 51.1. Here, commercially available 4-pyridineacetic acid was utilized instead of 2-(4-fluorophenyl)acetic acid.

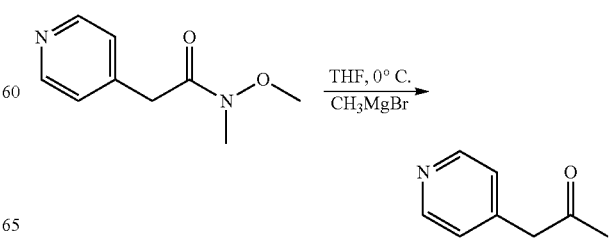

Compound 61.2. 1-(pyridin-4-yl)propan-2-one. To a 250-mL 3-necked round-bottom flask purged and maintained with an inert atmosphere of argon, was added THF (70 mL) and N-methoxy-N-methyl-2-(pyridin-4-yl)acetamide (7.0 g, 0.039 mol, 1.0 equiv). The mixture was cooled to 0° C. and CH$_3$MgBr (3M in THF, 65 mL, 5.0 equiv) was added dropwise. The resulting solution was warmed to ambient temperature and stirred for 16 h. The reaction mixture was cooled to 0° C. and quenched by the addition of saturated NH$_4$Cl (aq, 100 mL). The resulting solution was extracted with EtOAc (3×200 mL). The organic layers were combined, dried over anhydrous Na$_2$SO$_4$ and concentrated under reduced pressure. The crude was purified by flash chromatography (silica gel, CH$_2$Cl$_2$/CH$_3$OH (20:1)) to yield 2.7 g (51%) of the title compound as yellow oil. $^1$H-NMR (400 MHz, CDCl$_3$): δ ppm 8.58 (m, 2H), 7.17 (d, J=0.4 Hz, 2H), 3.75 (s, 2H), 2.24 (s, 3H).

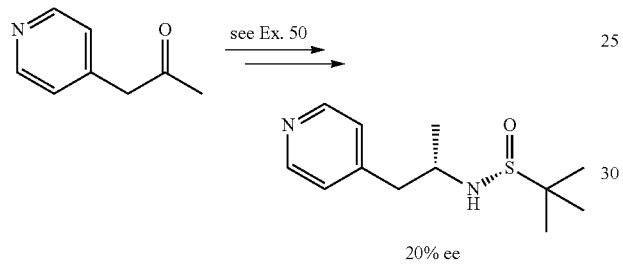

Compound 61.3. (R)-2-methyl-N—((S)-1-(pyridin-4-yl)propan-2-yl)propane-2-sulfinamide. The title compound was prepared according to procedures described in Example 50 utilizing 61.2 in place of 1-(3-methylphenyl)ethanone. Here, the reduction utilizing L-selectride resulted in isolation of the title compound (61.3) (20% enantiomeric excess).

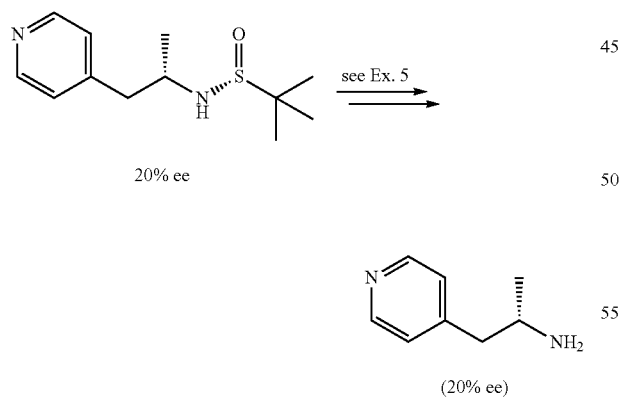

Compound 61.4. (S)-1-(pyridin-4-yl)propan-2-amine. The title compound was prepared utilizing a two-step procedure as described in Example 5. First, sulfonamide 61.3 was converted to the hydrochloride salt by treatment with HCl in 1,4-dioxane (see protocol for Compound 5.3). Subsequent free-basing of the hydrochloride salt (see protocol for Compound 5) resulted in the title compound (~20% ee).

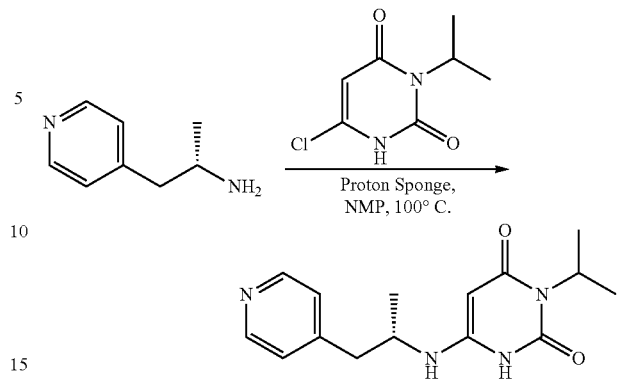

Compound 61. (S)-3-isopropyl-6-((1-(pyridin-4-yl)propan-2-yl)amino)pyrimidine-2,4(1H,3H)-dione. The title compound was prepared according to the protocol described for 51. Here, the reaction mixture was stirred for at 100° C. for 1 h. The reaction mixture was concentrated under reduced pressure and the residue (100 mg) was purified by Prep-HPLC to give 13.1 mg of the title compound as a mixture of enantiomers. The enantiomers were (13.1 mg) separated by chiral preparative HPLC with a Chiralpak IC, 2*25 cm, Sum column, utilizing a isocratic mixture of EtOH:Hexane (1:3) as eluent (20 min run). This resulted in 8.2 mg (8%) of the title compound as a light yellow solid. LC/MS: m/z (ES+) 289 (M+H)$^+$. $^1$H-NMR (300 MHz, CD$_3$OD): δ ppm 8.41 (d, J=5.7 Hz, 2H), 7.29 (d, J=6.0 Hz, 2H), 5.06-4.96 (m, 1H), 4.68 (s, 1H), 3.82-3.75 (m, 1H), 2.87-2.83 (m, 2H), 1.36 (d, J=7.2 Hz, 6H), 1.12 (d, J=7.2 Hz, 3H).

Example 62

Preparation of (S)-6-((1-(4-(benzyloxy)phenyl)ethyl)amino)-3-isopropylpyrimidine-2,4(1H,3H)-dione

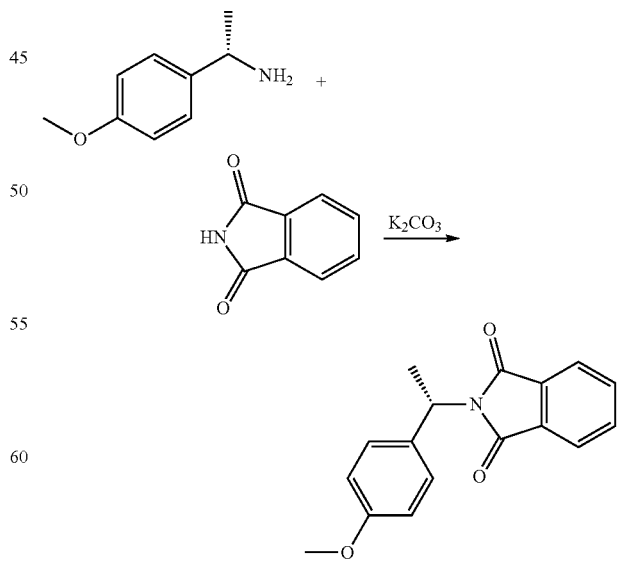

Compound 62.1. (5)-2-(1-(4-(methoxy)phenyl)ethyl)isoindoline-1,3-dione. To phthalimide (1.3 g, 0.0088 mol) in a 2-5 mL microwave vial was added (S)-1-(4-methoxyphenyl)ethan-1-amine (2.20 mL, 0.015 mol) and K$_2$CO$_3$ (1.2 g, 0.0087 mol). The reaction mixture capped and heated at 160° C. for 2 minutes. The resulting crude solid was suspended in n-BuOH and was filtered. The filtrate was put aside. The solid was washed with H$_2$O and the filtrate was discarded. The solid was washed with CH$_2$Cl$_2$ and the resulting filtrate was partitioned with H$_2$O. The organics (n-BuOH and CH$_2$Cl$_2$ layer) were combined and concentrated. The crude residue was purified by silica gel column chromatography using CH$_2$Cl$_2$ as eluent to yield 1.6 g (64%) of the title compound. LC/MS: m/z (ES+) 282 (M+H)$^+$.

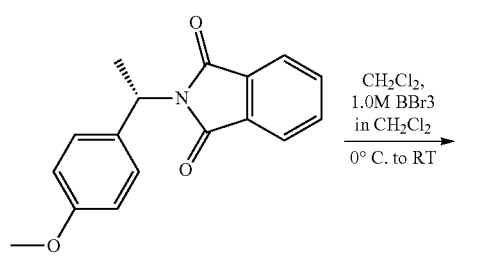

Compound 62.2. (S)-2-(1-(4-hydroxyphenyl)ethyl)isoindoline-1,3-dione. To a stirred solution of 62.1 (640 mg, 2.28 mmol) in CH$_2$Cl$_2$ (8 mL) at 0° C. was added BBr$_3$ (1.0 M in CH$_2$Cl$_2$, 3 mL, dropwise). The reaction was allowed to warm to room temperature over 30 minutes. Significant starting material remained so the reaction was chilled back to 0° C. Additional BBr$_3$ (2 mL, 1.0 M in CH$_2$Cl$_2$) was added and the reaction was allowed to warm to room temperature over 30 minutes. The reaction mixture was poured over 5% NaHCO$_3$ (aq) in ice. The layers were separated and the aqueous layer was further extracted with CH$_2$Cl$_2$. The combined organics were washed with brine, dried with anhydrous Na$_2$SO$_4$ and concentrated to give 500 mg (82%) of the title compound as a white solid. LC/MS: m/z (ES+) 268 (M+H)$^+$.

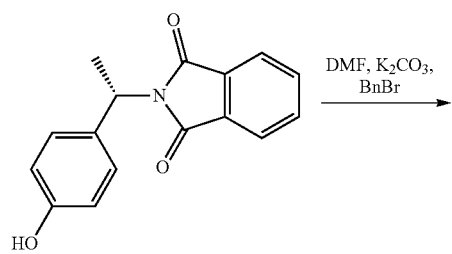

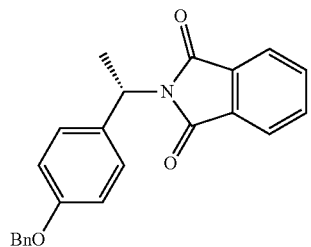

Compound 62.3. (S)-2-(1-(4-(benzyloxy)phenyl)ethyl)isoindoline-1,3-dione. To a stirred solution of 62.2 (500 mg, 1.87 mmol) in DMF (10 mL) was added K$_2$CO$_3$ (560 mg, 4.05 mmol, 2.17 equiv.) and benzyl bromide (0.30 mL, 420 mg, 2.45 mmol, 1.3 equiv.). The reaction was stirred at 120° C. for 5 h. The reaction was cooled and filtered. Water was added (20 mL) and EtOAc (60 mL) was utilized to extract product. The organic layer was washed successively with H$_2$O, 10% Na$_2$CO$_3$ (aq), H$_2$O, and brine (2×). The organics were dried over anhydrous MgSO$_4$ and concentrated. The crude residue was purified by flash chromatography (silica gel, eluting with CH$_2$Cl$_2$) to yield 480 mg (72%) of the title compound. LC/MS: m/z (ES+) 358 (M+H)$^+$.

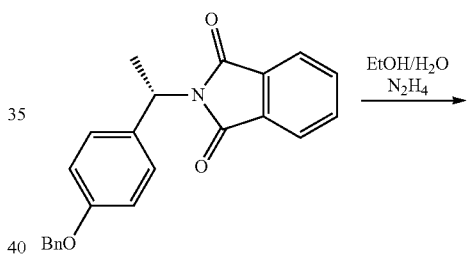

Compound 62.4. (S)-1-(4-(benzyloxy)phenyl)ethan-1-amine. To a stirred solution of 62.3 (480 mg, 1.34 mmol) in a 70/30 EtOH/H$_2$O mixture (20 mL) was added N$_2$H$_4$H$_2$O (1.5 mL). The reaction was stirred for 16 h and concentrated. The resulting material was partitioned between EtOAc and 5% Na$_2$CO$_3$ (aq). The layers were separated and the EtOAc layer was washed with brine and concentrated to give 280 mg (92%) of the title compound which was used without further purification. LC/MS: m/z (ES+) 228 (M+H)$^+$.

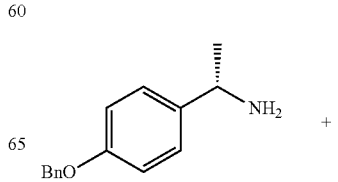

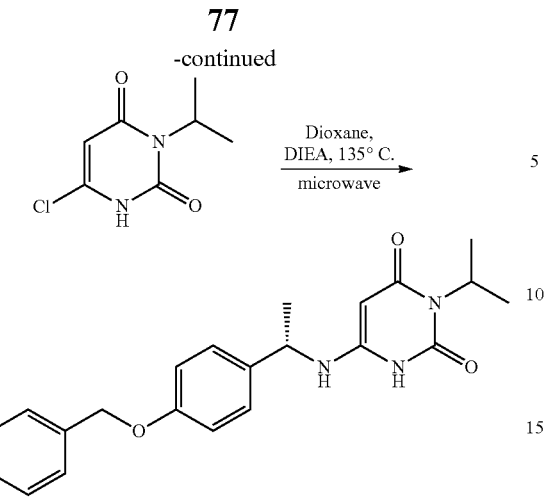

Compound 62. (S)-6-((1-(4-(benzyloxy)phenyl)ethyl) amino)-3-isopropylpyrimidine-2,4(1H,3H)-dione. To a 0.5-2.0 mL microwave vial was added 1,4-dioxane (1 mL), 62.4 (280 mg, 1.23 mmol), 1.3 (250 mg, 1.33 mmol) and DIEA (400 uL). The reaction mixture was capped, heated at 135° C. in a microwave reactor for 1.5 h, allowed to cool, and then concentrated. The crude reaction mixture was treated with 50/50 CH$_3$CN/H$_2$O (0.1% TFA) which led to precipitation. The solid was isolated by filtration and dried to give 45 mg (10%) of a white solid. LC/MS: m/z (ES+) 380 (M+H)$^+$. $^1$H-NMR (400 MHz, DMSO-d$_6$): δ ppm 9.73 (br, 1H), 7.43-7.29 (m, 5H), 7.23 (d, J=14.5 Hz, 2H), 6.97 (d, J=14.5 Hz, 2H), 6.42 (d, J=7.0 Hz, 1H), 5.06 (s, 2H), 4.93-4.85 (m, 1H), 4.42 (quin, J=6.8 Hz, 1H), 4.32 (d, J=1.6 Hz, 1H), 1.35 (d, J=6.7 Hz, 3H), (m, 1H) 1.27-1.23 (m, 6H).

Example 63

Preparation of (S)-6-((1-(4-hydroxyphenyl)ethyl) amino)-3-isopropylpyrimidine-2,4(1H,3H)-dione (63)

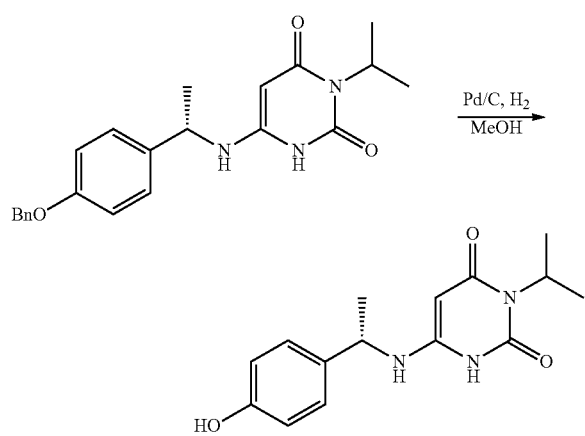

To a stirred solution of 62 (43 mg, 0.11 mmol) in CH$_3$OH (20 mL) was added palladium on carbon (50 mg, 10 wt. % loading (dry basis), matrix activated carbon, wet support, Degussa type). The vessel was purged with nitrogen followed by hydrogen. The reaction mixture was stirred under a H$_2$ atmosphere for 2 h. After purging the system with nitrogen, the mixture was filtered through celite and concentrated. The resulting solid was dissolved in 8 mL CH$_3$CN and then 20 mL H$_2$O (0.1% TFA) was added. The solution was frozen and lyophilized to give 29 mg (90%) of the title compound as a white solid. LC/MS: m/z (ES+) 290 (M+H)$^+$. $^1$H-NMR (400 MHz, DMSO-d$_6$): δ ppm 9.70 (br, 1H), 9.32 (s, 1H), 7.10 (d, J=8.6 Hz, 2H), 6.71 (d, J=8.6 Hz, 2H), 6.36 (d, J=7.0 Hz, 1H), 4.92-4.85 (m, 1H), 4.37-4.33 (m, 2H), 1.33 (d, J=6.7 Hz, 3H), 1.27-1.23 (in, 6H).

Example 64

Preparation of (R)-6-((2-(benzyloxy)-1-phenylethyl) amino)-3-isopropylpyrimidine-2,4(1H,3H)-dione

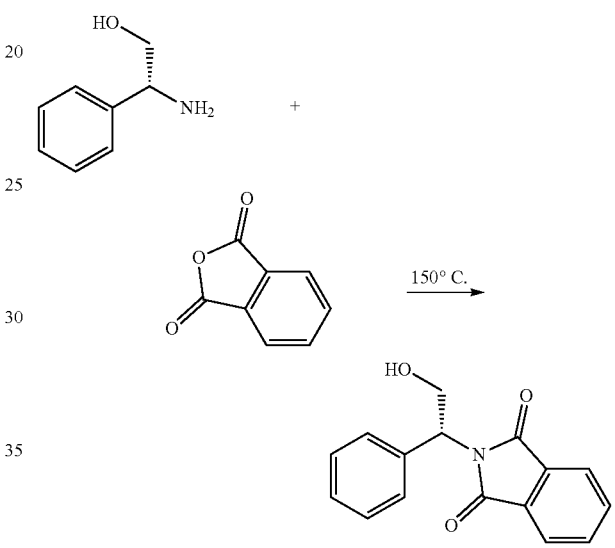

Compound 64.1. (R)-2-(2-hydroxy-1-phenylethyl)isoindoline-1,3-dione. To a 2.0-5.0 mL microwave vial was added (R)-2-amino-2-phenylethan-1-ol (1.53 g, 0.0112 mol) and phthalic anhydride (1.65 g, 0.0112 mol). The reaction mixture was capped and heated to 150° C. for 2 minutes in a microwave reactor. The mixture was cooled and diluted with CH$_3$CN (2 mL), recapped and heated in the microwave reactor a second time at 140° C. for 20 minutes. The volatiles were removed under reduced pressure and the resulting solid was suspended in EtOAc (50 mL). The organic layer was washed with 5% NaHCO$_3$ (aq), H$_2$O, and brine, dried with anhydrous MgSO$_4$ and concentrated. The crude residue was purified by flash chromatography (silica gel, eluting with CH$_3$OH in CH$_2$Cl$_2$ (0 to 5%) to yield 2.81 g (94%) of the title compound. LC/MS: m/z (ES+) 268 (M+H)$^+$.

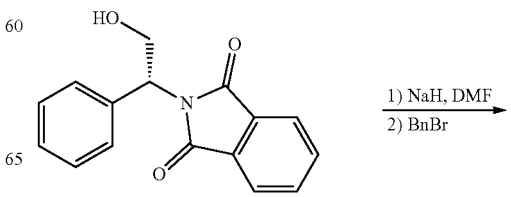

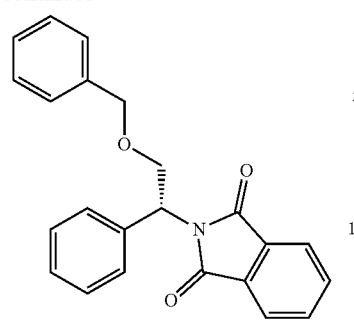

Compound 64.2. (R)-2-(2-(benzyloxy)-1-phenylethyl)isoindoline-1,3-dione. The title compound was made in a similar manner as the procedure described for 62.3. However, in this case NaH (60% dispersion in mineral oil, 1.2 equiv.) was used in place of $K_2CO_3$. Specifically, NaH was added at 0° C. and stirred at room temperature for 45 minutes. The reaction was cooled back to 0° C. and then benzyl bromide (1.2 equiv.) was added. A work-up procedure as described for 62.3 followed by flash chromatography (silica gel, eluting with $CH_2Cl_2$) yielded the title compound in 59% yield. LC/MS: m/z (ES+) 358 (M+H)$^+$. $^1$H-NMR (400 MHz, CDCl$_3$): δ ppm 7.84-7.79 (m, 2H), 7.72-7.67 (m, 2H), 7.52-7.48 (m, 2H), 7.37-7.20 (m, 8H), 5.62 (dd, J=10.2, 5.9 Hz, 1H), 4.63 (t, J=10.2 Hz, 1H), 4.58 (s, 2H), 4.06-4.01 (m, 1H).

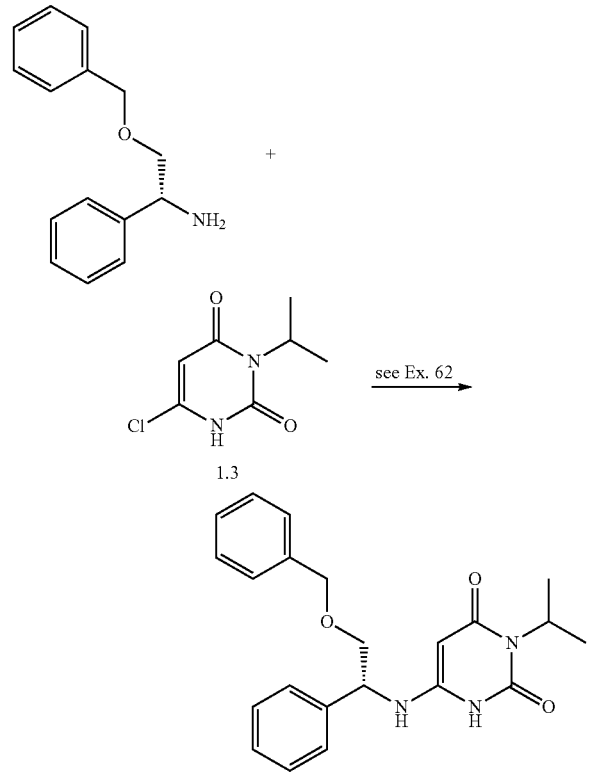

Compound 64. (R)-6-((2-(benzyloxy)-1-phenylethyl)amino)-3-isopropylpyrimidine-2,4(1H,3H)-dione. The title compound was prepared in a similar manner as the procedure described for 62. Here though, the reaction was heated at 140° C. for 1 h. After cooling, the crude reaction mixture was treated with 50/50 $CH_3CN/H_2O$ (0.1% TFA) which led to precipitation. LC/MS: m/z (ES+) 380 (M+H)$^+$. $^1$H-NMR (400 MHz, DMSO-d$_6$): δ ppm 10.01 (br, 1H), 7.36-7.26 (m, 10H), 6.62 (d, J=6.7 Hz, 1H), 4.93-4.83 (m, 1H), 4.67-4.62 (m, 1H), 4.50 (dd, J=12.0, 2.0 Hz, 2H), 4.30 (s, 1H), 3.68-3.64 (m, 1H), 3.60-3.55 (m, 1H) 1.27-1.23 (m, 6H).

Example 65

Preparation of (S)-3-(6-methylpyridin-2-yl)-6-((1-phenylethyl)amino)pyrimidine-2,4(1H,3H)-dione

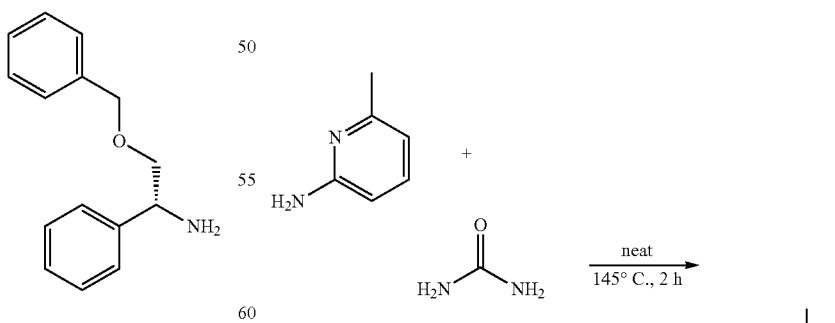

Compound 64.3. (R)-2-(benzyloxy)-1-phenylethan-1-amine. The title compound was prepared in a similar manner as the procedure described for 62.4. LC/MS: m/z (ES+) 228 (M+H)$^+$. $^1$H-NMR (400 MHz, CDCl$_3$): δ ppm 7.40-7.24 (m, 10H), 4.56 (d, J=2.0 Hz, 2H), 4.25 (dd, J=8.8, 3.7 Hz, 1H), 3.65-3.60 (m, 1H), 3.49-3.44 (m, 1H).

Compound 65.1. 1-(6-methylpyridin-2-yl)urea. To a 25-mL round-bottom flask purged and maintained with an inert atmosphere of argon, was added urea (1.48 g, 24.64 mmol, 1.00 equiv) and 6-methylpyridin-2-amine (3 g, 27.74 mmol, 1.00 equiv). The resulting mixture was stirred for 2 h at 145° C. After cooling, the crude product (4 g) was purified using CombiFlash: Column, C18 silica gel; utilizing a mobile phase of $CH_3CN:H_2O=0:100$ to $CH_3CN:H_2O=50:50$ over 40 min. This resulted in the isolation of 1.2 g (32%) of the title compound as a white solid. $^1$H-NMR (400 MHz, DMSO-$d_6$): δ ppm 9.07 (s, 1H), 7.56-7.52 (m, 1H), 7.18-7.14 (m, 1H), 6.80-6.75 (m, 1H), 2.36 (s, 3H).

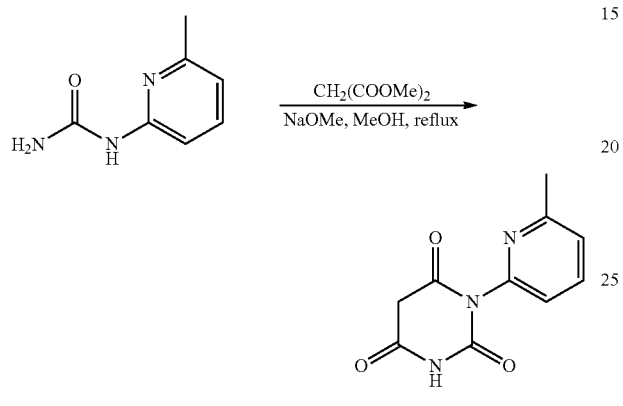

Compound 65.2. 1-(6-methylpyridin-2-yl)pyrimidine-2,4,6(1H,3H,5H)-trione. The title compound was prepared in a similar manner as the procedure described for 1.2. Here though, after stirring overnight at 65° C., the reaction mixture was concentrated under reduced pressure and the crude product was precipitated from $CH_3OH:Et_2O$ (1:50). The solid was collected by filtration and dissolved in $CH_3OH$ (50 mL). The pH value of the solution was adjusted to 7 with cation ion-exchange resin (Dowex 50WX8-100, 5 g). The solids were filtered and the filtrate was concentrated under reduced pressure resulting in 0.5 g (29%) of the title compound as a white solid. $^1$H-NMR (400 MHz, DMSO-$d_6$): δ ppm 9.27 (br s, 1H), 7.69 (t, J=7.6 Hz, 1H), 7.17 (d, J=7.6 Hz, 1H), 6.93 (d, J=7.6 Hz, 1H), 3.18 (s, 2H), 2.44 (s, 3H).

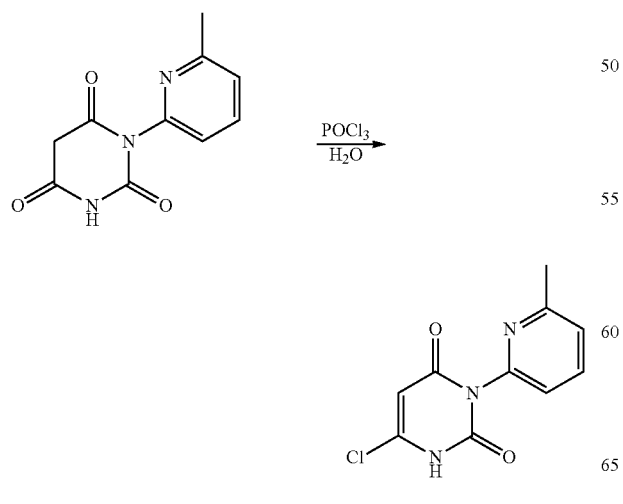

Compound 65.3. 6-chloro-3-(6-methylpyridin-2-yl)pyrimidine-2,4(1H,3H)-dione. To a stirred solution of 65.2 (500 mg, 2.28 mmol, 1.00 equiv) in $POCl_3$ (5 mL) at 0° C. was added a drop (~20 μL) of $H_2O$. The resulting solution was warmed to room temperature, stirred for 30 min., heated to 70° C. and stirred for 2 h. After cooling, the resulting mixture was concentrated under reduced pressure. The resulting residue was carefully dissolved in 10 mL of ice water. The pH was adjusted to 7 with anion ion-exchange resin (activated 201×4(711) strong base styrene anion exchange resin, 20 g) and the solids were filtered. The filtrate was concentrated under reduced pressure resulting in 0.2 g (37%) of the title compound as a yellow solid.

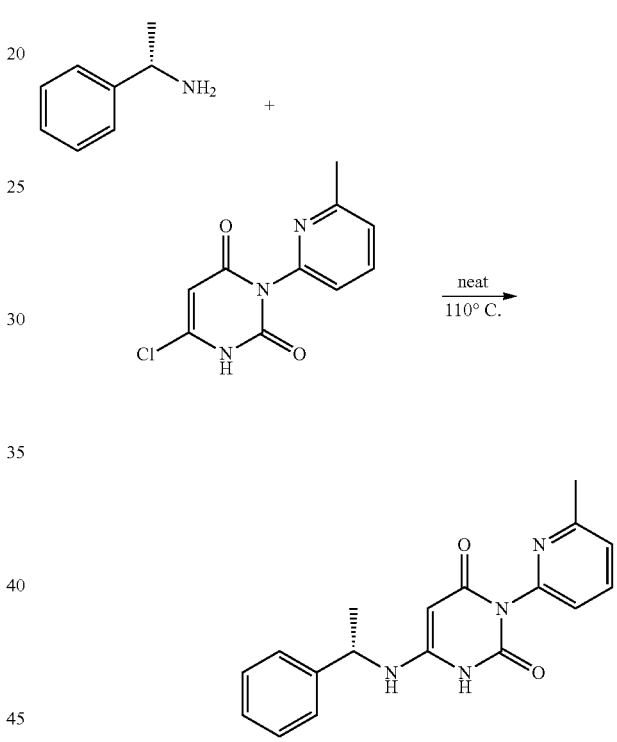

Compound 65. (S)-3-(6-methylpyridin-2-yl)-6-((1-phenylethyl)amino)pyrimidine-2,4(1H,3H)-dione. To a 10-mL round-bottom flask purged and maintained with an inert atmosphere of argon was added (S)-α-methylbenzylamine (0.5 mL) and 65.3 (200 mg, 0.84 mmol, 1.00 equiv). The resulting solution was stirred for 3 h at 110° C. After cooling, the resulting mixture was concentrated under vacuum. The residue (100 mg) was purified by preparative RP-HPLC with the following conditions: Column, XBridge Prep C18 OBD Column, 5 um, 19*150 mm; mobile phase, $H_2O$ with 0.05% $NH_4(HCO_3)$ and $CH_3CN$ (15% $CH_3CN$ to 80% in 8 min); This resulted in 28.8 mg (11%) of the title compound as a white solid. LC/MS: m/z (ES+) 323 (M+H)$^+$. $^1$H-NMR (400 MHz, DMSO-$d_6$): δ ppm 7.76 (t, J=7.6 Hz, 1H), 7.39-7.22 (m, 7H), 7.05 (d, J=7.6 Hz, 1H), 6.82 (br, 1H), 4.63-4.59 (m, 1H), 4.46 (s, 1H), 2.43 (s, 3H), 1.44 (d, J=6.4 Hz, 3H).

Example 66

Preparation of (S)-3-(2,2-difluoroethyl)-6-((1-phenylethyl)amino)pyrimidine-2,4(1H,3H)-dione

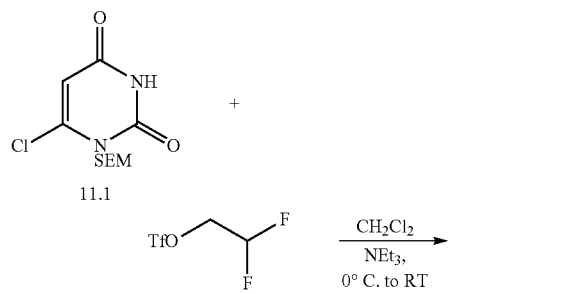

Compound 66.1. 6-chloro-3-(2,2-difluoroethyl)-1-((2-(trimethylsilyl)ethoxy)methyl) pyrimidine-2,4(1H,3H)-dione. To a stirred solution of 11.1 (130 mg, 0.47 mmol) and Et$_3$N (0.2 mL) in CH$_2$Cl$_2$ (2 mL) at 0° C. was added 2,2-difluoroethyl trifluoromethanesulfonate (0.10 mL). The reaction was warmed to room temperature and stirred for 30 minutes. The mixture was concentrated to give the title compound in a crude mixture.

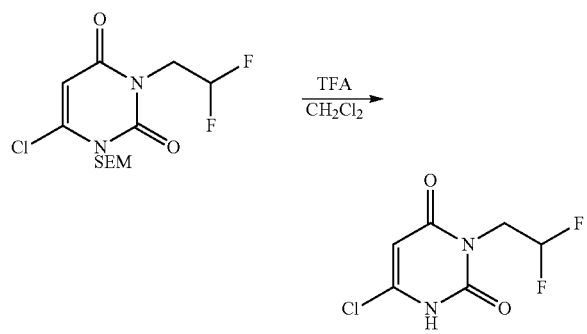

Compound 66.2. 6-chloro-3-(2,2-difluoroethyl)pyrimidine-2,4(1H,3H)-dione. Crude 65.1 was dissolved in CH$_2$Cl$_2$/TFA (1:1, 4 mL) and stirred for 3 h and concentrated. The resulting material was treated with 5% NaHCO$_3$ (aq) until the pH was 7. Ethyl acetate was added to the mixture and the layers were separated. The aqueous layer was concentrated. The resulting solid was suspended in CH$_3$CN (15 mL) and was remove by filtration. The filtrate was concentrated to give 52 mg of the title compound.

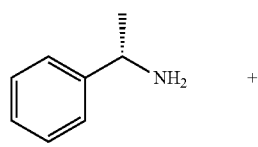

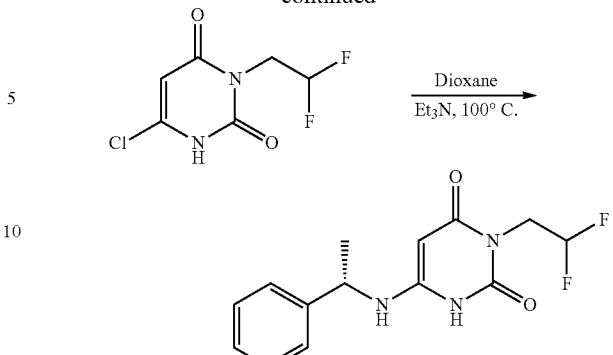

Compound 66. (S)-3-(2,2-difluoroethyl)-6-((1-phenylethy)amino)pyrimidine-2,4(1H,3H)-dione. To 66.2 (52 mg, 0.25 mmol) in 1,4-dioxane (1.5 mL) was added Et$_3$N (100 uL) and (S)-α-methylbenzylamine (188 mg, 1.55 mmol). The reaction mixture was heated in a microwave reactor at 100° C. for 32 minutes, cooled to room temperature, and then concentrated. The resulting residue was dissolved in a 2:3 CH$_3$CN/H$_2$O (10 mL) with 2 drops of TFA (~40 uL). The mixture was purified by preparative RP-HPLC to provide 8 mg (11%) of the title compound as a white solid. LC/MS: m/z (ES+) 296 (M+H)$^+$. $^1$H-NMR (400 MHz, DMSO-d6): δ ppm 10.20 (br s, 1H), 7.37-7.32 (m, 4H), 7.26-7.23 (m, 1H), 6.71 (d, J=7.0 Hz, 1H), 6.07 (tt, J =56.0, 4.5 Hz, 1H), 4.54 (quin, J=6.8 Hz, 1H), 4.43 (d, J=2.3 Hz, 1H), 4.02 (td, J=14.3, 4.7 Hz, 2H), 1.40 (d, J=6.7 Hz, 3H).

Example 67

Preparation of (S)-6-((1-(benzo[d][1,3]dioxol-5-yl)ethyl)amino)-3-(2,2,2-trifluoroethyl)pyrimidine-2,4(1H,3H)-dione

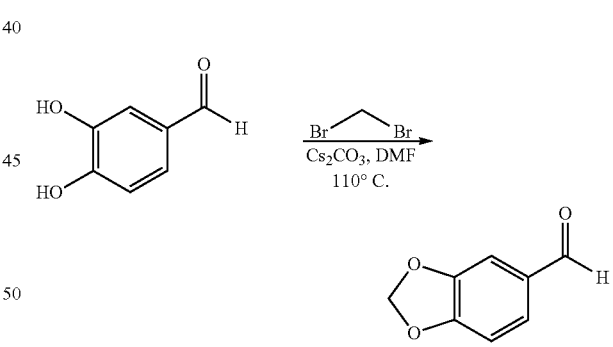

Compound 67.1. 2H-1,3-benzodioxole-5-carbaldehyde. To a stirred solution of 3,4-dihydroxybenzaldehyde (10 g, 72.40 mmol, 1.00 equiv) in DMF (150 mL) was added cesium carbonate (35.4 g, 108.31 mmol, 1.50 equiv) and dibromomethane (18.7 g, 107.57 mmol, 1.50 equiv). The resulting solution was stirred for 2 h at 110° C. The solution was cooled to room temperature and the solid was removed by filtration. The filtrate was diluted with H$_2$O (300 mL). The resulting solution was extracted with EtOAc (2×300 mL). The organic layers were combined, dried over sodium sulfate, and concentrated under reduced pressure. The crude residue was purified by silica gel column chromatography, eluted with EtOAc/petroleum ether (1:9) to afford 8 g (74%) of the title compound as a yellow solid. $^1$H-NMR (300 MHz, CDCl₃): δ ppm 9.81 (s, 1H), 7.41 (d, J=8.1 Hz, 1H), 7.34 (s, 1H), 6.93 (d, J=8.1 Hz, 1H), 6.08 (s, 2H).

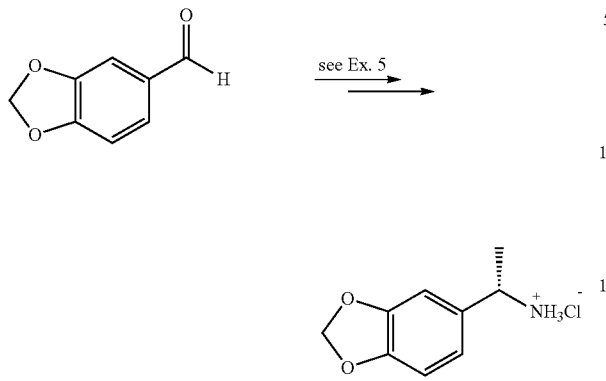

Compound 67.2. (S)-1-(benzo[d][1,3]dioxol-5-yl)ethan-1-amine hydrochloride. The title compound was synthesized according to methods described for the preparation of 5.3. Here, 67.1 was utilized instead of 3,5-difluorobenzaldehyde. LC/MS: m/z (ES+) 166 (M+H)⁺.

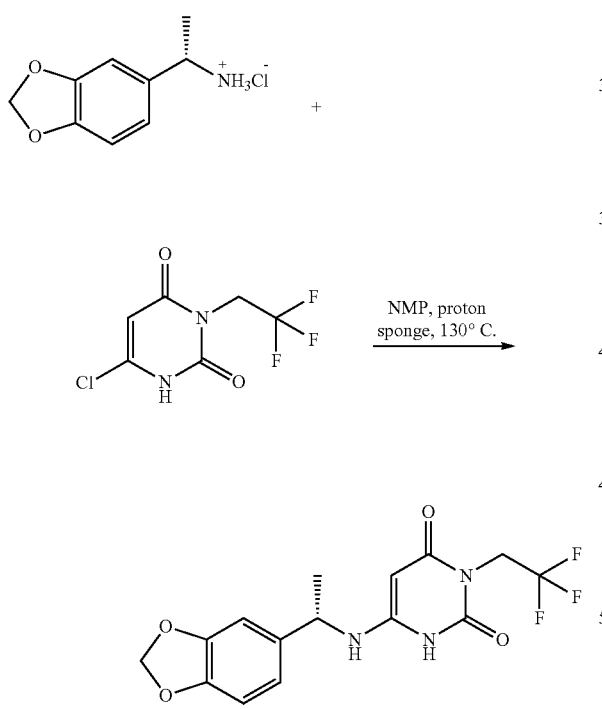

Compound 67. (S)-6-((1-(benzo[d][1,3]dioxol-5-yl)ethyl)amino)-3-(2,2,2-trifluoroethyl)pyrimidine-2,4(1H,3H)-dione. The title compound was synthesized according to methods described in Example 59. Here, 67.2 was utilized instead of (S)-1-(2,6-difluorophenyl)ethan-1-amine hydrochloride and 6-chloro-3-(2,2,2-trifluoroethyl)pyrimidine-2,4(1H,3H)-dione was utilized (synthesized according to methods described in Example 1) instead of 1.3. LC/MS: m/z (ES+) 358 (M+H)⁺. ¹H-NMR (300 MHz, DMSO-d₆): δ ppm 10.27 (br s, 1H), 6.94 (d, J=1.2 Hz, 1H), 6.89-6.82 (m, 3H), 6.72 (d, J=6.9 Hz, 1H), 5.99 (s, 2H), 4.48-4.40 (m, 4H), 1.38 (d, J=6.9 Hz, 3H).

Example 68

Preparation of (S)-3-isopropyl-6-((1-o-tolyl)ethyl)amino)pyrimidine-2,4(1H,3H)-dione (68)

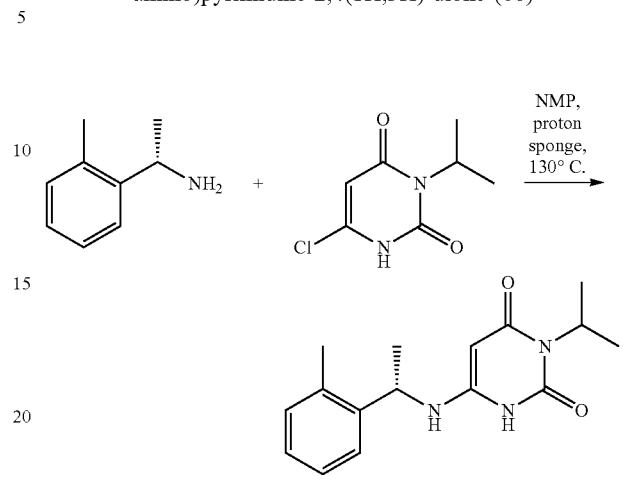

To a stirred solution of (1S)-1-(2-methylphenyl)ethan-1-amine (310 mg, 2.29 mmol, 1.50 equiv) in NMP (1 mL) was added proton sponge (491.4 mg, 2.30 mmol, 1.50 equiv) and 1.3 (288 mg, 1.53 mmol, 1.00 equiv). The resulting solution was stirred for 1 h at 130° C. in an oil bath, cooled to room temperature, and then diluted with DMSO (2 mL). The solids were filtered and the filtrate was purified by Flash-Prep-HPLC with the following conditions: Column: X Bridge C18, 19*150 mm, 5 um; Mobile Phase A: H₂O/0.05% TFA, Mobile Phase B: CH₃CN; Flow rate: 20 mL/min; Gradient: 30% B to 70% B in 10 min. This afforded 50 mg of crude product which was subsequently separated by chiral preparative HPLC with the following conditions: Column, Chiralpak IC, 2*25 cm, 5um; mobile phase, hexanes and ethanol (9:1, 15 min). This resulted in 35.6 mg (8%) of the title compound as a white solid. LC/MS: m/z (ES+) 288 (M+H)⁺. ¹H-NMR (300 MHz, DMSO-do): δ ppm 9.76 (br s, 1H), 7.28 (d, J=7.2 Hz, 1H) 7.24-7.14 (m, 3H), 6.48 (d, J=6.3 Hz, 1H), 4.95-4.86 (m, 1H), 4.60 (quin, J=6.9 Hz, 1H), 4.19 (s, 1H), 2.34 (s, 3H), 1.37 (d, J=6.6 Hz, 3H), 1.27 (d, J=6.9 Hz, 6H).

Example 69

Preparation of (S)-3-cyclobutyl-6-((1-phenylethyl)amino)pyrimidine-2,4(1H,3H)-dione

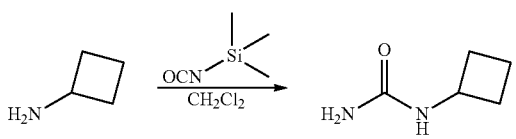

Compound 69.1. 1-cyclobutylurea. To a stirred solution of cyclobutanamine (40 g, 562.42 mmol, 1.00 equiv) in CH₂Cl₂ (400 mL) at 0° C. was added trimethylsilyl isocyanate (64.70 g, 561.60 mmol, 1.00 equiv.) portionwise. The resulting solution was stirred overnight at room temperature and was quenched by the addition of CH₃OH (80 mL). The resulting mixture was stirred for 1 h at room temperature and then concentrated under reduced pressure. The residue was washed with Et₂O (2×100 mL) and filtered, which afforded 53 g (83%) of the title compound as a white solid. ¹H-NMR (300 MHz, DMSO-d₆): δ ppm 6.17 (d, J=9.0 Hz, 1H), 5.33 (s, 2H), 3.99-3.91 (m, 1H), 2.16-2.07 (m, 2H), 1.81-1.68 (m, 2H), 1.61-1.45 (m, 2H).

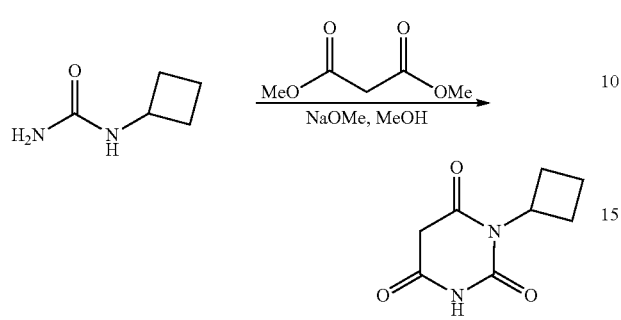

Compound 69.2. 1-cyclobutylpyrimidine-2,4,6(1H,3H, 5H)-trione. To a stirred solution of sodium methoxide (62.43 g, 1.156 mol, 2.40 equiv) in CH₃OH (500 mL) was added dimethyl malonate (76.42 g, 0.578 mol, 1.20 equiv) and 69.1 (55 g, 0.48 mol, 1.00 equiv). The resulting solution was heated to 65° C. and stirred overnight. The reaction was cooled and quenched by the addition of H₂O (100 mL). The pH of the solution was adjusted to 1 with concentrated HCl. The resulting mixture was concentrated under reduced pressure. The residue was purified by silica gel column chromatography with CH₂Cl₂/CH₃OH (20:1) as eluent to afford 60 g (68%) of the title compound as a white solid. ¹H-NMR (400 MHz, DMSO-d₆): δ ppm 11.20 (s, 1H), 4.95-4.86 (m, 1H), 3.56 (s, 2H), 2.72-2.62 (m, 2H), 2.16-2.09 (m, 2H), 1.78-1.60 (m, 2H).

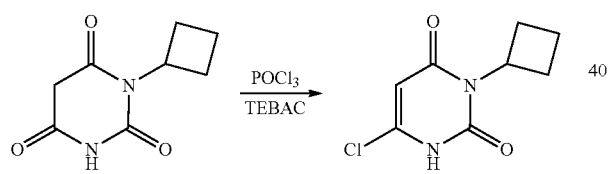

Compound 69.3. 6-chloro-3-cyclobutylpyrimidine-2,4 (1H,3H)-dione. To 69.2 (80 g, 0.44 mol, 1.00 equiv) and triethylbenzylammonium chloride (140.2 g, 0.615 mol, 1.40 equiv) was added (300 mL). The reaction was stirred for 1 h at 65° C. and was then concentrated under reduced pressure. The reaction was quenched by the careful addition of 1 L of water/ice and then the pH value of the solution was adjusted to 1 with 2N NaOH (aq). The solid was filtered, washed with CH₃OH (300 mL) and Et₂O (2×300 mL), and dried. This resulted in 78 g (89%) of the title compound as a light yellow solid. ¹H-NMR (300 MHz, DMSO-d₆): δ ppm 12.23 (s, 1H), 5.82 (s, 1H), 5.13-5.01 (m, 1H), 2.87-2.73 (m, 2H), 2.13-2.03 (m, 2H), 1.80-1.56 (m, 2H).

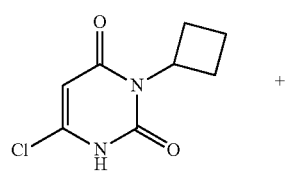 +

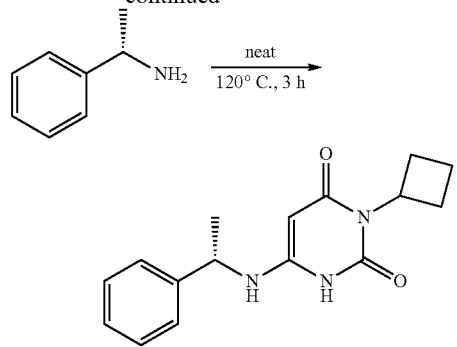

Compound 69. (S)-3-cyclobutyl-6-((1-phenylethyl) amino)pyrimidine-2,4(1H,3H)-dione. To a 500-mL round-bottom flask purged and maintained with an inert atmosphere of argon, was added 69.3 (78 g, 388.79 mmol, 1.00 equiv) and (S)-α-methylbenzylamine (150 mL, 2.00 equiv). The reaction mixture was stirred for 3 h at 120° C. The reaction mixture was cooled to room temperature, diluted with CH₃OH (1 L) and further cooled to 0° C. The resulting solid was filtered, washed with Et₂O (2×300 mL), and dried under vacuum to afford 57.25 g (52%) of the title compound as a white solid. LC/MS: m/z (ES+) 286 (M+H)⁺. ¹H-NMR (400 MHz, DMSO-d₆): δ ppm 9.94 (br s, 1H), 7.40-7.32 (m, 4H), 7.30-7.26 (m, 1H), 6.40 (br s, 1H), 5.19-5.10 (m, 1H), 4.56-4.49 (m, 1H), 4.35 (s, 1H), 2.91-2.81 (m, 2H), 2.02-1.95 (m, 2H), 1.76-1.58 (m, 2H), 1.42 (d, J=6.8 Hz, 3H).

Example 70

Preparation of (S)-3-isopropyl-6-((1-(2-(trifluoromethyl)phenyl)ethyl)amino)pyrimidine-2,4(1H,3H)-dione

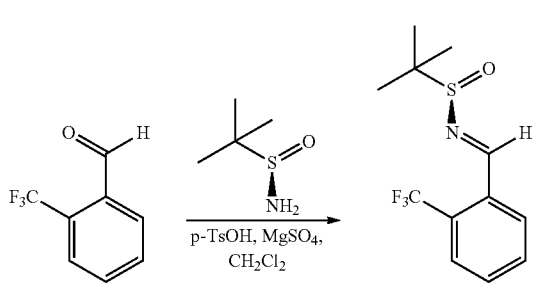

Compound 70.1. (R,E)-2-methyl-N-(2-(trifluoromethyl) benzylidene)propane-2-sulfinamide. To a 100-mL round-bottom flask purged and maintained with an inert atmosphere of argon, was added CH₂Cl₂ (50 mL), 2-(trifluoromethyl)benzaldehyde (2.01 g, 11.54 mmol, 1.00 equiv), (R)-(+)-2-methylpropane-2-sulfinamide (1.68 g, 13.86 mmol, 1.20 equiv), pyridinium p-toluenesulfonate (0.145 g, 0.05 equiv) and magnesium sulfate (6.93 g, 5.00 equiv). The resulting solution was stirred for 48 h at 40° C. The mixture was cooled to room temperature and the solid was filtered. The filtrate was concentrated under reduced pressure and the resulting residue was purified by flash column chromatography (silica gel, eluting with EtOAc/ petroleum ether (1:20)). This resulted in 0.96 g (30%) the title compound as a light yellow solid. LC/MS: m/z (ES+)

278 (M+H)+. 1H-NMR (300 MHz, DMSO-d6): δ ppm 8.82-8.80 (m, 1H), 8.24 (d, J=7.2 Hz, 1H), 7.95-7.80 (m, 3H), 1.22 (s, 9H).

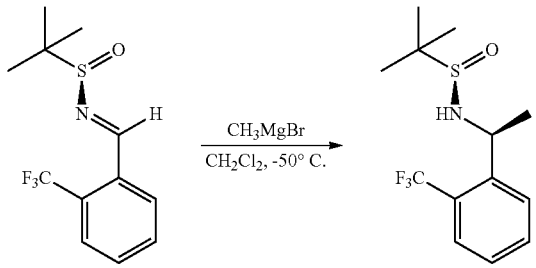 [SMILES: CC(C)(C)[S@@](=O)/N=C/c1ccccc1C(F)(F)F ; "CH3MgBr" ; C[C@H](N[S@](=O)C(C)(C)C)c1ccccc1C(F)(F)F]

Compound 70.2. (R)-2-methyl-N-((1S)-1-(2-(trifluoromethyl)phenyl)-ethyl)propane-2-sulfinamide. To a stirred solution of 70.1 (578 mg, 2.08 mmol, 1.00 equiv) in THF (20 mL) at −50° C. was added 3 M methylmagnesium bromide in Et2O (1.4 mL, 4.20 mmol, 2.0 equiv) dropwise. The resulting solution was stirred at −50° C. for 2.5 h and at room temperature for an additional 10 h. The reaction was quenched by the addition of a saturated aqueous NH4Cl solution (10 mL) and then concentrated under reduced pressure. The resulting residue was treated with H2O (50 mL) and extracted with CH2Cl2 (2×50 mL). The organic layers were combined, dried over Na2SO4, and concentrated under reduced pressure. This resulted in 700 mg (60% de) of the title compound as a yellow solid. LC/MS: m/z (ES+) 294 (M+H)+. 1H-NMR (300 MHz, DMSO-d6): δ ppm 7.77-7.74 (m, 1H), 7.67-7.60 (m, 2H), 7.43-7.38 (m, 1H), 5.53 (d, J=4.5 Hz, 1H), 4.70-4.60 (m, 1H), 1.42 (d, J=6.6 Hz, 3H), 1.02 (s, 9H).

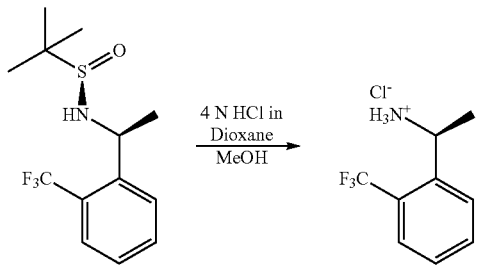 [SMILES: "MeOH" ; C[C@H](N[S@](=O)C(C)(C)C)c1ccccc1C(F)(F)F ; "4 N HCl inDioxane" ; C[C@H]([NH3+])c1ccccc1C(F)(F)F ; [Cl-]]

Compound 70.3. (S)-1-(2-(trifluoromethyl)phenyl)ethan-1-amine hydrochloride. To a stirred solution of 70.2 (700 mg, 2.39 mmol, 1.00 equiv) in CH3OH (4 mL) was added 4N HCl in 1,4-dioxane (2 mL) dropwise. The resulting solution was stirred for 1 h at room temperature and then concentrated under reduced pressure. Solid was precipitated by the addition of Et2O (5 mL). The solid was filtered and dried affording the title compound as a white solid (0.32 g, 60%).

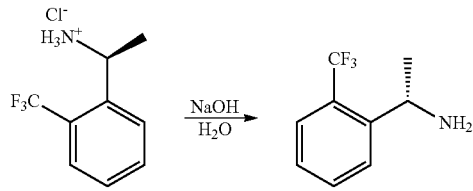

Compound 70.4. (S)-1-(2-(trifluoromethyl)phenyl)ethan-1-amine. To a 50-mL round-bottom flask was added 70.3 (320 mg, 1.43 mmol, 1.00 equiv) and sodium hydroxide (80 mg, 2.00 mmol, 1.40 equiv) in H2O (20 mL). The resulting solution was stirred for 1 h at room temperature and was then extracted with EtOAc (20 mL). The organic layer was combined and concentrated under reduced pressure. This afforded 190 mg (70%) of the title compound as light yellow oil.

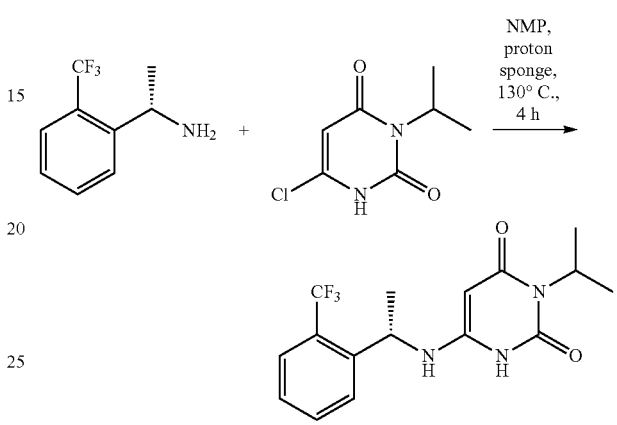

Compound 70. (S)-3-isopropyl-6-((1-(2-(trifluoromethyl)phenyl)ethyl)amino)pyrimidine-2,4(1H,3H)-dione. To a 10-mL round-bottom flask purged and maintained with an inert atmosphere of argon, was added NMP (2 mL), 70.4 (160 mg, 0.85 mmol, 1.00 equiv), 1.3 (160 mg, 0.85 mmol, 1.00 equiv), and proton sponge (273 mg, 1.28 mmol, 1.5 equiv.). The resulting solution was stirred for 4 h at 130° C. The crude product (200 mg) was purified by chiral preparative HPLC with the following conditions: Column, Phenomenex Lux-2 5u Cellulose-2, 30*150 mm; mobile phase, Hex-HPLC and ethanol-HPLC (hold 20% ethanol-HPLC in 14 min); Detector, uv 254/220 nm. 160 mg crude product was obtained. The obtained material (60 mg) was further purified using chiral preparative HPLC with following conditions: Column: Phenomenex Lux-2 5μ Cellulose-2 30*150 mm; Mobile Phase and Gradient: Hex:EtOH=80:20; Retention Time (Peak 2) (min): 11.106. This resulted in 30 mg of the title compound as a white solid. LC/MS: m/z (ES+) 342 (M+H)+. 1H-NMR (400 MHz, DMSO-d6): δ ppm 9.84 (br, 1H), 7.78-7.68 (m, 3H), 7.56-7.52 (m, 1H), 6.75 (br s, 1H), 4.93-4.86 (m, 1H), 4.68-4.63 (m, 1H), 4.13 (s, 1H), 1.46 (d, J=6.8 Hz, 3H), 1.25 (d, J=7.2 Hz, 6H).

Example 71

Preparation of (S)-3-(1-methylcyclopropyl)-6-((1-phenylethyl)amino)pyrimidine-2,4(1H,3H)-dione

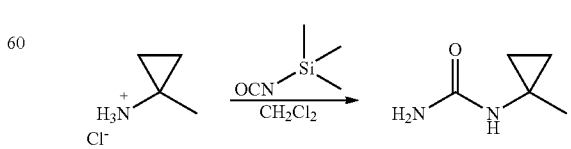

Compound 71.1. 1-(1-methylcyclopropyl)urea. To a stirred solution of 1-methylcyclopropan-1-amine hydrochloride salt (429 mg, 3.99 mmol, 1.00 equiv) and triethylamine (268 mg, 2.65 mmol, 1.00 equiv) in CH$_2$Cl$_2$ (6 mL) was added trimethylsilyl isocyanate (366 mg, 3.18 mmol, 1.20 equiv). The resulting mixture was stirred at room temperature overnight and was quenched by the dropwise addition of CH$_3$OH (2 mL) at 0° C. The resulting solution warmed to room temperature and stirred for an additional 1 h. The resulting mixture was concentrated under reduced pressure. The crude product was precipitated from CH$_3$OH:Et$_2$O (1:40) affording 300 mg (66%) of the title compound as a white solid.

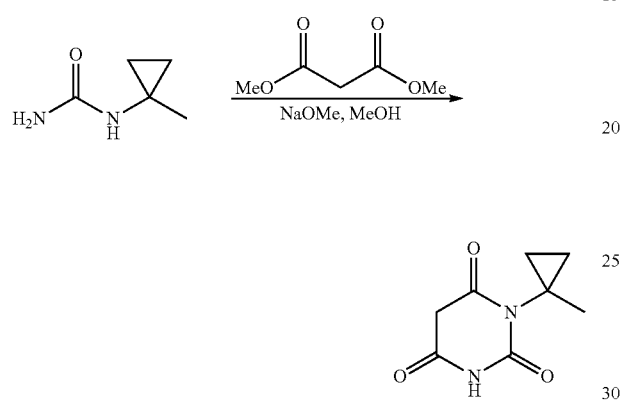

Compound 71.2. 1-(1-methylcyclopropyl)pyrimidine-2,4,6(1H,3H,5H)-trione. To a stirred solution of 71.1 (320 mg, 2.80 mmol, 1.0 equiv) in CH$_3$OH (2 mL) was added sodium methoxide (390 mg, 7.2 mmol, 2.5 equiv) and dimethyl malonate (380 mg, 2.88 mmol, 1.0 equiv). The resulting solution was stirred overnight at 65° C. After cooling, the reaction was quenched by the addition of H$_2$O (100 mL). The pH of the solution was adjusted to 2 with concentrated HCl and the resulting mixture was concentrated under reduced pressure. The crude residue was purified by silica gel column chromatography with EtOAc/petroleum ether (1:3) as eluent. This afforded 100 mg (20%) of the title compound as a white solid. $^1$H-NMR (300 MHz, CDCl3): δ ppm 8.04 (br, 1H), 3.61 (s, 2H), 1.41 (s, 3H), 1.00-, 0.86 (m, 4H).

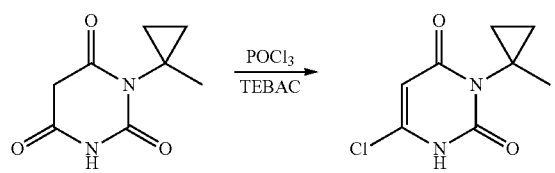

Compound 71.3. 6-chloro-3-(1-methylcyclopropyl)pyrimidine-2,4(1H,3H)-dione. To 71.2 (100 mg, 0.55 mmol, 1.00 equiv) and triethylbenzylammonium chloride (180 mg, 0.79 mmol, 1.00 equiv) was added POCl$_3$ (2 mL). The resulting solution was stirred for 3 h at 50° C. and then concentrated under reduced pressure. The residue was carefully quenched by the addition of 10 mL of water/ice and was extracted with EtOAc (2×30 mL). The organic layers were combined and concentrated under reduced pressure. The crude residue was purified by silica gel column chromatography with CH$_2$Cl$_2$/CH$_3$OH (10:1) as eluent to afford 40 mg (36%) of the title compound as a yellow solid.

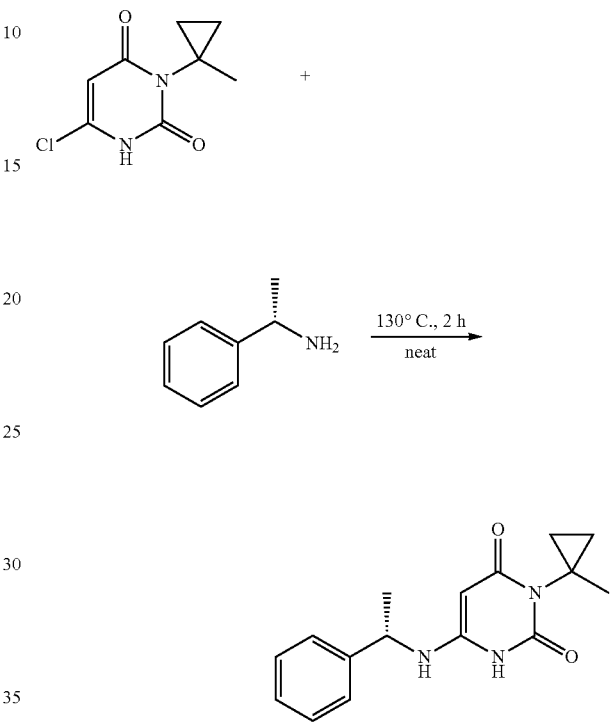

Compound 71. (S)-3-(1-methylcyclopropyl)-6-((1-phenylethyl)amino)pyrimidine-2,4(1H,3H)-dione. To 71.3 (40 mg, 0.20 mmol, 1.00 equiv) was added (S)-α-methylbenzylamine (0.5 mL). The reaction mixture was stirred for 2 h at 130° C. and then was concentrated under reduced pressure. The resulting residue was purified by preparative RP-HPLC with the following conditions: Column: X Bridge C18, 19*150 mm, 5 um; Mobile Phase A: H$_2$O/0.05% TFA, Mobile Phase B: CH$_3$CN; Flow rate: 20 mL/min; Gradient: 30% B to 70% B in 10 min. This afforded 15.1 mg (27%) of the title compound as a white solid. LC/MS: m/z (ES+) 286 (M+H)$^+$. $^1$H-NMR (300 MHz, CD$_3$CN): δ ppm 8.41 (br, 1H), 7.42-7.29 (m, 5H), 5.79 (br, 1H), 4.48-4.44 (m, 1H), 4.30 (s, 1H), 1.47 (d, J=6.9 Hz, 3H), 1.27 (s, 3H), 0.87-0.77 (m, 4H).

Example 72

Preparation of Additional Pyrimidine Dione Compounds

The compounds in Table 1B were prepared according to the examples as described above (exemplary methods provided as 'Reference. Ex. No.')

| Structure | Compound No. Reference Ex. No. | Observed Mass and/or ¹H NMR |
|---|---|---|
| 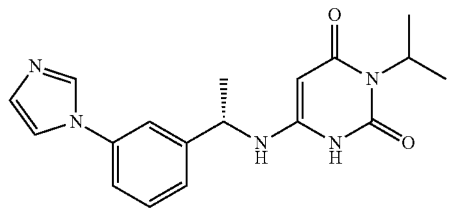 [SMILES: CC(C)n1c(=O)cc(N[C@@H](C)c2cccc(-n3ccnc3)c2)[nH]c1=O] | 72<br>17 | 340 (M + H)⁺<br>¹H-NMR (300 MHz, DMSO-d₆): δ ppm 9.89 (br s, 1H), 9.54 (br s, 1H), 8.22 (br s, 1H) 7.82 (br s, 1H), 7.75 (s, 1H) 7.66-7.54 (m, 2H), 7.48 (d, J = 7.5 Hz, 1H), 6.60-6.58 (m, 1H), 4.90-4.83 (m, 1H), 4.55-4.48 (m, 1H), 4.30 (s, 1H), 1.42 (d, J = 6.9 Hz, 3H), 1.27-1.21 (m, 6H). |
| 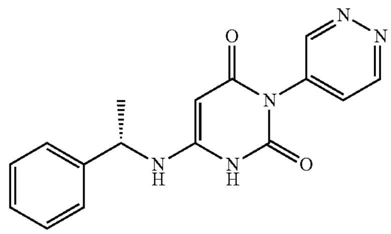 [SMILES: C[C@H](Nc1cc(=O)n(-c2ccnnc2)c(=O)[nH]1)c1ccccc1] | 73<br>15 | 310 (M + H)⁺<br>¹H-NMR (400 MHz, DMSO-d₆): δ ppm 9.20 (m, 1H), 9.04 (br s, 1H), 7.57 (m, 1H), 7.38-7.32 (m, 4H), 7.26-7.21 (m, 1H), 6.76 (m, 1H), 4.69-4.62 (m, 1H), 4.46 (s, 1H), 1.40 (d, J = 6.8 Hz, 3H). |
| 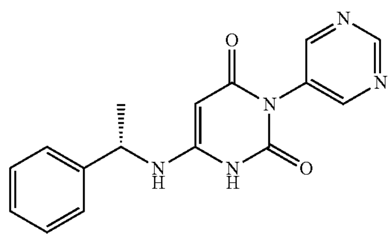 [SMILES: C[C@H](Nc1cc(=O)n(-c2cncnc2)c(=O)[nH]1)c1ccccc1] | 74<br>15 | 310 (M + H)⁺<br>¹H-NMR (400 MHz, DMSO-d₆): δ ppm 8.56 (m, 1H), 8.49 (m, 1H), 8.37 (m, 1H), 7.37-7.31 (m, 4H), 7.26-7.22 (m, 1H), 6.68 (m, 1H), 4.71-4.65 (m, 1H), 4.34 (s, 1H), 1.37 (d, J = 6.8 Hz, 3H). |
| 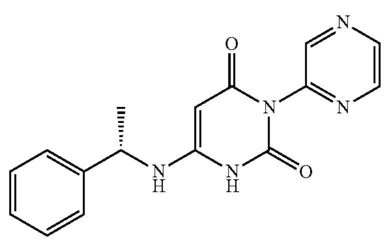 [SMILES: C[C@H](Nc1cc(=O)n(-c2cnccn2)c(=O)[nH]1)c1ccccc1] | 75<br>15 | 310 (M + H)⁺<br>¹H-NMR (400 MHz, DMSO-d₆): δ ppm 8.60 (m, 1H), 8.57 (m, 1H), 8.49 (br s, 1H), 7.39-7.32 (m, 4H), 7.26-7.22 (m, 1H), 6.68 (m, 1H), 4.69-4.64 (m, 1H), 4.41 (s, 1H), 1.39 (d, J = 6.8 Hz, 3H). |
| 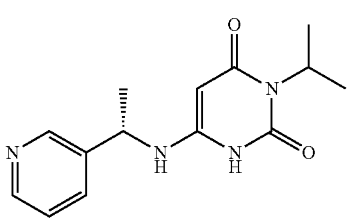 [SMILES: CC(C)n1c(=O)cc(N[C@@H](C)c2cccnc2)[nH]c1=O] | 76<br>5 and 58 | 275 (M + H)+<br>¹H-NMR (400 MHz, DMSO-d₆): δ ppm 9.70 (br, 1H), 8.60 (d, J = 2.0 Hz, 1H) 8.50 (dd, J = 4.8, 1.6 Hz, 1H), 7.76 (d, J = 8.0 Hz, 1H), 7.41 (dd, J = 7.6, 4.8 Hz, 1H), 6.67 (br s, 1H), 4.94-4.88 (m, 1H), 4.62-4.58 (m, 1H), 4.38 (s, 1H), 1.45 (d, J = 6.4 Hz, 3H), 1.30-1.28 (m, 6H). |
| 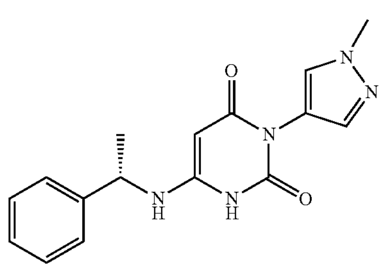 [SMILES: C[C@H](Nc1cc(=O)n(-c2cnn(C)c2)c(=O)[nH]1)c1ccccc1] | 77<br>15 | 312 (M + H)+<br>¹H-NMR (400 MHz, DMSO-d₆): δ ppm 10.69 (br s, 1H), 7.65 (s, 1H), 7.40-7.20 (m, 7H), 4.52 (quin, J = 6.8 Hz, 1H), 4.40 (s, 1H), 3.30 (br s, 3H), 1.39 (d, J = 7.0 Hz, 3H). |

-continued

| Structure | Compound No. Reference Ex. No. | Observed Mass and/or ¹H NMR |
|---|---|---|
| | 78 / 1 | 302 (M + H)+ ¹H-NMR (400 MHz, CDCl₃): δ ppm 10.58 (br s, 1H), 7.36-7.23 (m, 5H), 5.16 (m, 2H), 4.69 (s, 1H), 4.26 (m, 1H), 1.82-1.71 (m, 2H), 1.44-1.38 (m, 6H), 1.36-1.25 (m, 2H), 0.92 (t, J = 8.0 Hz, 3H). |
| | 79 / 11 | 316 (M + H)+ ¹H-NMR (400 MHz, CD₃CN): δ ppm 7.30-7.20 (m, 4H), 7.16-7.11 (m, 1H), 6.32 (m, 1H), 4.69-4.62 (m, 1H), 4.43 (quin, J = 6.7 Hz, 1H), 4.29 (s, 1H), 4.00 (t, J = 10.5 Hz, 1H), 3.67-3.59 (m, 1H), 3.44-3.40 (m, 1H), 3.14-3.08 (m, 1H), 2.48-2.38 (m, 1H), 1.56-1.45 (m, 3H), 1.38 (d, J = 6.8 Hz, 3H). |
| | 80 / 1 | 300 (M + H)+ ¹H NMR (400 MHz, DMSO-d₆) δ ppm 9.82 (br s, 1H), 7.41-7.19 (m, 5H), 6.50 (d, J = 6.7 Hz, 1H), 5.05-5.01 (m, 1H), 4.50-4.46 (m, 1H), 4.34 (s, 1H), 2.01-1.84 (m, 2H), 1.83-1.64 (m, 2H), 1.63-1.51 (m, 2H), 1.49-1.34 (m, 5H). |
| | 81 / 5 | 302 (M + H)+ ¹H-NMR (400 MHz, CD₃OD): δ ppm 7.39-7.35 (m, 2H), 7.30-7.28 (m, 3H), 5.06-5.00 (m, 1H), 4.53 (s, 1H), 4.12 (d, J = 7.2 Hz, 1H), 2.10-2.01 (m, 1H), 1.40-1.37 (m, 6H), 1.02 (d, J = 6.8 Hz, 3H), 0.93 (d, J = 6.8 Hz, 3H). |
| | 82 / 7 | 350 (M + H)+ ¹H-NMR (400 MHz, CD₃OD): δ ppm 7.43-7.33 (m, 4H), 7.30-7.26 (m, 1H), 4.82-4.75 (m, 1H), 4.54-4.49 (m, 2H), 2.74-2.65 (m, 2H), 2.15-2.05 (m, 2H), 1.93-1.79 (m, 2H), 1.61-1.57 (m, 2H), 1.51 (d, J = 6.8 Hz, 3H). |
| | 83 / 1 | 302 (M + H)+ ¹H-NMR (400 MHz, DMSO-d₆): δ ppm 9.73 (br s, 1H), 7.40-7.22 (m, 5H), 6.50 (d, J = 5.1 Hz, 1H), 4.57-4.44 (m, 2H), 4.34 (br s, 1H), 1.90 (ddd, J = 13.3, 9.8, 7.4 Hz, 2H), 1.61-1.50 (m, 2H), 1.38 (d, J = 6.7 Hz, 3H), 0.74-0.60 (m, 6H). |

-continued

| Structure | Compound No. Reference Ex. No. | Observed Mass and/or ¹H NMR |
|---|---|---|
| 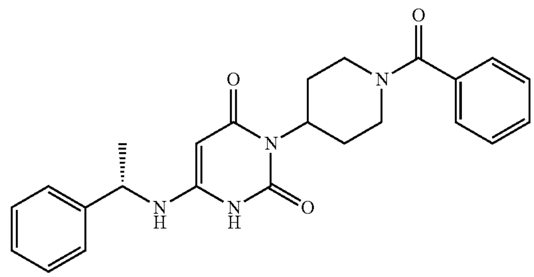 [SMILES: C[C@H](Nc1cc(=O)n(C2CCN(C(=O)c3ccccc3)CC2)c(=O)[nH]1)c1ccccc1] | 84<br>12 | 419 (M + H)+<br>¹H-NMR (400 MHz, DMSO-$d_6$): δ ppm 9.88 (br s, 1H), 7.45-7.41 (m, 3H), 7.37-7.29 (m, 6H), 7.27-7.22 (m, 1H), 6.54 (d, J = 6.7 Hz, 1H), 4.84-4.79 (m, 1H), 4.52-4.47 (m, 1H), 4.36 (d, J = 2.4 Hz, 1H), 3.57 (m, 2H), 3.05 (m, 2H), 2.38 (m, 2H), 1.50 (m, 2H), 1.38 (d, J = 6.7 Hz, 3H). |
| 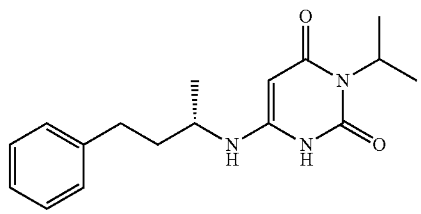 [SMILES: CC(C)n1c(=O)cc(N[C@@H](C)CCc2ccccc2)[nH]c1=O] | 85<br>1 | 302 (M + H)+<br>¹H-NMR (400 MHz, DMSO-$d_6$): δ ppm 9.73 (br s, 1H), 7.31-7.22 (m, 2H), 7.21-7.12 (m, 3H), 5.93 (d, J = 8.2 Hz, 1H), 5.00-4.87 (m, 1H) 4.44 (s, 1H), 4.30 (s, 1H), 3.37-3.31 (m, 1H), 2.65-2.53 (m, 2H), 1.70 (dtd, J = 9.0, 6.9, 6.9, 2.0 Hz, 1H), 1.29 (d, J = 7.0 Hz, 6H), 1.11 (d, J = 6.3 Hz, 3H). |
| 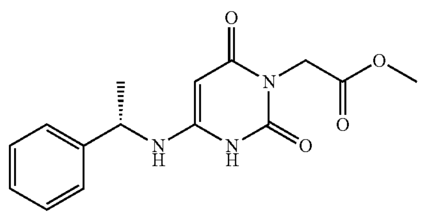 | 86<br>11 | 304 (M + H)+<br>¹H-NMR (400 MHz, $CD_3OD$ + $CDCl_3$): 7.22-7.15 (m, 2H), 7.13-7.07 (m, 3H), 6.28 (d, J = 6.1 Hz, 1H), 4.44 (s, 1H), 4.38 (s, 2H), 4.30-4.23 (m, 1H), 3.55 (s, 3H), 1.35 (d, J = 6.8 Hz, 3H). |
| 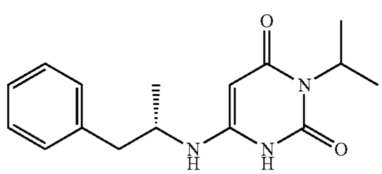 [SMILES: CC(C)n1c(=O)cc(N[C@@H](C)Cc2ccccc2)[nH]c1=O] | 90<br>1 | 288 (M + H)+<br>¹H-NMR (400 MHz, DMSO-$d_6$): δ ppm 9.77 (br s, 1H), 7.32-7.26 (m, 2H), 7.23-7.12 (m, 3H), 5.85 (d, J = 7.9 Hz, 1H), 4.97-4.87 (m, 1H), 4.55 (s, 1H), 3.77-3.65 (m, 1H), 2.76-2.68 (m, 2H), 1.27 (d, J = 7.0 Hz, 6H), 1.05 (d, J = 6.7 Hz, 3H). |
| 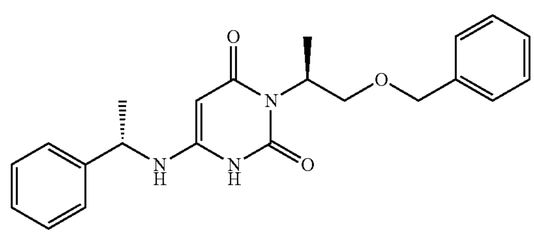 [SMILES: C[C@H](Nc1cc(=O)n([C@@H](C)COCc2ccccc2)c(=O)[nH]1)c1ccccc1] | 91<br>53 | 380 (M + H)+<br>¹H-NMR (400 MHz, $CDCl_3$): δ ppm 9.77 (br s, 1H), 7.33-7.23 (m, 10H), 5.23 (br s, 1H), 4.67 (br s, 1H), 4.57 (d, J = 12.0 Hz, 1H), 4.47 (d, J = 12.0 Hz, 1H), 4.44-4.37 (m, 1H), 4.09 (t, J = 9.2 Hz, 1H), 3.63 (dd, J = 9.8, 5.9 Hz, 1H), 1.48 (d, J = 6.7 Hz, 3H), 1.35 (d, J = 7.0 Hz, 3H). |
| 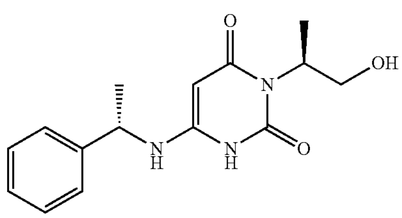 [SMILES: C[C@H](Nc1cc(=O)n([C@@H](C)CO)c(=O)[nH]1)c1ccccc1] | 92<br>54 | 290 (M + H)+<br>¹H-NMR (400 MHz, $CDCl_3$): δ ppm 9.68 (s, 1H), 7.41-7.22 (m, 5H), 5.62 (s, 1H), 5.08 (td, J = 7.3, 2.9 Hz, 1H), 4.67 (s, 1H), 4.48-4.35 (m, 1H), 3.98 (dd, J = 11.9, 7.6 Hz, 1H), 3.75 (dd, J = 11.7, 3.1 Hz, 1H), 1.52 (d, J = 7.0 Hz, 3H), 1.36 (d, J = 7.0 Hz, 3H). |

-continued

| Structure | Compound No. Reference Ex. No. | Observed Mass and/or ¹H NMR |
|---|---|---|
| 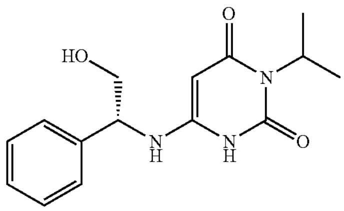 [SMILES: CC(C)n1c(=O)cc(N[C@@H](CO)c2ccccc2)[nH]c1=O] | 93<br>1 | 290 (M + H)+<br>¹H-NMR (400 MHz, DMSO-d₆): δ ppm 10.01 (d, J = 2.0 Hz, 1H), 7.37-7.23 (m, 5H), 6.61 (d, J = 6.3 Hz, 1H), 5.19 (t, J = 5.1 Hz, 1H), 4.93-4.83 (m, 1H), 4.40-4.33 (m, 1H), 4.24 (d, J = 2.4 Hz, 1H), 3.66 (dt, J = 11.1, 4.7 Hz, 1H), 3.52-3.44 (m, 1H), 1.25 (dd, J = 6.9, 2.2 Hz, 6H). |
| 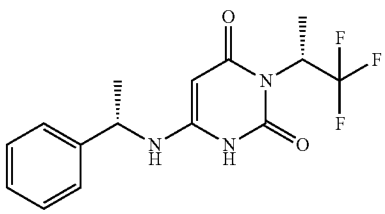 [SMILES: C[C@H](Nc1cc(=O)n([C@H](C)C(F)(F)F)c(=O)[nH]1)c1ccccc1] | 94<br>1 and 50 | 328 (M + H)+<br>¹H NMR (400 MHz, DMSO-d₆ @ 75° C.): δ ppm 9.91 (br s, 1H), 7.44-7.23 (m, 5H), 6.58 (br s, 1H), 5.52 (br s, 1H), 4.59-4.51 (m, 1H), 4.46 (br s, 1H), 1.52 (d, J = 7.0 Hz, 3H), 1.43 (d, J = 7.0 Hz, 3H). |
| 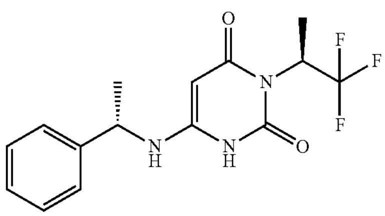 [SMILES: C[C@H](Nc1cc(=O)n([C@@H](C)C(F)(F)F)c(=O)[nH]1)c1ccccc1] | 95<br>1 and 50 | 328 (M + H)+<br>¹H NMR (400 MHz, DMSO-d₆ @ 75° C.): δ ppm 9.91 (br s, 1H), 7.44-7.23 (m, 5H), 6.58 (br s, 1H), 5.52 (br s, 1H), 4.59-4.51 (m, 1H), 4.46 (br s, 1H), 1.52 (d, J = 7.0 Hz, 3H), 1.43 (d, J = 7.0 Hz, 3H). |
| 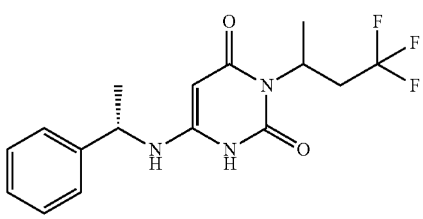 [SMILES: CC(CC(F)(F)F)n1c(=O)cc(N[C@@H](C)c2ccccc2)[nH]c1=O] | 99<br>1 | 342 (M + H)+<br>¹H-NMR (400 MHz, DMSO-d₆ @ 50° C.): δ ppm 9.79 (br s, 1H), 7.46-7.23 (m, 5H), 6.51 (d, J = 6.7 Hz, 1H), 5.13 (br s, 1H), 4.50 (quin, J = 6.9 Hz, 1H), 4.37 (s, 1H), 3.15-3.01 (m, 1H), 2.60-2.50 (m, 1H), 1.40 (d, J = 6.7 Hz, 3H), 1.31 (d, J = 7.0 Hz, 3H). |
| 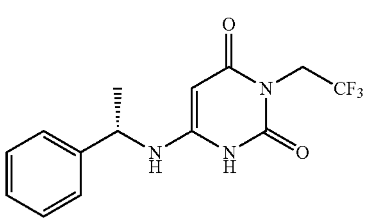 [SMILES: C[C@H](Nc1cc(=O)n(CC(F)(F)F)c(=O)[nH]1)c1ccccc1] | 100<br>1 and 50 | 314 (M + H)+<br>¹H-NMR (300 MHz, DMSO-d₆): δ ppm 10.32 (br s, 1H), 7.40-7.34 (m, 4H), 7.29-7.25 (m, 1H), 6.81 (d, J = 6.6 Hz, 1H), 4.60-4.54 (m, 1H), 4.49-4.40 (m, 3H), 1.42 (d, J = 6.6 Hz, 3H). |
| 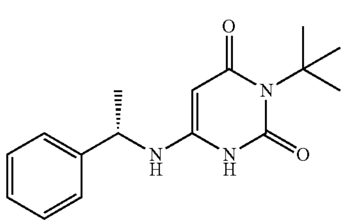 [SMILES: C[C@H](Nc1cc(=O)n(C(C)(C)C)c(=O)[nH]1)c1ccccc1] | 101<br>1 and 50 | 288 (M + H)+<br>¹H-NMR (400 MHz, DMSO-d₆): δ ppm 9.50 (br s, 1H), 7.56-7.44 (m, 4H), 7.38-7.24 (m, 1H), 6.41 (d, J = 6.4 Hz, 1H), 4.45 (q, J = 6.8 Hz, 1H), 4.25 (s, 1H), 1.54 (s, 9H), 1.38 (d, J = 6.8 Hz, 3H). |

-continued

| Structure | Compound No. Reference Ex. No. | Observed Mass and/or ¹H NMR |
|---|---|---|
| 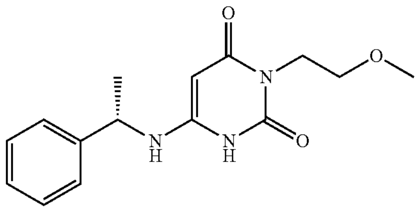 [SMILES: COCCn1c(=O)cc(N[C@@H](C)c2ccccc2)[nH]c1=O] | 102<br>57 | 290 (M + H)+<br>¹H-NMR (400 MHz, DMSO-d₆): δ ppm 10.31 (br s, 1H), 7.35-7.23 (m, 5H), 5.72 (d, J = 4.7 Hz, 1H), 4.67 (s, 1H), 4.40 (quin, J = 6.6 Hz, 1H), 4.05 (t, J = 5.7 Hz, 2H), 3.56 (t, J = 5.7 Hz, 2H), 3.27 (s, 3H), 1.46 (dd, J = 6.7, 1.6 Hz, 3H). |
| 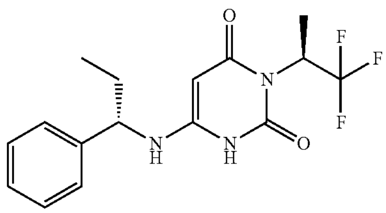 [SMILES: CC[C@H](Nc1cc(=O)n([C@@H](C)C(F)(F)F)c(=O)[nH]1)c1ccccc1] | 103<br>1 and 59 | 342 (M + H)+<br>¹H-NMR (400 MHz, DMSO-d₆, @ 75° C.): δ ppm 9.91 (br s, 1H), 7.37-7.24 (m, 5H), 6.59 (br s, 1H), 5.51 (br s, 1H), 4.45 (br s, 1H), 4.31 (q, J = 6.9 Hz, 1H), 1.83-1.67 (m, 2H), 1.52 (d, J = 7.4 Hz, 3H), 0.86 (t, J = 7.4 Hz, 3H). |
| 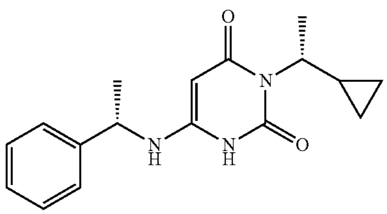 | 104<br>1 and 58 | 300 (M + H)+<br>¹H-NMR (400 MHz, DMSO-d₆): δ ppm 9.80 (br s, 1H), 7.37-7.31 (m, 4H), 7.27-7.22 (m, 1H), 6.52 (br, 1H), 4.48 (q, J = 6.7 Hz, 1H), 4.32 (br s, 1H), 3.93 (br, 1H), 1.62 (br, 1H), 1.38 (d, J = 6.7 Hz, 3H), 1.33 (d, J = 7.0 Hz, 3H), 0.48-0.41 (m, 1H), 0.27-0.21 (m, 1H), 0.14 (dq, J = 9.4, 4.8 Hz, 1H), 0.02 (m, 1H). |
| 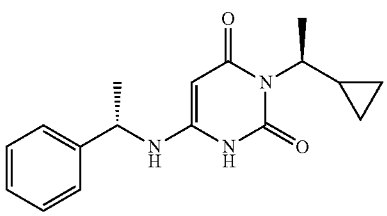 | 105<br>1 and 58 | 300 (M + H)+<br>¹H-NMR (400 MHz, DMSO-d₆): δ ppm 9.81 (br s, 1H), 7.37-7.30 (m, 4H), 7.26-7.22 (m, 1H), 6.53 (d, J = 5.9 Hz, 1H), 4.48 (q, J = 6.8 Hz, 1H), 4.32 (d, J = 1.6 Hz, 1H), 3.85 (m, 1H), 1.61 (m, 1H), 1.38 (d, J = 7.0 Hz, 3H), 1.32 (d, J = 6.7 Hz, 3H), 0.49-0.42 (m, 1H), 0.28-0.22 (m, 1H), 0.17-0.12 (m, 1H), 0.01- (−) 0.05, (m, 1H). |
| 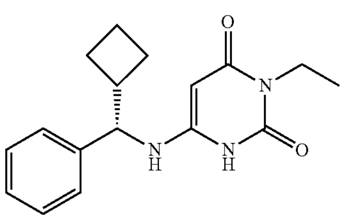 | 106<br>8 | 300 (M + H)+<br>¹H-NMR (300 MHz, DMSO-d₆): δ ppm 9.96 (br s, 1H), 7.36-7.24 (m, 5H), 6.48 (d, J = 6.3 Hz, 1H), 4.40 (s, 1H), 4.36-4.27 (m, 1H), 3.63 (q, J = 6.6 Hz, 2H), 2.67-2.50 (partially obscured m, 1H) 2.02-1.95 (m, 1H), 1.90-1.78 (m, 4H), 1.66-1.57 (m, 1H), 0.98 (t, J = 6.6 Hz, 3H). |
| 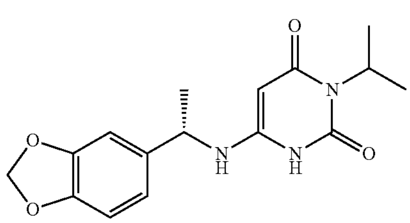 [SMILES: CC(C)n1c(=O)cc(N[C@@H](C)c2ccc3c(c2)OCO3)[nH]c1=O] | 107<br>67 and 59 | 318 (M + H)+<br>¹H-NMR (300 MHz, DMSO-d₆): δ ppm 9.76 (br s, 1H), 6.92 (d, J = 1.8 Hz, 1H), 6.87 (d, J = 7.8 Hz, 1H), 6.80 (dd, J = 6.0, 1.8 Hz, 1H), 6.44 (d, J = 7.2 Hz, 1H), 5.99 (s, 2H), 4.93-4.88 (m, 1H), 4.41-4.35 (m, 2H), 1.35 (d, J = |

-continued

| Structure | Compound No. Reference Ex. No. | Observed Mass and/or ¹H NMR |
|---|---|---|
| | | 6.6 Hz, 3H) 1.28 (d, J = 1.2 Hz, 3H) 1.26 (d, J = 1.2 Hz, 3H). |
| | 108<br>67 and 59 | 304 (M + H)+<br>¹H-NMR (300 MHz, DMSO-d₆): δ ppm 9.93 (br s, 1H), 6.92 (d, J = 1.5 Hz, 1H), 6.87 (d, J = 8.1 Hz, 1H), 6.82-6.79 (m, 1H), 6.48 (d, J = 7.2 Hz, 1H), 5.99 (s, 2H), 4.45-4.39 (m, 2H), 3.65 (q, J = 6.6 Hz, 2H), 1.36 (d, J = 6.9 Hz, 3H) 0.99 (t, J= 6.9 Hz, 3H). |
| | 109<br>1, 5 and 7 | 328 (M + H)+<br>¹H-NMR (300 MHz, DMSO-d₆): δ ppm 10.28 (br s, 1H), 7.39-7.24 (m, 5H), 6.81 (d, J = 6.6 Hz, 1H), 4.47-4.33 (m, 4H), 1.80-1.67 (m, 2H), 0.85 (t, J = 7.2 Hz, 3H). |
| | 110<br>1 and 50 | 286 (M + H)+<br>¹H-NMR (300 MHz, DMSO-d₆): δ ppm 10.01 (br s, 1H), 7.39-7.33 (m, 4H), 7.30-7.23 (m, 1H), 6.60 (d, J = 6.0 Hz, 1H), 4.52 (q, J = 6.6 Hz, 1H), 4.38 (s, 1H), 3.49 (d, J = 6.9 Hz, 2H), 1.40 (d, J = 6.9 Hz, 3H) 1.08-1.00 (m, 1H), 0.37-0.33 (m, 2H), 0.28-0.23 (m, 2H). |
| | 111<br>7 and 59 | 340 (M + H)+<br>¹H-NMR (400 MHz, DMSO-d₆): δ ppm 10.29 (br s, 1H), 7.37-7.33 (m, 4H), 7.30-7.25 (m, 1H), 6.98 (d, J = 5.6 Hz, 1H), 4.42 (q, J = 9.2 Hz, 2H), 4.35 (d, J= 1.6 Hz, 1H), 3.89-3.85 (m, 1H), 1.24-1.15 (m, 1H) 0.61-0.56 (m, 1H), 0.50-0.33 (m, 3H). |
| | 112<br>8 and 59 | 354 (M + H)+<br>¹H-NMR (400 MHz, DMSO-d₆): δ ppm 10.27 (br s, 1H), 7.45-7.25 (m, 5H), 6.73 (br s, 1H), 4.46-4.35 (m, 4H), 2.67-2.50 (partially obscured m, 1H), 2.04-2.01 (m, 1H), 1.90-1.79 (m, 4H), 1.68-1.62 (m, 1H). |
| | 113<br>15 | 306 (M + H)+<br>¹H-NMR (400 MHz, DMSO-d₆ @ 90° C.): δ ppm 9.86 (br s, 1H), 7.39-7.31 (m, 4H), 7.29-7.25 (m, 1H), 6.48 (d, J = 6.7 Hz, 1H), 5.00-4.91 (m, 1H), 4.78 (m, 1H), 4.56-4.50 (m, 1H), 4.45-4.38 (m, 2H), 3.76-3.70 (m, 2H), 1.42 (d, J = 7.4 Hz, 3H). |

-continued

| Structure | Compound No. Reference Ex. No. | Observed Mass and/or ¹H NMR |
|---|---|---|
| 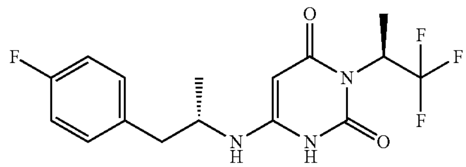 [SMILES: C[C@H](n1c(=O)cc(N[C@@H](C)Cc2ccc(F)cc2)[nH]c1=O)C(F)(F)F] | 114<br>1 and 51 | 360 (M + H)+<br>¹H-NMR (400 MHz, DMSO-d₆ @ 90° C.): δ ppm 9.86 (br s, 1H), 7.25 (dd, 8.4, 5.7 Hz, 2H), 7.10-7.04 (m, 2H), 5.94 (br s, 1H), 5.52 (br s, 1H), 4.62 (br s, 1H), 3.79-3.71 (m, 1H), 2.76 (d, J = 6.7 Hz, 2H), 1.55 (d, J = 7.0 Hz, 3H), 1.11 (d, J = 6.3 Hz, 3H). |
| 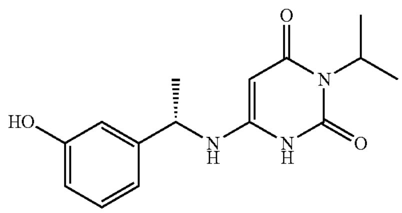 [SMILES: CC(C)n1c(=O)cc(N[C@@H](C)c2cccc(O)c2)[nH]c1=O] | 115<br>62 | 290<br>(M + H)+ |
| 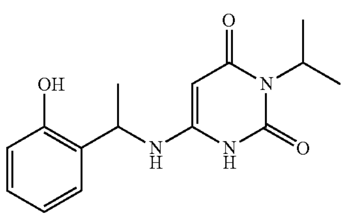 [SMILES: CC(Nc1cc(=O)n(C(C)C)c(=O)[nH]1)c1ccccc1O] | 116<br>62 | 290 (M + H)+<br>¹H-NMR (400 MHz, DMSO-d₆): δ ppm 9.83 (br s, 1H), 9.68 (br s, 1H), 7.14 (dd, J = 7.4, 1.6 Hz, 1H), 7.05 (td, J = 7.6, 1.6 Hz, 1H), 6.82-6.74 (m, 2H), 6.40 (d, J = 7.0 Hz, 1H), 4.92-4.85 (m, 1H), 4.60 (quin, J = 6.9 Hz, 1H), 4.30 (d, J = 2.4 Hz, 1H), 1.35 (d, J = 6.7 Hz, 3H), 1.27-1.22 (m, 6H). |
| 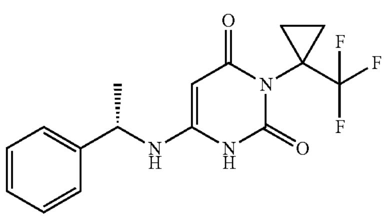 [SMILES: C[C@H](Nc1cc(=O)n(C2(C(F)(F)F)CC2)c(=O)[nH]1)c1ccccc1] | 117<br>1 and 59 | 340 (M + H)+<br>¹H-NMR (300 MHz, CDCl₃): δ ppm 10.40 (br s, 1H), 7.44-7.26 (m, 5H), 6.13 (br s, 1H), 4.80 (br s, 1H), 4.45 (m, 1H), 1.76-1.52 (m, 5H), 1.35-1.27 (m, 2H). |
| 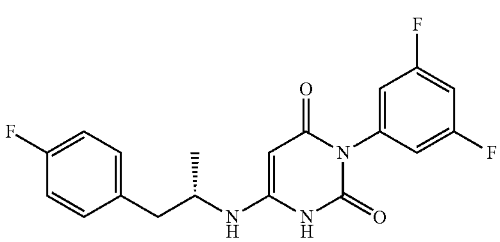 [SMILES: C[C@@H](Cc1ccc(F)cc1)Nc1cc(=O)n(-c2cc(F)cc(F)c2)c(=O)[nH]1] | 118<br>1 and 51 | 376 (M + H)+<br>¹H-NMR (400 MHz, DMSO-d₆): δ ppm 10.27 (br s, 1H), 7.29-7.22 (m, 3H), 7.15-7.10 (m, 2H), 7.01 (dd, J = 8.2, 2.3 Hz, 2H), 6.12 (br s, 1H), 4.72 (d, J = 2.0 Hz, 1H), 3.79-3.71 (m, 1H), 2.76 (d, J = 6.7 Hz, 2H), 1.09 (d, J = 6.7 Hz, 3H). |
| 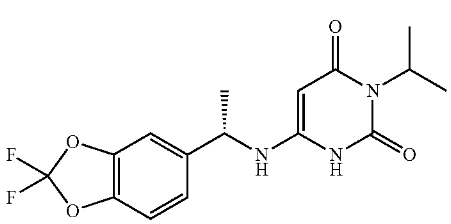 [SMILES: CC(C)n1c(=O)cc(N[C@@H](C)c2ccc3c(c2)OC(F)(F)O3)[nH]c1=O] | 119<br>5 and 59 | 354 (M + H)+<br>¹H-NMR (400 MHz, DMSO-d₆): δ ppm 9.84 (br s, 1H), 7.43 (d, J = 1.2 Hz, 1H), 7.38 (d, J = 8.0 Hz, 1H), 7.21 (dd, J = 8.4, 1.2 Hz, 1H), 6.54 (d, J = 6.8 Hz, 1H), 4.90 (q, J = 6.8 Hz, 1H), 4.55-4.52 (m, 1H), 4.34 (d, J = 2.0 Hz, 1H), 1.39 (d, J = 6.8 Hz, 3H) 1.31-1.26 (m, 6H). |

| Structure | Compound No. Reference Ex. No. | Observed Mass and/or ¹H NMR |
|---|---|---|
| (structure 120) | 120<br>5 and 59 | 308 (M + H)+<br>¹H-NMR (300 MHz, DMSO-d$_6$): δ ppm 9.87 (m, 1H), 7.48-7.28 (m, 4H), 6.66 (d, J = 6.6 Hz, 1H), 4.93-4.84 (m, 1H), 4.70 (quin, J = 6.6 Hz, 1H), 4.08 (s, 1H), 1.41 (d, J = 6.6 Hz, 3H), 1.28-1.24 (m, 6H). |
| (structure 121) | 121<br>5 | 304 (M + H)+<br>¹H-NMR (400 MHz, DMSO-d$_6$): δ ppm 9.68 (m, 1H), 7.25-7.21 (m, 2H), 6.91-6.87 (m, 2H), 6.43 (m, 1H), 4.92-4.85 (m, 1H), 4.41 (quin, J = 6.7 Hz, 1H), 4.32 (s, 1H), 3.71 (s, 3H), 1.35 (d, J = 6.7 Hz, 3H), 1.27-1.23 (m, 6H). |
| (structure 122) | 122<br>7 and 59 | 286 (M + H)+<br>¹H-NMR (400 MHz, DMSO-d$_6$): δ ppm 7.38-7.33 (m, 4H), 7.28-7.25 (m, 1H), 6.80 (br s, 1H), 4.24 (s, 1H), 3.82-3.78 (m, 1H), 3.63 (q, J = 6.8 Hz, 2H), 1.17-1.13 (m, 1H), 0.97 (t, J = 6.8 Hz, 3H), 0.59-0.54 (m, 1H), 0.47-0.32 (m, 3H). |
| (structure 123) | 123<br>1 and 59 | 294 (M + H)+<br>¹H-NMR (300 MHz, DMSO-d$_6$): δ ppm 10.00 (br s, 1H), 7.44 (s, 1H), 7.42-7.30 (m, 3H), 6.61 (d, J = 6.6 Hz, 1H), 4.57-4.53 (m, 1H), 4.38 (d, J = 1.8 Hz, 1H), 3.65 (q, J = 6.9 Hz, 2H), 1.39 (d, J = 6.9 Hz, 3H), 0.99 (t, J = 7.2 Hz, 3H). |
| (structure 124) | 124<br>1 and 59 | 328 (M + H)<br>¹H-NMR (300 MHz, DMSO-d$_6$): δ ppm 7.75 (s, 1H), 7.72-7.59 (m, 3H), 6.99 (br s, 1H), 4.68-4.62 (m, 1H), 4.38 (s, 1H), 3.65 (q, J = 6.6 Hz, 2H), 1.42 (d, J = 6.6 Hz, 3H), 1.01 (t, J = 4.5 Hz, 3H). |
| (structure 125) | 125<br>1 and 59 | 304 (M + H)+<br>¹H-NMR (300 MHz, DMSO-d$_6$): δ ppm 10.01 (br s, 1H), 7.42 (dd, J = 7.8, 6.0 Hz, 1H), 7.20 (d, J = 7.5 Hz, 2H), 7.12-7.06 (m, 1H), 6.62 (d, J = 7.2 Hz, 1H), 4.56 (quin, J = 6.9 Hz, 1H), 4.39 (s, 1H), 3.49 (d, J = 6.9 Hz, 2H), 1.40 (d, J = 6.6 Hz, 3H), 1.07-0.99 (m, 1H), 0.37-0.34 (m, 2H), 0.30-0.22 (m, 2H). |

-continued

| Structure | Compound No. Reference Ex. No. | Observed Mass and/or $^1$H NMR |
|---|---|---|
| 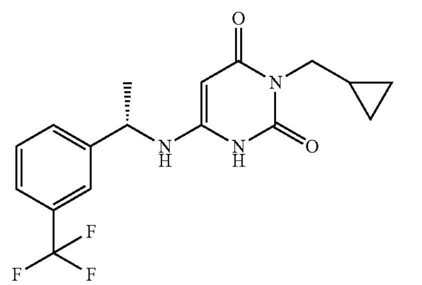 [SMILES: C[C@H](Nc1cc(=O)n(CC2CC2)c(=O)[nH]1)c1cccc(C(F)(F)F)c1] | 126<br>1 and 59 | 354 (M + H)+<br>$^1$H-NMR (300 MHz, CD$_3$OD): δ ppm 7.73-7.50 (m, 4H), 4.63 (q, J = 6.9 Hz, 1H), 3.62 (d, J = 7.2 Hz, 2H), 1.50 (d, J = 6.9 Hz, 3H) 1.17-1.10 (m, 1H), 0.45-0.39 (m, 2H), 0.32-0.26 (m, 2H). |
| 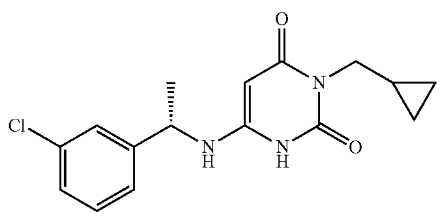 [SMILES: C[C@H](Nc1cc(=O)n(CC2CC2)c(=O)[nH]1)c1cccc(Cl)c1] | 127<br>1 and 59 | 320 (M + H)+<br>$^1$H-NMR (300 MHz, DMSO-d$_6$): δ ppm 10.01 (br s, 1H), 7.45 (s, 1H), 7.42-7.30 (m, 3H), 6.64 (d, J = 6.9 Hz, 1H), 4.58-4.53 (m, 1H), 4.39 (s, 1H), 3.50 (d, J = 7.2 Hz, 2H), 1.40 (d, J = 6.6 Hz, 3H) 1.07-1.03 (m, 1H), 0.37-0.31 (m, 2H), 0.25-0.22 (m, 2H). |
| 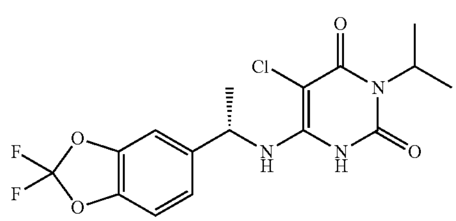 [SMILES: CC(C)n1c(=O)[nH]c(N[C@@H](C)c2ccc3c(c2)OC(F)(F)O3)c(Cl)c1=O] | 128<br>3 | 388 (M + H)+<br>$^1$H-NMR (400 MHz, DMSO-d$_6$): δ ppm 9.50 (br s, 1H), 7.52-7.22 (m, 3H), 4.87-4.72 (m, 1H), 4.52-4.41 (m, 1H), 1.60-1.48 (m, 3H), 1.41-1.27 (m, 6H). |
| 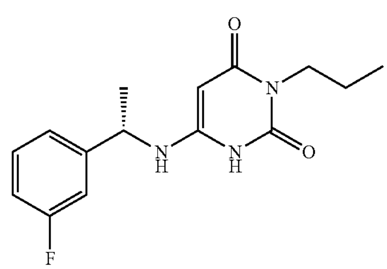 [SMILES: CCCn1c(=O)cc(N[C@@H](C)c2cccc(F)c2)[nH]c1=O] | 129<br>1 and 59 | 292 (M + H)+<br>$^1$H-NMR (300 MHz, DMSO-d$_6$): δ ppm 10.00 (br s, 1H), 7.40 (dt, J = 7.8 Hz, 0.6 Hz, 1H), 7.26 (d, J = 7.8 Hz, 2H), 7.09-7.06 (m, 1H), 6.60 (d, J = 6.9 Hz, 1H), 4.46 (q, J = 6.6 Hz, 1H), 4.38 (s, 1H), 3.60-3.55 (m, 2H), 1.47-1.39 (m, 5H), 0.79 (t, J = 7.5 Hz, 3H). |
| 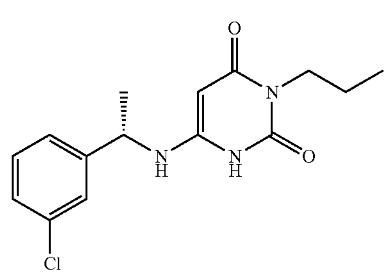 [SMILES: CCCn1c(=O)cc(N[C@@H](C)c2cccc(Cl)c2)[nH]c1=O] | 130<br>1 and 59 | 308 (M + H)+<br>$^1$H-NMR (300 MHz, DMSO-d$_6$): δ ppm 10.01 (br s, 1H), 7.44 (t, J = 0.9 Hz, 1H), 7.41-7.38 (m, 1H), 7.34-7.31 (m, 2H), 6.62 (d, J = 5.1 Hz, 1H), 4.55 (q, J = 6.7 Hz, 1H), 4.38 (s, 1H), 3.54 (dd, J = 6.0, 5.7 Hz, 2H), 1.47-1.39 (m, 5H), 0.84 (t, J = 7.5 Hz, 3H). |

-continued

| Structure | Compound No. Reference Ex. No. | Observed Mass and/or ¹H NMR |
|---|---|---|
| 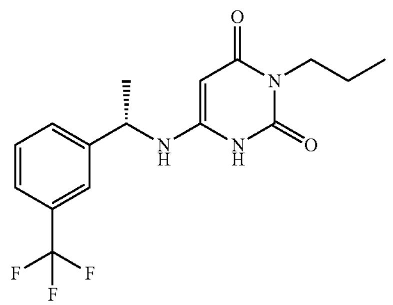 [SMILES: CCCn1c(=O)cc(N[C@@H](C)c2cccc(C(F)(F)F)c2)[nH]c1=O] | 131<br>1 and 59 | 342 (M + H)+<br>¹H-NMR (400 MHz, DMSO-$d_6$): δ ppm 10.05 (br s, 1H), 7.74 (s, 1H), 7.68-7.56 (m, 3H), 6.69 (d, J = 6.4 Hz, 1H), 4.70-4.63 (m, 1H), 4.40 (s, 1H), 3.59-3.54 (m, 2H), 1.49-1.40 (m, 5H), 0.86 (t, J = 6.0 Hz, 3H). |
| 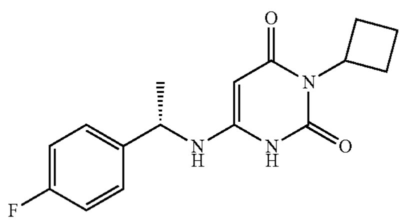 [SMILES: C[C@H](Nc1cc(=O)n(C2CCC2)c(=O)[nH]1)c1ccc(F)cc1] | 132<br>1 | 304 (M + H)+<br>¹H-NMR (400 MHz, DMSO-$d_6$): δ ppm 9.85 (br s, 1H), 7.37-7.33 (m, 2H), 7.18-7.13 (m, 2H), 6.52 (d, J = 7.4 Hz, 1H), 5.14-5.05 (m, 1H), 4.50 (quin, J = 6.8 Hz, 1H), 4.31 (s, 1H), 2.84-2.78 (m, 2H), 1.97-1.91 (m, 2H), 1.70-1.54 (m, 2H), 1.36 (t, J = 6.7 Hz, 3H). |
| 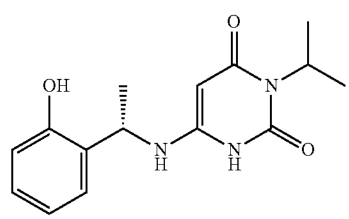 [SMILES: CC(C)n1c(=O)cc(N[C@@H](C)c2ccccc2O)[nH]c1=O] | 133<br>1 | 290 (M + H)+<br>¹H-NMR (400 MHz, DMSO-$d_6$): δ ppm 9.83 (br s, 1H), 9.68 (br s, 1H), 7.14 (dd, J = 7.4, 1.6 Hz, 1H), 7.07-7.03 (m, 1H), 6.81-6.74 (m, 2H), 6.42 (d, J = 7.0 Hz, 1H), 4.92-4.85 (m, 1H), 4.60 (quin, J = 6.8 Hz, 1H), 4.31 (d, J = 2.3 Hz, 1H), 1.35 (d, J = 7.0 Hz, 3H), 1.27-1.22 (m, 6H). |
| 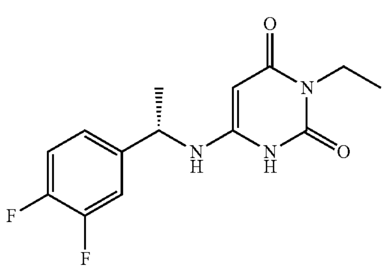 [SMILES: CCn1c(=O)cc(N[C@@H](C)c2ccc(F)c(F)c2)[nH]c1=O] | 134<br>1 | 296 (M + H)+<br>¹H-NMR (300 MHz, DMSO-$d_6$): δ ppm 10.03 (br s, 1H), 7.48-7.39 (m, 2H), 7.23-7.20 (m, 1H), 6.60 (d, J = 5.1 Hz, 1H) 4.58-4.53 (m, 1H), 4.38 (s, 1H), 3.66 (q, J = 5.1 Hz, 2H), 1.39 (d, J = 5.1 Hz, 3H), 0.99 (t, J = 5.1 Hz, 3H). |
| 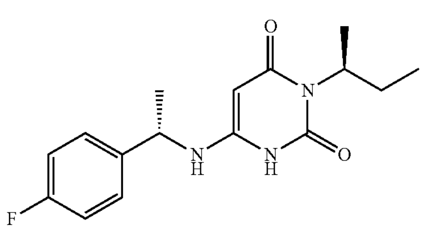 [SMILES: CC[C@H](C)n1c(=O)cc(N[C@@H](C)c2ccc(F)cc2)[nH]c1=O] | 135<br>1 | 306 (M + H)+<br>¹H-NMR (400 MHz, DMSO-$d_6$): δ ppm 9.95 (br s, 1H), 7.36 (dd, J = 9.0, 5.5 Hz, 2H), 7.18-7.14 (m, 2H), 6.54 (d, J = 7.0 Hz, 1H) 4.66 (br s, 1H), 4.54-4.49 (m, 1H), 4.34 (s, 1H), 1.97-1.86 (m, 1H), 1.65-1.55 (m, 1H), 1.38 (d, J = 6.8 Hz, 3H), 1.23 (d, J = 6.8 Hz, 3H), 0.70 (t, J = 6.8 Hz, 3H). |

-continued

| Structure | Compound No. Reference Ex. No. | Observed Mass and/or $^1$H NMR |
|---|---|---|
| (structure: 4-fluorophenyl-CH(CH₃)-NH group attached to pyrimidinedione with N-propyl) | 136<br>1 | 292 (M + H)+<br>$^1$H-NMR (400 MHz, DMSO-$d_6$): δ ppm 9.95 (br s, 1H), 7.36 (dd, J = 9.0, 5.5 Hz, 2H), 7.18-7.14 (m, 2H), 6.54 (d, J = 7.0 Hz, 1H) 4.56-4.49 (m, 1H), 4.35 (d, J = 2.3 Hz, 1H), 3.57-3.53 (m, 2H), 1.44-1.36 (m, 5H), 0.77 (t, J = 7.4 Hz, 3H). |
| (structure: phenyl-CH(CH₃)-NH group attached to pyrimidinedione with N-(6-fluoropyridin-2-yl)) | 137<br>65 | 327 (M + H)+<br>$^1$H-NMR (400 MHz, DMSO-$d_6$): δ ppm 10.36 (br s, 1H), 8.09 (q, J = 8.0 Hz, 1H), 7.39-7.35 (m, 4H), 7.30-7.22 (m, 3H), 6.87 (m, 1H), 4.61 (quin, J = 6.8 Hz, 1H), 4.49 (s, 1H), 1.44 (d, J = 6.8 Hz, 3H). |

Example 73

Myosin Inhibition Assay

Small molecule agents were assessed for their ability to inhibit the enzymatic activity of bovine cardiac myosin using a biochemical assay that couples the release of ADP (adenosine diphosphate) from cardiac myosin to an enzymatic coupling system consisting of pyruvate kinase and lactate dehydrogenase (PK/LDH) and monitoring the absorbance decrease of NADH (at 340 nm) as a function of time. PK converts ADP to ATP (adenosine triphosphate) by converting PEP (phosphoenolpyruvate) to pyruvate. Pyruvate is then converted to lactate by LDH by converting NADH (nicotinamide adenine dinucleotide) to NAD (oxidized nicotinamide adenine dinucleotide). The source of cardiac myosin was from bovine heart in the form of skinned myofibrils. Prior to testing small molecule agents, the bovine myofibrils were assessed for their calcium responsiveness and the calcium concentration that achieves either a 50% (pCa$_{50}$) or 75% (pCa$_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 0.4 mM PK/LDH, 50 uM ATP, 0.1 mg/mL BSA (bovine serum albumin), 10 ppm antifoam, 1 mM DTT, 0.5 mM NADH, 1.5 mM PEP at the desired free calcium concentration required to achieve either 50% or 75% activation of the myofibrils.

A dilution series of compound was created in DMSO such that the final desired concentration of compound would be achieved in a volume of 100 μL with a fixed DMSO concentration of 2% (v/v). Typically 2 μL of the dilution series were added to 96 well plate to achieve an 8 or 12 point dose response. Following the addition of 50 μL of a solution containing bovine cardiac myofibrils, PK/LDH and a solution of calcium (that achieved the desired activation), the enzymatic reaction was started with the addition of 50 μL of a solution containing ATP, PEP and NADH. The reaction progress was followed in a Molecular Devices M5e plate reader at ambient temperature using clear half area plates. The plate reader was configured to read absorbance at 340 nm in kinetics mode for 15 minutes. Data were recorded as the slope of the absorbance response to time. The slopes of the absorbance response as a function of time were normalized to slopes on the plate containing DMSO. This normalized rate was then plotted as a function of small molecule concentration and the data was fitted to a four-parameter fit using GraphPad Prism. The midpoint of this plot is the IC50 and is the concentration at which fifty percent of the total response is inhibited. Any agent that failed to achieve a fifty percent inhibition at the highest concentration tested was reported as an IC50 greater than the highest concentration tested (ie. IC50>25 uM).

TABLE 2

Myosin Inhibition Activity of Selected Compounds[a]

| Compound No. | Biochemical Activity (pCa$_{75}$) | Biochemical Activity (pCa$_{50}$) |
|---|---|---|
| 1 | +++ | +++ |
| 2 | ++ | |
| 3 | +++ | |
| 4 | +++ | |
| 5 | +++ | |
| 6 | +++ | |
| 7 | +++ | |
| 8 | +++ | |
| 9 | +++ | |
| 10 | +++ | |
| 11 | ++ | |
| 12 | +++ | |
| 13 | +++ | |
| 14 | +++ | |
| 15 | +++ | |
| 16 | ++ | |

TABLE 2-continued

Myosin Inhibition Activity of Selected Compounds[a]

| Compound No. | Biochemical Activity (pCa$_{75}$) | Biochemical Activity (pCa$_{50}$) |
|---|---|---|
| 17 | +++ | |
| 21 | +++ | |
| 22 | ++ | |
| 24 | +++ | |
| 25 | + | |
| 26 | +++ | |
| 27 | +++ | +++ |
| 28 | +++ | |
| 29 | +++ | |
| 30 | +++ | |
| 31 | +++ | |
| 32 | +++ | |
| 33 | +++ | |
| 34 | +++ | |
| 35 | +++ | +++ |
| 36 | | ++ |
| 37 | ++ | |
| 38 | +++ | +++ |
| 39 | +++ | |
| 40 | +++ | |
| 41 | +++ | |
| 42 | +++ | |
| 43 | +++ | |
| 44 | +++ | |
| 45 | +++ | +++ |
| 46 | ++ | |
| 47 | ++ | |
| 48 | ++ | ++ |
| 49 | +++ | +++ |
| 50 | +++ | |
| 51 | ++ | |
| 52 | +++ | |
| 53 | ++ | |
| 54 | ++ | ++ |
| 55 | +++ | |
| 56 | + | |
| 57 | | ++ |
| 58 | +++ | |
| 59 | +++ | |
| 61 | ++ | |
| 62 | | +++ |
| 63 | | +++ |
| 64 | | ++ |
| 65 | | ++ |
| 66 | | ++ |
| 67 | | +++ |
| 68 | | +++ |
| 69 | ++ | +++ |
| 70 | ++ | |
| 71 | | +++ |
| 72 | ++ | |
| 73 | ++ | |
| 74 | ++ | |
| 75 | ++ | |
| 76 | ++ | |
| 77 | ++ | |
| 78 | +++ | |
| 79 | ++ | |
| 80 | +++ | |
| 81 | ++ | |
| 82 | +++ | +++ |
| 83 | +++ | |
| 84 | +++ | |
| 85 | +++ | |
| 86 | ++ | |
| 90 | ++ | |
| 91 | ++ | |
| 92 | ++ | ++ |
| 93 | +++ | ++ |
| 94 | +++ | |
| 95 | +++ | +++ |
| 99 | +++ | |
| 100 | ++ | |
| 101 | | ++ |
| 102 | | ++ |
| 103 | | +++ |
| 104 | | +++ |
| 105 | | +++ |
| 106 | | +++ |
| 107 | | +++ |
| 108 | | +++ |
| 109 | | ++ |
| 110 | | ++ |
| 111 | | ++ |
| 112 | | +++ |
| 113 | | ++ |
| 114 | | +++ |
| 115 | | |
| 116 | | +++ |
| 117 | | +++ |
| 118 | | +++ |
| 119 | | +++ |
| 120 | | +++ |
| 121 | | +++ |
| 122 | | ++ |
| 123 | | +++ |
| 124 | | +++ |
| 125 | | +++ |
| 126 | | ++ |
| 127 | | +++ |
| 128 | | ++ |
| 129 | | ++ |
| 130 | | +++ |
| 131 | | +++ |
| 132 | | +++ |
| 133 | | +++ |
| 134 | | +++ |
| 135 | | +++ |
| 136 | | +++ |
| 137 | | +++ |

[a] +++ corresponds to IC50 values below 1 uM.
++ corresponds to IC50 values from 1 to 15 uM.
+ corresponds to IC50 values above 15 uM.

Selectivity against rabbit skeletal myofibrils was assessed as described above with the exception that the source of myosin was that of fast skeletal myosin from rabbit in the form of myofibrils. Dose responses against rabbit skeletal myofibrils were also determined as described above.

Example 74

Stereochemical Preference for Activity

Matched pairs of stereoisomers were tested for their ability to inhibit myosin activity as described above. The results are summarized in Table 3. In all cases, the (R) stereoisomer is significantly less active than the (S) stereoisomer.

117

TABLE 3

Relative activities of (S) and (R) stereoisomers[a]

| (S) Stereoisomer | | | (R) Stereoisomer | | |
|---|---|---|---|---|---|
| Cmpd No. | IC50 (pCa$_{75}$) | IC50 (pCa$_{50}$) | Cmpd No. | IC50 (pCa$_{75}$) | IC50 (pCa$_{50}$) |
| 1 | 0.67 µM | 0.56 µM | 19R | 23.93 µM | 51.87 µM |
| 21 | 0.39 µM | | 20R | 19.64 µM | |
| 59 | 0.45 µM | | 60R | >39.2 µM | |

[a]assay conducted using 0.5 µM myosin, therefore IC50 values below 1.0 µM are approximate.

Example 75

Cardiomyocyte Contractility Assay

Contractility of adult rat ventricular myocytes is determined by edge detection with an IonOptix contractility system. Aliquots of myocytes in Tyrode buffer (137 mM NaCl, 3.7 mM KCL, 0.5 mM MgCl$_2$, 1.5 mM CaCl$_2$, 4 mM HEPES, 11 mM glucose) are placed in a perfusion chamber (Series 20 RC-27NE; Warner Instruments), allowed to adhere to the coverslip, and then perfused with 37° C. Tyrode buffer. Myocytes are filed stimulated at 1 Hz and 10V. Only myocytes with clear striations, quiescent prior to pacing, with a cell length of 120-180 microns, a basal fractional shortening equal to 3-8% of the cell length, and a contraction velocity greater than 100 microns per second are used for contractility experiments. To determine the response to compounds, myocytes are first perfused for 60 seconds with Tyrodes buffer followed by 5 minutes of compound and a 140 second washout with Tyrodes buffer. Data is continuously recorded using IonOptix software. Contractility data is analyzed using Ionwizard software (IonOptix). For each cell, 10-20 contractility transients were averaged and compared under basal (no compound) and compound-treated conditions. Compound activity is measured by effects on fractional shortening (FS), where fractional shortening is the ratio of the peak length of the cell at contraction divided by the basal cell length normalized to 100% for an untreated cell.

TABLE 4

Inhibition of Cardiomyocyte Contraction by Selected Compounds[a]

| ID | Activity at 0.3 uM | Activity at 1.0 uM |
|---|---|---|
| 1 | ++ | +++ |
| 2 | ++ | +++ |
| 12 | n.d. | ++ |
| 19 | n.d. | + |
| 27 | ++ | n.d. |
| 67 | n.d. | +++ |

[a]+ represents fractional shorting inhibition values less than 33%.
++ represents fractional shorting inhibition values from 33% to 66%.
+++ represents fractional shorting inhibition values greater than 66%.

Example 76

Acute Pharmacodynamic Effect in Rat

Representative compounds were tested for their ability to modulate cardiac contractility in rat as a measure of in vivo target engagement. Fractional shortening, a measure of contractility, was determined by noting the change in the diameter of the left ventricle at the end of systole/contraction (LVESd) relative to diastole/relaxation (LVEDd) and expressing this change as the ratio FS=(LVEDd−LVESd)/LVEDd. Fed male Sprague-Dawley rats were lightly anesthetized with isofluorane and baseline fractional shortening was measured in the parasternal position using transthoracic echocardiography (TTE). Following this measurement, animals were recovered and received a single dose of compound (4 mg/kg) by oral gavage. At three hours post-dose, second and third echocardiograms were collected under light anesthesia to determine drug effects on contractility. Effects are represented in Table 5 as a percent reduction of baseline fractional shortening.

TABLE 5

Inhibition of Contractility in Rat by Selected Compounds[a]

| ID | % Reduction in Fractional Shortening 3 h post-dose |
|---|---|
| 1 | +++ |
| 45 | + |
| 48 | +++ |
| 49 | +++ |
| 69 | + |
| 70 | ++ |
| 71 | +++ |

[a]+ represents a relative change in fractional shortening less than 15%.
++ represents a relative change in fractional shortening between 15-30%.
+++ presents a relative change in fractional shortening greater than 30%.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate

What is claimed is:
1. A method of treating hypertrophic cardiomyopathy (HCM), comprising administering to a subject in need thereof an effective amount of a compound having the formula:

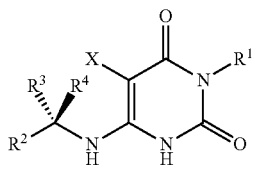

or a pharmaceutically acceptable salt thereof, wherein
R$^1$ is a member selected from the group consisting of C$_1$-C$_8$ alkyl, C$_3$-C$_8$ cycloalkyl, C$_3$-C$_8$ cycloalkyl-C$_1$-C$_4$ alkyl, 4-to 7-membered heterocycloalkyl, phenyl, phenyl-C$_1$-C$_4$ alkyl, 5-to 6-membered heteroaryl and 5-to 6-membered heteroaryl-C$_1$-C$_4$ alkyl, wherein each R$^1$ is optionally substituted with from 1-3 R$^a$;
R$^2$ is a member selected from the group consisting of phenyl, phenyl-C$_1$-C$_4$ alkyl, 5-to 6-membered heteroaryl and 5-to 6-membered heteroaryl-$C_1$-$C_4$ alkyl, wherein each $R^2$ is optionally substituted with from 1-5 $R^b$;

$R^3$ is a member selected from the group consisting of $C_1$-$C_4$ alkyl, $C_3$-$C_4$ cycloalkyl, and 4-to 7-membered heterocycloalkyl wherein each $R^3$ is optionally substituted with from 1-3 $R^c$;

$R^4$ is H;

X is a member selected from the group consisting of H and F;

each $R^a$ is independently selected from the group consisting of halo, CN, hydroxyl, $C_1$-$C_4$ alkyl, $C_1$-$C_4$ haloalkyl, $C_1$-$C_4$ alkoxy, phenyl, phenyl-$C_1$-$C_4$ alkyl, phenyl-$C_1$-$C_4$ alkoxy, phenoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from the group consisting of H, $C_1$-$C_4$ alkyl and phenyl, or optionally $R^{a1}$ and $R^{a2}$ when attached to a nitrogen atom are combined to form a 4-to 6-membered ring;

each $R^b$ is independently selected from the group consisting of halo, CN, hydroxyl, $C_1$-$C_4$ alkyl, $C_1$-$C_4$ haloalkyl, $C_1$-$C_4$ alkoxy, phenoxy, phenyl-$C_1$-$C_4$ alkoxy, methylenedioxy, difluoromethylenedioxy, —$COR^{b1}$, —$CO_2R^{b1}$, —$SO_2R^{b1}$, —$SO_2NR^{b1}R^{b2}$, $CONR^{b1}R^{b2}$, $NR^{b1}R^{b2}$, 5-to 6-membered heteroaryl, and 5-to 6-membered heterocyclyl optionally substituted with oxo, wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4-to 6-membered ring; and each $R^c$ is independently selected from the group consisting of halo, hydroxyl and $C_1$-$C_2$ alkoxy.

2. A method in accordance with claim 1, wherein, $R^1$ is a member selected from the group consisting of $C_1$-$C_8$ alkyl, $C_3$-$C_8$ cycloalkyl, 4-to 7-membered heterocycloalkyl, phenyl, and 5-to 6-membered heteroaryl, wherein each $R^1$ is optionally substituted with from 1-3 $R^a$;

$R^2$ is phenyl, which is optionally substituted with from 1-5 $R^b$;

$R^3$ is a member selected from the group consisting of $C_1$-$C_4$ alkyl, $C_3$-$C_4$ cycloalkyl, and 4-to 7-membered heterocycloalkyl wherein each $R^3$ is optionally substituted with from 1-2 $R^c$;

$R^4$ is H;

X is a member selected from the group consisting of H and F;

each $R^a$ is independently selected from the group consisting of halo, CN, $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from the group consisting of H and $C_1$-$C_4$ alkyl or optionally $R^{a1}$ and $R^{a2}$ when attached to a nitrogen atom are combined to form a 4-to 6-membered ring;

each $R^b$ is independently selected from the group consisting of halo, CN, $C_1$-$C_4$ alkyl, $C_1$-$C_4$ alkoxy, —$COR^{b1}$, —$CO_2R^{b1}$, —$SO_2R^{b1}$, —$SO_2NR^{b1}R^{b2}$, $CONR^{b1}R^{b2}$, $NR^{b1}R^{b2}$, 5-to 6-membered heteroaryl, and 5-to 6-membered heterocyclyl optionally substituted with oxo, wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4-to 6-membered ring; and each $R^c$ is independently selected from the group consisting of halo and $C_1$-$C_2$ alkoxy.

3. A method in accordance with claim 1, wherein X is H.

4. A method in accordance with claim 1, wherein $R^1$ is selected from the group consisting of $C_3$-$C_4$ alkyl, $C_3$-$C_5$ cycloalkyl, and 4-to 6-membered heterocycloalkyl, wherein each le is optionally substituted with from 1-2 $R^a$.

5. A method in accordance with claim 1, wherein $R^1$ is selected from the group consisting of phenyl and 5-to 6-membered heteroaryl, wherein each $R^1$ is optionally substituted with from 1-3 $R^a$.

6. A method in accordance with claim 1, wherein $R^1$ is selected from the group consisting of $C_3$-$C_4$ alkyl, $C_3$-$C_5$ cycloalkyl, and 4-to 6-membered heterocycloalkyl.

7. A method in accordance with claim 1, wherein $R^1$ is 4-to 6-membered heterocycloalkyl, optionally substituted with from 1-2 $R^a$ selected from the group consisting of $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^2$ is independently selected from the group consisting of H and $C_1$-$C_4$ alkyl.

8. A method in accordance with claim 1, wherein $R^1$ is selected from the group consisting of cyclobutyl, isopropyl, isobutyl, 1-methoxypropan-2-yl, cyclopentyl, cyclohexyl, 4-tetrahydropyranyl, 1-(methylsulfonyl)piperidin-4-yl, 1-(methoxycarbonyl) piperidin-4-yl, 4,4-difluorocyclohexyl, phenyl, 2-pyridyl, 3-pyridyl, 3-isoxazolyl, 5-isoxazolyl, and 1-methyl-3-pyrazolyl.

9. A method in accordance with claim 1, wherein $R^2$ is optionally substituted with from 1-2 $R^b$.

10. A method in accordance with claim 1, wherein $R^2$ is selected from the group consisting of phenyl, 3-methylphenyl, 2-fluorophenyl, 3-fluorophenyl, 4-fluorophenyl, 2,5-difluorophenyl, 3,5-difluorophenyl, 3-chlorophenyl, 3-methoxyphenyl, 3-(3-oxazolidin-2-onyl) phenyl, 3-(2-methyl-1-imidazyl)phenyl, 3-(1-pyrazolyl)phenyl, and 3-(1,2,4-triazol-1-yl)phenyl.

11. A method in accordance with claim 1, wherein $R^3$ is selected from the group consisting of $C_1$-$C_4$ alkyl, $C_1$-$C_4$ alkoxyalkyl, and $C_3$-$C_4$ cycloalkyl.

12. A method in accordance with claim 1, wherein $R^3$ is selected from the group consisting of methyl, ethyl, propyl, cyclopropyl, cyclobutyl and 2-methoxymethyl.

13. A method in accordance with claim 1, wherein $R^3$ is methyl.

14. A method in accordance with claim 1, wherein $R^1$ is isopropyl; $R^2$ is optionally substituted with 1-2 $R^b$; and $R^3$ is methyl.

15. A method in accordance with claim 1, wherein $R^1$ is 4-to 6-membered heterocycloalkyl, optionally substituted with from 1-2 $R^a$ selected from the group consisting of $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from the group consisting of H and $C_1$-$C_4$ alkyl; $R^2$ is optionally substituted with 1-2 $R^b$; and $R^3$ is methyl.

16. A method in accordance with claim 1, wherein $R^1$ is selected from the group consisting of phenyl and 5-to 6-membered heteroaryl, wherein each $R^1$ is optionally substituted with from 1-3 $R^a$; $R^2$ is optionally substituted with from 1-2 $R^b$; and $R^3$ is methyl.

17. A method in accordance with claim 1, wherein said compound is selected from the group consisting of:

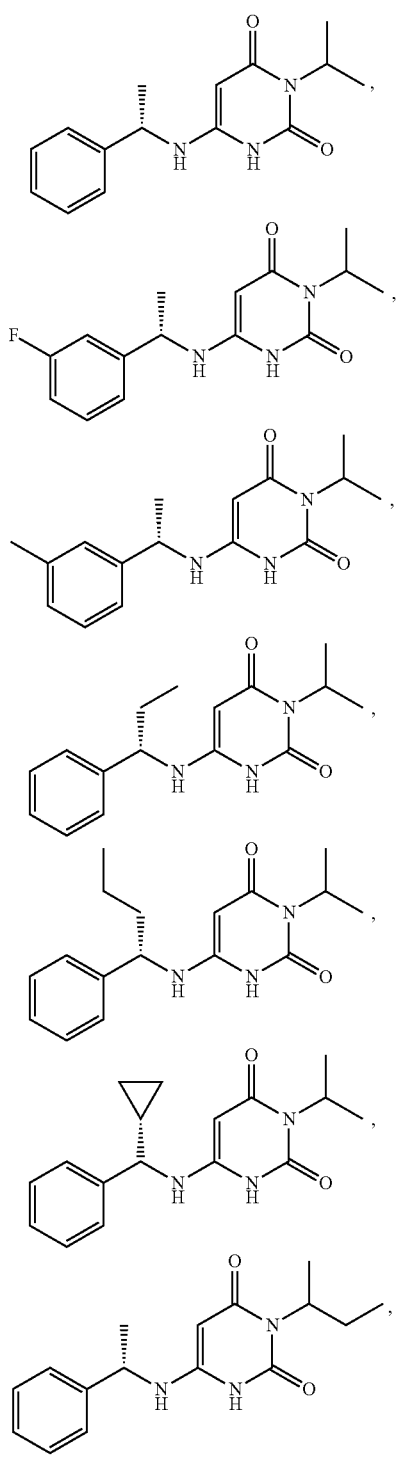
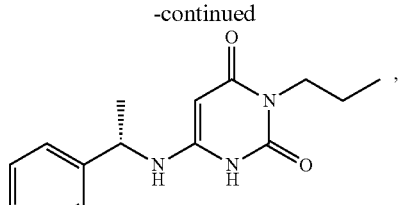
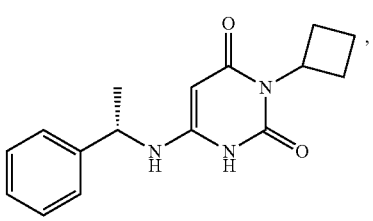
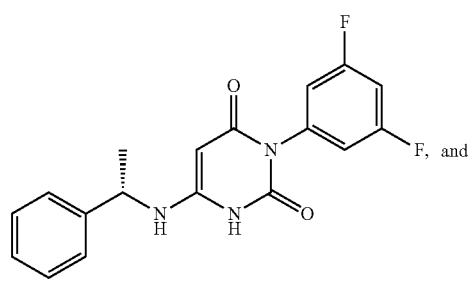
or a pharmaceutically acceptable salt thereof.
18. A method in accordance with claim 1, wherein said compound is
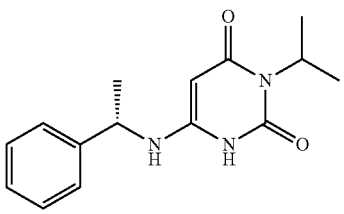 [SMILES: CC(C)n1c(=O)cc(N[C@@H](C)c2ccccc2)[nH]c1=O]
or a pharmaceutically acceptable salt thereof.
* * * * *